US010016575B2

(12) United States Patent
Vazales et al.

(10) Patent No.: US 10,016,575 B2
(45) Date of Patent: Jul. 10, 2018

(54) CLEANING DEVICES, SYSTEMS AND METHODS

(71) Applicant: ENDOCLEAR LLC, San Ramon, CA (US)

(72) Inventors: Brad Eugene Vazales, Petoskey, MI (US); David Mark Chersky, San Ramon, CA (US)

(73) Assignee: ENDOCLEAR LLC, San Ramon, CA (US)

( * ) Notice: Subject to any disclaimer, the term of this patent is extended or adjusted under 35 U.S.C. 154(b) by 314 days.

(21) Appl. No.: 14/727,665

(22) Filed: Jun. 1, 2015

(65) Prior Publication Data

US 2015/0343182 A1 Dec. 3, 2015

Related U.S. Application Data

(60) Provisional application No. 62/007,328, filed on Jun. 3, 2014.

(51) Int. Cl.
A61M 25/00 (2006.01)
A61M 16/04 (2006.01)
(Continued)

(52) U.S. Cl.
CPC ............ A61M 25/00 (2013.01); A61B 1/122 (2013.01); A61M 16/0463 (2013.01);
(Continued)

(58) Field of Classification Search
CPC .. A61M 2025/0008; A61M 2025/0019; A61M 2025/1086; A61M 25/0075;
(Continued)

(56) References Cited

U.S. PATENT DOCUMENTS 62,816 A 3/1867 Christoffel
139,633 A 6/1873 Turner
(Continued)

FOREIGN PATENT DOCUMENTS

DE 3107392 9/1982
EP 0343094 11/1989
(Continued)

OTHER PUBLICATIONS

Pinciroli, Riccardo MD et al., Endotracheal tubes cleaned with a novel mechanism for secretion removal, Nov. 2016, vol. 61 No. 11, pp. 1431-1439.
(Continued)

Primary Examiner — Laura Bouchelle
Assistant Examiner — Tasnim M Ahmed
(74) Attorney, Agent, or Firm — Knobbe Martens Olson & Bear LLP

(57) ABSTRACT

Cleaning systems and devices are provided for cleaning body-inserted tubes (e.g., endotracheal tubes, chest cleaning tubes). In one embodiment, a closed suction system includes a suction catheter having at least one deployable (e.g., inflatable) cleaning member at a distal portion of the suction catheter and at least one suction opening distal to the cleaning member. The closed suction system module may include a control unit at its proximal end adapted to facilitate operation in one of the following three operational states: i) a first operational state in which only the cleaning member is functional, ii) a second operational state in which only suction is functional, or iii) a third operational state in which neither suction nor the cleaning member is functional.

17 Claims, 28 Drawing Sheets

(51) Int. Cl.
*A61M 25/10* (2013.01)
*A61B 1/12* (2006.01)
*A61M 25/01* (2006.01)
*A61B 1/267* (2006.01)

(52) U.S. Cl.
CPC ......... *A61M 25/1002* (2013.01); *A61B 1/267* (2013.01); *A61M 25/0045* (2013.01); *A61M 25/0074* (2013.01); *A61M 25/0075* (2013.01); *A61M 25/0097* (2013.01); *A61M 25/0111* (2013.01); *A61M 2025/0008* (2013.01); *A61M 2025/0019* (2013.01); *A61M 2025/0079* (2013.01); *A61M 2025/1086* (2013.01); *A61M 2205/0205* (2013.01); *A61M 2205/581* (2013.01); *A61M 2205/582* (2013.01); *A61M 2205/583* (2013.01); *A61M 2209/10* (2013.01)

(58) Field of Classification Search
CPC .............. A61M 25/0074; A61M 16/04; A61M 16/0436; A61M 16/042; A61M 1/0058; A61M 1/0078; A61M 2025/10
See application file for complete search history.

(56) References Cited

U.S. PATENT DOCUMENTS

| | | | |
|---|---|---|---|
| 491,791 A | 2/1893 | Wilson | |
| 655,313 A | 8/1900 | Tucker | |
| 707,913 A | 8/1902 | Garrison | |
| 1,040,088 A | 10/1912 | Wright et al. | |
| 1,166,901 A | 1/1916 | Grobl | |
| 1,588,557 A | 6/1926 | Thompson et al. | |
| 1,608,347 A | 11/1926 | Thompson et al. | |
| 1,612,842 A | 1/1927 | Thompson et al. | |
| 1,656,465 A | 1/1928 | Baker | |
| 1,738,601 A | 12/1929 | Metzger | |
| 2,018,124 A | 10/1935 | Forster | |
| 2,038,170 A | 4/1936 | Flavin | |
| 2,073,811 A | 3/1937 | Shultz | |
| 2,125,864 A | 8/1938 | Auckland | |
| 2,157,421 A | 5/1939 | McFarland | |
| 2,173,606 A | 9/1939 | Forster | |
| 2,175,726 A | 10/1939 | Gebauer | |
| 2,552,339 A | 5/1951 | Moon | |
| 2,599,077 A | 6/1952 | Sturgis | |
| 2,653,334 A | 9/1953 | Bay | |
| 2,930,059 A | 3/1960 | Frank | |
| 2,932,837 A | 4/1960 | Nooy | |
| 2,957,189 A | 10/1960 | Nelson et al. | |
| 2,958,884 A | 11/1960 | Hill et al. | |
| 3,096,756 A | 7/1963 | Rosenfeld et al. | |
| 3,105,555 A | 10/1963 | Villalon, Jr. | |
| 3,130,431 A | 4/1964 | Reinhart | |
| 3,257,698 A | 6/1966 | Ruegsegger | |
| 3,445,879 A | 5/1969 | Taylor | |
| 3,525,111 A | 8/1970 | Arx | |
| 3,610,242 A | 10/1971 | Sheridan et al. | |
| 3,667,475 A | 6/1972 | Venturelli et al. | |
| 3,669,098 A | 6/1972 | Takahashi | |
| 3,776,222 A | 12/1973 | Smiddy | |
| 3,946,459 A | 3/1976 | Armstrong | |
| 3,948,273 A | 4/1976 | Sanders | |
| 3,977,331 A | 8/1976 | Clavin | |
| 3,991,762 A | 11/1976 | Radford | |
| 3,996,938 A | 12/1976 | Clark | |
| 4,031,590 A | 6/1977 | Clavin | |
| 4,041,936 A | 8/1977 | Carden | |
| 4,185,639 A | 1/1980 | Linder | |
| 4,222,142 A | 9/1980 | DiProspero | |
| 4,319,378 A | 3/1982 | Bowman et al. | |
| 4,327,720 A | 5/1982 | Bronson et al. | |
| 4,342,315 A | 8/1982 | Jackson | |
| 4,351,328 A | 9/1982 | Bodai | |
| 4,365,381 A | 12/1982 | Neuman | |
| 4,502,482 A | 3/1985 | DeLuccia et al. | |
| 4,527,553 A | 7/1985 | Upsher | |
| 4,538,316 A | 9/1985 | Reinhart et al. | |
| 4,565,187 A | 1/1986 | Soloway | |
| 4,567,882 A | 2/1986 | Heller | |
| 4,584,998 A | 4/1986 | McGrail | |
| 4,585,000 A | 4/1986 | Hershenson | |
| 4,586,491 A | 5/1986 | Carpenter | |
| 4,622,709 A | 11/1986 | Matsuda | |
| 4,637,389 A | 1/1987 | Heyden | |
| 4,646,722 A | 3/1987 | Silverstein et al. | |
| 4,662,871 A | 5/1987 | Rafelson | |
| 4,698,932 A | 10/1987 | Schneider | |
| 4,805,611 A | 2/1989 | Hodgkins | |
| 4,815,459 A | 3/1989 | Beran | |
| 4,825,859 A | 5/1989 | Lambert | |
| 4,827,553 A | 5/1989 | Turpin, Sr. et al. | |
| 4,846,153 A | 7/1989 | Berci et al. | |
| 4,850,348 A | 7/1989 | Pell et al. | |
| 4,877,016 A | 10/1989 | Kantor et al. | |
| 4,889,106 A | 12/1989 | Watanabe | |
| 4,892,095 A | 1/1990 | Nakhgevany | |
| 4,976,261 A | 12/1990 | Gluck et al. | |
| 5,000,260 A | 3/1991 | Fontenot | |
| 5,003,657 A | 4/1991 | Boiteau et al. | |
| 5,029,580 A | 7/1991 | Radford et al. | |
| 5,030,201 A | 7/1991 | Palestrant | |
| 5,065,754 A | 11/1991 | Jensen | |
| 5,083,561 A | 1/1992 | Russo | |
| 5,168,593 A | 12/1992 | Poje et al. | |
| 5,176,638 A | 1/1993 | Don Michael | |
| 5,193,525 A | 3/1993 | Silverstein et al. | |
| 5,193,544 A | 3/1993 | Jaffe | |
| 5,203,320 A | 4/1993 | Augustine | |
| 5,240,675 A | 8/1993 | Wilk et al. | |
| 5,251,356 A | 10/1993 | Oaki et al. | |
| 5,257,620 A | 11/1993 | Schermerhorn | |
| 5,271,381 A | 12/1993 | Ailinger et al. | |
| 5,279,549 A | 1/1994 | Ranford | |
| 5,285,778 A | 2/1994 | Mackin | |
| 5,287,848 A | 2/1994 | Cubb et al. | |
| 5,297,310 A | 3/1994 | Coz et al. | |
| 5,329,940 A | 7/1994 | Adair | |
| 5,335,655 A * | 8/1994 | Kee .................... | A61M 1/0031 116/138 |
| 5,337,730 A | 8/1994 | Maguire | |
| 5,364,358 A | 11/1994 | Hewitt et al. | |
| 5,375,589 A | 12/1994 | Bhatta | |
| 5,383,243 A | 1/1995 | Thacker et al. | |
| 5,400,771 A | 3/1995 | Pirak et al. | |
| 5,405,755 A | 4/1995 | Markus et al. | |
| 5,407,807 A | 4/1995 | Markus | |
| 5,419,310 A | 5/1995 | Frassica et al. | |
| 5,431,150 A | 7/1995 | Yabe et al. | |
| 5,431,152 A | 7/1995 | Flam et al. | |
| 5,431,637 A | 7/1995 | Okada et al. | |
| 5,447,418 A | 9/1995 | Takeda et al. | |
| 5,483,951 A | 1/1996 | Frassica et al. | |
| 5,513,628 A | 5/1996 | Coles et al. | |
| 5,520,607 A | 5/1996 | Frassica et al. | |
| 5,540,225 A | 7/1996 | Schutt | |
| 5,578,006 A | 11/1996 | Schon | |
| 5,603,688 A | 2/1997 | Upsher | |
| 5,615,439 A | 4/1997 | Bourrelly | |
| 5,630,795 A | 5/1997 | Kuramoto et al. | |
| 5,636,625 A | 6/1997 | Miyagi et al. | |
| 5,643,221 A | 7/1997 | Bullard | |
| 5,647,358 A | 7/1997 | Vilasi | |
| 5,653,231 A | 8/1997 | Bell | |
| 5,667,476 A | 9/1997 | Frassica et al. | |
| 5,676,635 A | 10/1997 | Levin | |
| 5,687,714 A | 11/1997 | Kolobow et al. | |
| 5,692,729 A | 12/1997 | Harhen | |
| 5,695,448 A | 12/1997 | Kimura et al. | |
| 5,702,348 A | 12/1997 | Harhen | |
| 5,709,691 A | 1/1998 | Morejon | |
| 5,713,849 A | 2/1998 | Bosma et al. | |
| 5,725,478 A | 3/1998 | Saad | |
| 5,733,242 A | 3/1998 | Rayburn et al. | |

(56) References Cited

U.S. PATENT DOCUMENTS

| | | | |
|---|---|---|---|
| 5,738,091 A * | 4/1998 | Kee | A61M 1/0064 128/202.27 |
| 5,768,741 A | 6/1998 | Leiman et al. | |
| 5,791,337 A | 8/1998 | Coles et al. | |
| 5,795,404 A | 8/1998 | Murphy et al. | |
| 5,797,993 A | 8/1998 | Woehleke | |
| 5,819,727 A | 10/1998 | Linder | |
| 5,827,177 A | 10/1998 | Oneda et al. | |
| 5,830,127 A | 11/1998 | DeCastro | |
| 5,832,920 A | 11/1998 | Field | |
| 5,836,918 A | 11/1998 | Dondlinger | |
| 5,840,251 A | 11/1998 | Iwaki | |
| 5,842,973 A | 12/1998 | Bullard | |
| 5,845,634 A | 12/1998 | Parker | |
| 5,846,183 A | 12/1998 | Chilcoat | |
| 5,876,329 A | 3/1999 | Harhen | |
| 5,897,567 A | 4/1999 | Ressemann et al. | |
| 5,902,413 A | 5/1999 | Puszko et al. | |
| 5,904,648 A | 5/1999 | Arndt et al. | |
| 5,913,816 A | 6/1999 | Sanders | |
| 5,921,917 A | 7/1999 | Barthel et al. | |
| 5,931,831 A | 8/1999 | Linder | |
| 5,941,816 A | 8/1999 | Barthel et al. | |
| 5,964,004 A | 10/1999 | Bean | |
| 5,964,223 A | 10/1999 | Baran | |
| 5,966,768 A | 10/1999 | Hahn | |
| 5,987,683 A | 11/1999 | Leiman et al. | |
| 6,045,623 A | 4/2000 | Cannon | |
| 6,047,431 A | 4/2000 | Canonica | |
| 6,082,361 A | 7/2000 | Morejon | |
| 6,086,529 A | 7/2000 | Arndt et al. | |
| 6,115,523 A | 9/2000 | Choi et al. | |
| 6,120,434 A | 9/2000 | Kimura et al. | |
| 6,123,666 A | 9/2000 | Wrenn et al. | |
| 6,168,579 B1 | 1/2001 | Tsugita | |
| 6,174,280 B1 | 1/2001 | Oneda et al. | |
| 6,189,533 B1 | 2/2001 | Simon et al. | |
| 6,190,330 B1 | 2/2001 | Harhen | |
| 6,227,200 B1 | 5/2001 | Crump et al. | |
| 6,276,017 B1 | 8/2001 | Lino et al. | |
| 6,276,018 B1 | 8/2001 | Leiman et al. | |
| 6,286,172 B1 | 9/2001 | Castagnoli | |
| 6,299,576 B1 | 10/2001 | Ouchi | |
| 6,318,368 B1 | 11/2001 | Morejon | |
| 6,319,195 B1 | 11/2001 | Nakaichi et al. | |
| 6,322,498 B1 | 11/2001 | Gravenstein et al. | |
| 6,350,231 B1 | 2/2002 | Ailinger et al. | |
| 6,353,774 B1 | 3/2002 | Goldenberg et al. | |
| 6,354,993 B1 | 3/2002 | Kaplan et al. | |
| 6,379,296 B1 | 4/2002 | Baggett | |
| 6,398,775 B1 | 6/2002 | Perkins et al. | |
| 6,461,294 B1 | 10/2002 | Oneda et al. | |
| 6,484,345 B2 | 11/2002 | Seder et al. | |
| 6,494,208 B1 | 12/2002 | Morejon | |
| 6,500,271 B1 | 12/2002 | Moore et al. | |
| 6,517,477 B1 | 2/2003 | Wendlandt | |
| 6,520,907 B1 | 2/2003 | Foley et al. | |
| 6,526,976 B1 | 3/2003 | Baran | |
| 6,527,761 B1 | 3/2003 | Soltesz et al. | |
| 6,530,881 B1 | 3/2003 | Ailinger et al. | |
| 6,538,431 B2 | 3/2003 | Couchman et al. | |
| 6,543,447 B2 | 4/2003 | Pacey | |
| 6,554,765 B1 | 4/2003 | Yarush et al. | |
| 6,553,313 B1 | 5/2003 | Knighton et al. | |
| 6,569,089 B1 | 5/2003 | Covington et al. | |
| 6,585,639 B1 | 7/2003 | Kotmel et al. | |
| 6,629,924 B2 | 10/2003 | Aydelotte | |
| 6,655,377 B2 | 12/2003 | Pacey | |
| 6,679,262 B1 | 1/2004 | Morejon | |
| 6,681,783 B2 | 1/2004 | Kawazoe | |
| 6,699,182 B2 | 3/2004 | Pilvisto | |
| 6,699,331 B1 | 3/2004 | Kritzler | |
| 6,725,492 B2 | 4/2004 | Moore et al. | |
| 6,729,334 B1 | 5/2004 | Baran | |
| 6,775,872 B1 | 8/2004 | Appleton et al. | |
| 6,775,874 B2 | 8/2004 | Horton | |
| 6,793,661 B2 | 9/2004 | Hamilton et al. | |
| 6,832,986 B2 | 12/2004 | Chhibber et al. | |
| 6,843,769 B1 | 1/2005 | Gandarias | |
| 6,889,400 B2 | 5/2005 | Kawazoe et al. | |
| 6,889,402 B2 | 5/2005 | Galantai | |
| 6,890,298 B2 | 5/2005 | Berci et al. | |
| 6,920,662 B2 | 7/2005 | Moore | |
| 6,928,686 B2 | 8/2005 | Tomooka et al. | |
| 6,929,600 B2 | 8/2005 | Hill | |
| 7,036,510 B2 | 5/2006 | Zgoda et al. | |
| 7,051,737 B2 | 5/2006 | Kolobow et al. | |
| 7,052,456 B2 | 5/2006 | Simon | |
| 7,056,284 B2 | 6/2006 | Martone et al. | |
| 7,060,135 B2 | 6/2006 | Morejon | |
| 7,081,097 B2 | 7/2006 | Martone et al. | |
| 7,107,991 B2 | 9/2006 | Kolobow | |
| 7,121,336 B2 | 10/2006 | Hatley | |
| 7,128,071 B2 | 10/2006 | Brain | |
| 7,159,590 B2 | 1/2007 | Rife | |
| 7,182,728 B2 | 2/2007 | Cubb et al. | |
| 7,243,653 B2 | 7/2007 | Nelson | |
| 7,297,105 B2 | 11/2007 | Mackin | |
| 7,322,357 B2 | 1/2008 | Nelson | |
| 7,458,375 B2 | 12/2008 | Schwartz et al. | |
| 7,458,955 B2 | 12/2008 | Owens et al. | |
| 7,469,700 B2 | 12/2008 | Baran | |
| 7,472,705 B2 | 1/2009 | Baran | |
| 7,473,219 B1 | 1/2009 | Glenn | |
| 7,478,636 B2 | 1/2009 | Madsen et al. | |
| 7,503,328 B2 | 3/2009 | Kolobow et al. | |
| 7,527,058 B2 | 5/2009 | Wright et al. | |
| 7,552,729 B2 | 6/2009 | O'Mara | |
| 7,607,436 B2 | 10/2009 | Smaldone et al. | |
| 7,658,708 B2 | 2/2010 | Schwarts et al. | |
| 7,658,711 B2 | 2/2010 | Klemm | |
| 7,669,600 B2 | 3/2010 | Morejon | |
| 8,142,422 B2 | 3/2012 | Makower et al. | |
| 8,157,919 B2 | 4/2012 | Vazales et al. | |
| 8,381,345 B2 | 2/2013 | Vazales et al. | |
| 8,382,908 B2 | 2/2013 | Vazales et al. | |
| 8,458,844 B2 | 6/2013 | Vazales et al. | |
| 8,468,637 B2 | 6/2013 | Vazales et al. | |
| 8,534,287 B2 | 9/2013 | Vazales et al. | |
| 8,601,633 B2 | 12/2013 | Vazales et al. | |
| 9,095,286 B2 | 8/2015 | Vazales et al. | |
| 9,332,891 B2 | 5/2016 | Vazales et al. | |
| 9,386,907 B2 | 7/2016 | Vazales et al. | |
| 9,398,837 B2 | 7/2016 | Vazales et al. | |
| 9,445,714 B2 | 9/2016 | Vazales et al. | |
| 9,479,012 B2 | 10/2016 | Nahidipour | |
| 9,579,012 B2 | 2/2017 | Vazales et al. | |
| 9,855,111 B2 | 1/2018 | Vazales et al. | |
| 2001/0014768 A1 | 8/2001 | Kaplan et al. | |
| 2002/0068851 A1 | 6/2002 | Gravenstein et al. | |
| 2002/0108614 A1 | 8/2002 | Schultz | |
| 2002/0162557 A1 | 11/2002 | Simon et al. | |
| 2003/0050686 A1 | 3/2003 | Raeder-Devens et al. | |
| 2003/0083547 A1 | 5/2003 | Hamilton et al. | |
| 2003/0109837 A1 | 6/2003 | McBride-Sakal | |
| 2003/0188749 A1 | 10/2003 | Nichols et al. | |
| 2003/0209258 A1 | 11/2003 | Morejon | |
| 2003/0213501 A1 | 11/2003 | Thomson et al. | |
| 2004/0039252 A1 | 2/2004 | Koch, III | |
| 2004/0084050 A1 | 5/2004 | Baran | |
| 2004/0154115 A1 | 8/2004 | Schultz | |
| 2004/0176731 A1 | 9/2004 | Cheng et al. | |
| 2004/0181194 A1 | 9/2004 | Perkins | |
| 2004/0187892 A1 | 9/2004 | Maguire, Jr. et al. | |
| 2004/0187893 A1 | 9/2004 | Maguire, Jr. et al. | |
| 2004/0215061 A1 | 10/2004 | Kimmel et al. | |
| 2004/0220451 A1 | 11/2004 | Gravenstein et al. | |
| 2004/0221852 A1 | 11/2004 | Madsen et al. | |
| 2005/0039754 A1 | 2/2005 | Simon | |
| 2005/0090709 A1 | 4/2005 | Okada et al. | |
| 2005/0090712 A1 | 4/2005 | Cubb | |
| 2005/0172971 A1 | 8/2005 | Kolobow et al. | |
| 2005/0182297 A1 | 8/2005 | Gravenstein et al. | |
| 2005/0235995 A1 | 10/2005 | Tresnak et al. | |

(56) References Cited

U.S. PATENT DOCUMENTS

| | | |
|---|---|---|
| 2006/0004260 A1 | 1/2006 | Boedeker et al. |
| 2006/0069312 A1 | 3/2006 | O-Connor |
| 2006/0076023 A1* | 4/2006 | Rapacki .......... A61B 17/12022 |
| | | 128/207.15 |
| 2006/0090761 A1 | 5/2006 | Kurrus |
| 2006/0100483 A1 | 5/2006 | Sundet et al. |
| 2006/0102200 A1 | 5/2006 | Esquenet et al. |
| 2006/0130847 A1 | 6/2006 | Morejon |
| 2006/0135947 A1 | 6/2006 | Soltesz et al. |
| 2006/0157059 A1 | 7/2006 | Johnson et al. |
| 2006/0191087 A1 | 8/2006 | Maguire, Jr. et al. |
| 2006/0202387 A1 | 9/2006 | Durand et al. |
| 2006/0207602 A1 | 9/2006 | Kolobow et al. |
| 2006/0264988 A1 | 11/2006 | Boyle |
| 2006/0287667 A1 | 12/2006 | Abela |
| 2007/0049794 A1 | 3/2007 | Glassenberg et al. |
| 2007/0073160 A1 | 3/2007 | Imam |
| 2007/0106117 A1 | 5/2007 | Yokota |
| 2007/0106121 A1 | 5/2007 | Yokota et al. |
| 2007/0106122 A1 | 5/2007 | Yokota et al. |
| 2007/0106302 A1 | 5/2007 | Ortiz |
| 2007/0129603 A1 | 6/2007 | Hirsh |
| 2007/0137651 A1 | 6/2007 | Glassenberg et al. |
| 2007/0142709 A1 | 6/2007 | Martone et al. |
| 2007/0167686 A1 | 6/2007 | McGrath |
| 2007/0175482 A1 | 8/2007 | Kimmel et al. |
| 2007/0185383 A1 | 8/2007 | Mulhern et al. |
| 2007/0187626 A1 | 8/2007 | Gaska |
| 2007/0215162 A1 | 9/2007 | Glassenberg et al. |
| 2007/0226927 A1 | 10/2007 | Suzuki et al. |
| 2007/0234494 A1 | 10/2007 | Suzuki et al. |
| 2008/0011304 A1 | 1/2008 | Stewart et al. |
| 2008/0021273 A1 | 1/2008 | MacKin |
| 2008/0045801 A1 | 2/2008 | Shalman et al. |
| 2008/0098543 A1 | 5/2008 | Esquenet et al. |
| 2008/0105199 A1 | 5/2008 | Martin et al. |
| 2008/0141473 A1 | 6/2008 | Arai et al. |
| 2008/0142049 A1 | 6/2008 | Onishi et al. |
| 2008/0172033 A1 | 7/2008 | Keith et al. |
| 2008/0200761 A1 | 8/2008 | Schwartz et al. |
| 2008/0208000 A1 | 8/2008 | Schwarts et al. |
| 2008/0257355 A1 | 10/2008 | Roa et al. |
| 2008/0267688 A1 | 10/2008 | Busted |
| 2008/0281293 A1 | 11/2008 | Peh |
| 2009/0032016 A1 | 2/2009 | Law et al. |
| 2009/0044353 A1 | 2/2009 | Galantai et al. |
| 2009/0049627 A1 | 2/2009 | Kritzler |
| 2009/0062871 A1 | 3/2009 | Chin et al. |
| 2009/0099421 A1 | 4/2009 | Shalman et al. |
| 2009/0107503 A1 | 4/2009 | Baran |
| 2009/0118580 A1 | 5/2009 | Sun et al. |
| 2009/0119856 A1 | 5/2009 | Onishi |
| 2009/0143633 A1 | 6/2009 | Edmundson et al. |
| 2009/0143645 A1 | 6/2009 | Matthes |
| 2009/0149716 A1 | 6/2009 | Diao |
| 2009/0155770 A1 | 6/2009 | Brown et al. |
| 2009/0178681 A1 | 7/2009 | Bracken |
| 2009/0192355 A1 | 7/2009 | Mejia |
| 2009/0318757 A1 | 12/2009 | Singh |
| 2009/0320834 A1 | 12/2009 | Cuevas et al. |
| 2010/0010307 A1 | 1/2010 | Schramm |
| 2010/0036410 A1* | 2/2010 | Krolik .............. A61B 17/22032 |
| | | 606/194 |
| 2010/0069722 A1 | 3/2010 | Shalman et al. |
| 2010/0094090 A1 | 4/2010 | Mejia |
| 2010/0106102 A1 | 4/2010 | Ziebol |
| 2010/0113916 A1 | 5/2010 | Kumar |
| 2010/0186748 A1 | 7/2010 | Morejon |
| 2010/0199448 A1 | 8/2010 | Vazales et al. |
| 2010/0199999 A1 | 8/2010 | Vazales et al. |
| 2011/0023885 A1 | 2/2011 | Vazales et al. |
| 2011/0023886 A1 | 2/2011 | Vazales et al. |
| 2011/0023887 A1 | 2/2011 | Vazales et al. |
| 2011/0023888 A1 | 2/2011 | Vazales et al. |
| 2011/0048427 A1 | 3/2011 | Zachar |
| 2011/0197894 A1* | 8/2011 | Morejon .......... A61M 16/0463 |
| | | 128/207.14 |
| 2011/0290246 A1 | 12/2011 | Zachar |
| 2012/0180791 A1 | 7/2012 | Ciccone |
| 2013/0023729 A1 | 1/2013 | Vazales et al. |
| 2013/0030249 A1 | 1/2013 | Vazales et al. |
| 2013/0104884 A1 | 5/2013 | Vazales et al. |
| 2013/0324798 A1 | 12/2013 | Molnar et al. |
| 2013/0338467 A1 | 12/2013 | Grasse et al. |
| 2014/0012074 A1 | 1/2014 | Vazales et al. |
| 2014/0033455 A1 | 2/2014 | Vazales et al. |
| 2014/0090194 A1 | 4/2014 | Stadelman et al. |
| 2014/0090195 A1 | 4/2014 | Stadelman et al. |
| 2014/0090642 A1 | 4/2014 | Bagwell et al. |
| 2014/0246015 A1 | 4/2014 | Zachar et al. |
| 2014/0150782 A1 | 6/2014 | Vazales et al. |
| 2014/0200554 A1 | 7/2014 | Vitullo et al. |
| 2014/0283875 A1 | 9/2014 | Vazales et al. |
| 2015/0133864 A1 | 5/2015 | Zachar et al. |
| 2016/0193011 A1 | 7/2016 | Vazales et al. |
| 2016/0256646 A1 | 9/2016 | Vazales et al. |
| 2017/0065367 A1 | 3/2017 | Vazales et al. |
| 2017/0119494 A1 | 5/2017 | Vazales et al. |
| 2017/0258550 A1 | 9/2017 | Vazales |

FOREIGN PATENT DOCUMENTS

| | | |
|---|---|---|
| JP | 08-029699 | 2/1996 |
| JP | 2006-026344 | 2/2006 |
| WO | WO94/03226 | 2/1994 |
| WO | WO 2010/091309 A1 | 8/2010 |
| WO | WO 2011/097439 | 8/2011 |
| WO | WO2011/126812 | 10/2011 |
| WO | WO2012/131626 | 10/2012 |
| WO | WO2012/176112 | 12/2012 |
| WO | WO2013/030821 | 3/2013 |
| WO | WO2013/063520 | 5/2013 |
| WO | WO 2014/089028 A1 | 6/2014 |
| WO | WO2015/054102 | 4/2015 |

OTHER PUBLICATIONS

Pinciroli, Riccardo MD et al., Use of High-definition computed tomography to assess endotracheal tube luminal narrowing after mechanical ventilation, Anesthesiology, vol. 199, No. 1, Jul. 2013.

Mietto, Christina MD et al., Removal of endotracheal tube obstruction with a secretion clearance device; Sep. 2014, vol. 59, pp. e122-e126.

Boisvert, Andree-Anne et al., Microbial Biofilms in pulmonary and critical care diseases, Sep. 2016, vol. 13, No. 9, pp. 1615-1623.

Wilson Alison MD, et al., Trauma and Acute Care Surgery: Advanced endotracheal tube biofilm stage, not duration of intubation, is related to pneumonia, Apr. 2012, vol. 72, No. 4, pp. 916-923.

Danin, Pierre-Eric MD et al., Description and microbiology of endotracheal tube biofilm in mechanically ventilated subjects, Jan. 2015, vol. 60, No. 1, pp. 21-29.

El-Khatib, M.F. et al. Changes in resistances of endotracheal tubes with reductions in the cross-sectional area. European Journal of Anesthesiology Jan. 2008; vol. 25: pp. 275-279.

Product/Catalog of EndoSheath® Technology in 2 pages. Vision Sciences [retrieved in Mar. 2010; Publication Date Unavailable]; retrieved at www.visionsciences.com/SWAPPID/96/SubPageID/32590.

Product/Catalog of Endoscopy Systems and EndoSheath® Technologies—BRS-5000 Flexible Digital Video Bronchoscope in 2 pages. Vision Sciences [retrieved in Mar. 2010; Publication Date Unavailable]; retrieved at www.visionsciences.com/SWAPPID/96/SubPageID/38845.

Healthcare Professionals Distribution Pulmonology, Global in 3 pages. Vision Sciences [retrieved in Mar. 2010; Publication Date Unavailable]; retrieved at www.visionsciences.com/SWAPPID/96/SubPageID/39771.

Conti, G., et al., *A new device to remove obstruction from endotracheal tubes during mechanical ventilation in critically ill patients*, Intensive Care Medicine, 1994, pp. 573-576; vol. 20.

(56) References Cited

OTHER PUBLICATIONS

Wilson et al., *Increases in Endotracheal Tube Resistance Are Unpredictable Relative to Duration of Intubation.* Manuscript received Aug. 7, 2008. Chest, vol. 136, p. 1006-1013, Oct. 2009 Issue.

Product brochure in 2 pages For GlideScope® Cobalt of Verathon Medical, Inc., dated 2010.

Product brochure in 2 pages For Rescue Cath™ Complete Airway Management (CAM) Catheters of Omneotech, dated 2010.

Product information for CAM Endotrach Cath™ and CAM Rescue Cath™ catheter systems and other general information in 35 pages retrieved on Apr. 6, 2010 from the Omneotech website at www.omneotech.com.

Glass, Connie et al. Endotracheal Tube Narrowing After Closed-System Suctioning: Prevalence and Risck Factors. American Journal of Critical Care, Mar. 1999, vol. 8, No. 2, pp. 93-100.

Inglis, Timothy J.J. et al. Tracheal Tube Biofilm as a Source of Bacterial Colonization of the Lung. Journal of Clinical Microbiology, Sep. 1989, vol. 27, No. 9, pp. 2014-2018.

Kawati, Rafael MD et al. Peak Airway Pressure Increase Is a Late Warning Sign of Partial Endotracheal Tube Obstruction Whereas Change in Expiratory Flow Is an Early Warning Sign. Anesth Analg 2005;100:889-93.

Shah, Chirag MD et al. Endotracheal tube intraluminal volume loss among mechanically ventilated patients. Crit. Care Med 2004 vol. 32, No. 1, p. 120.

Van Surell, Catherine et al. Acoustic Method to Estimate the Longitudinal Area Profile of Endotracheal Tubes. Am J Respir Crit Care Med vol. 149, pp. 28-33, 1994.

Boque, MC et al. Endotracheal tube intraluminal diameter narrowing after mechanical ventilation: use of acoustic reflectomtry. Intensive Care Med. Dec. 2004;30(12):2204-9.

Apostolopoulou, Eleni Ph.D. et al. Incidence and Risk Factors for Ventilator-Associated Pneumonia in 4 Multidisciplinary Intensive Care Units in Athens, Greece. Respiratory Care, Jul. 2003, vol. 48, No. 7. pp. 681-688.

Seckel, Maureen. Implementing Evidence-Based Practice Guidelines to Minimize Ventilator-Associated Pneumonia. 2005.

Berra, Lorenzo et al. A clinical assessment of the Mucus Shaver: A device to keep the endotracheal tube free from secretions. Crit Care Med 2012 vol. 40, No. 1. pp. 119-124.

\* cited by examiner

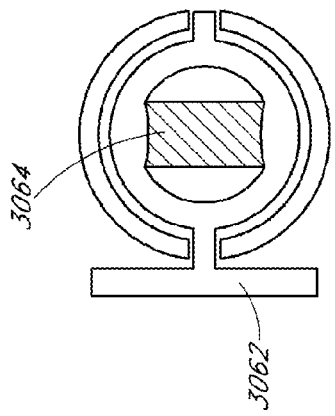
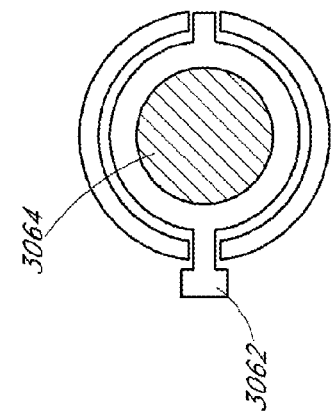
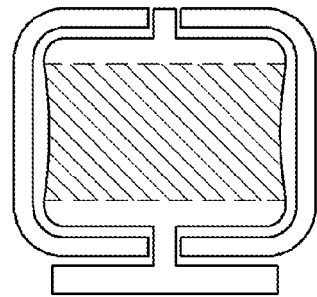
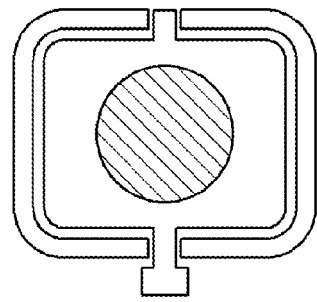
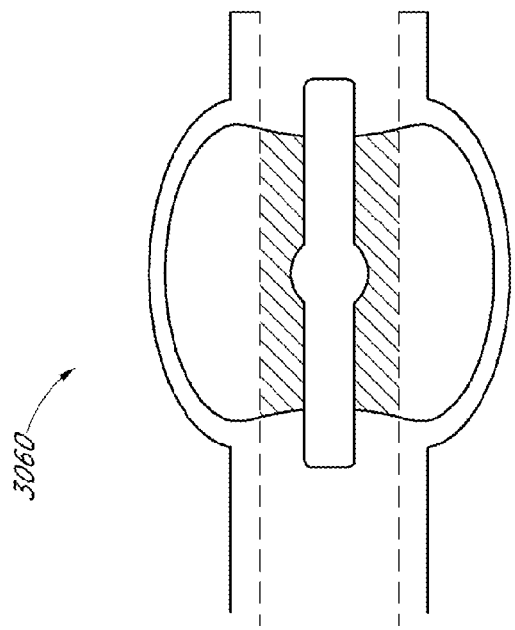
FIG. 2B
FIG. 2C
FIG. 2A

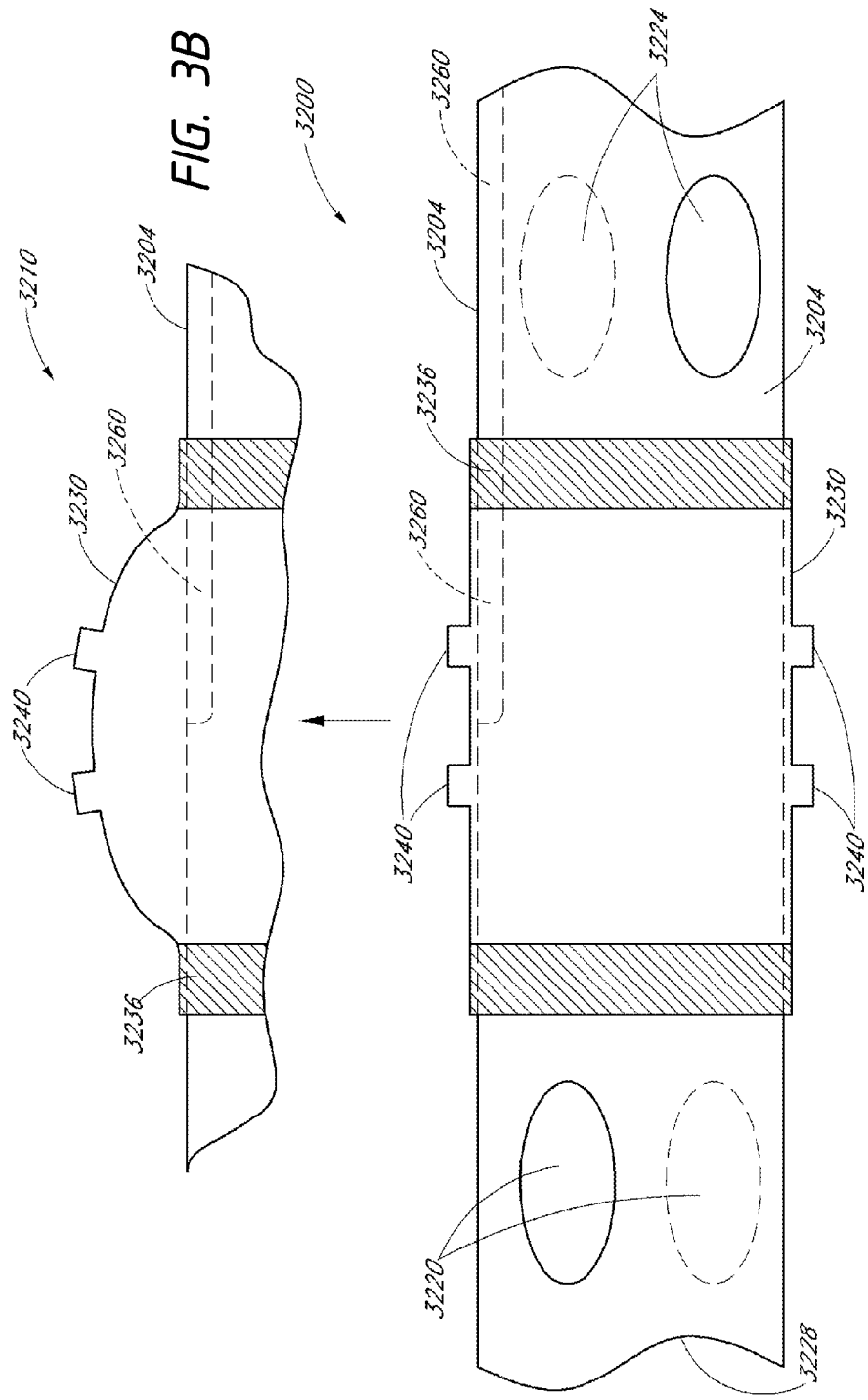

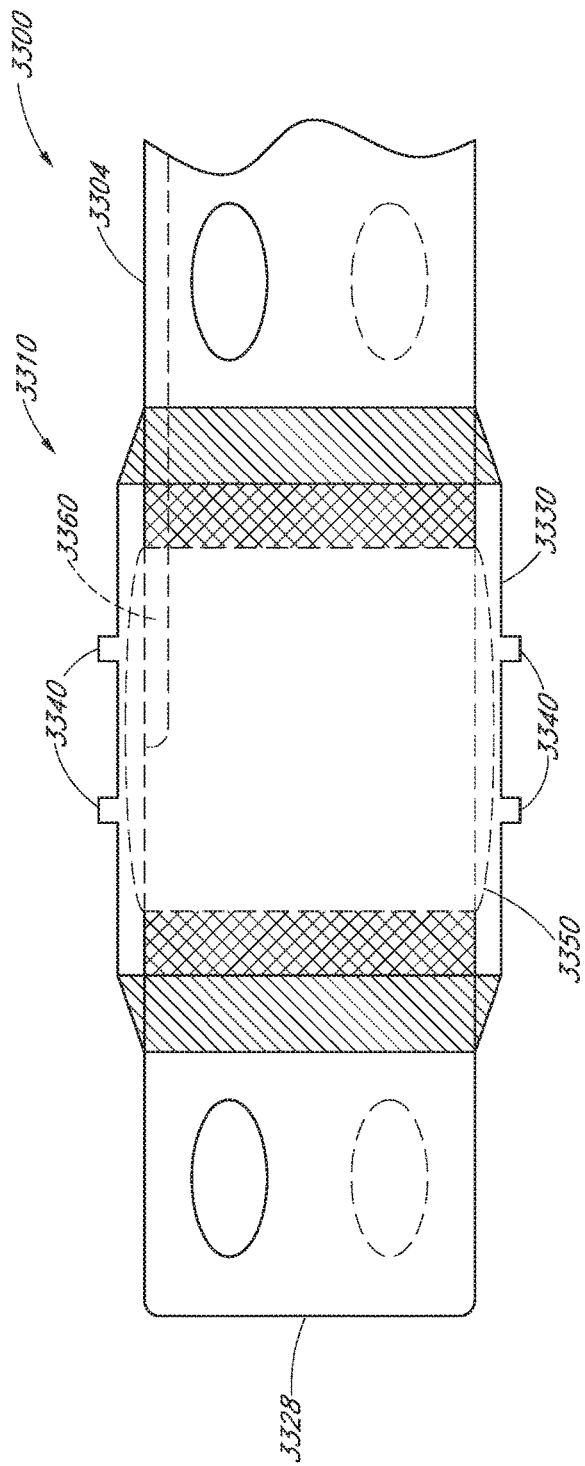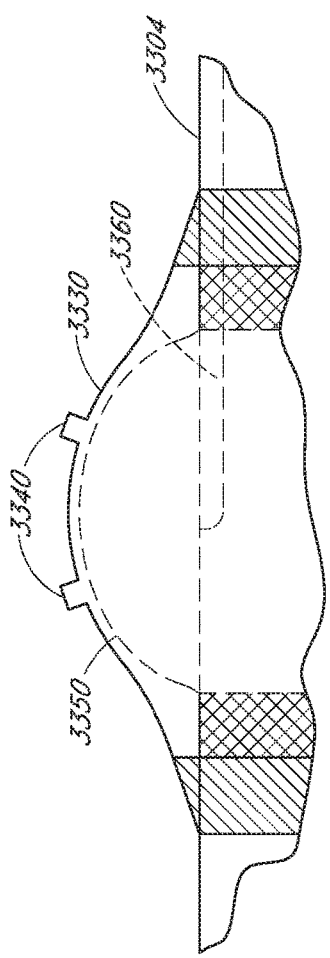
FIG. 4A
FIG. 4B

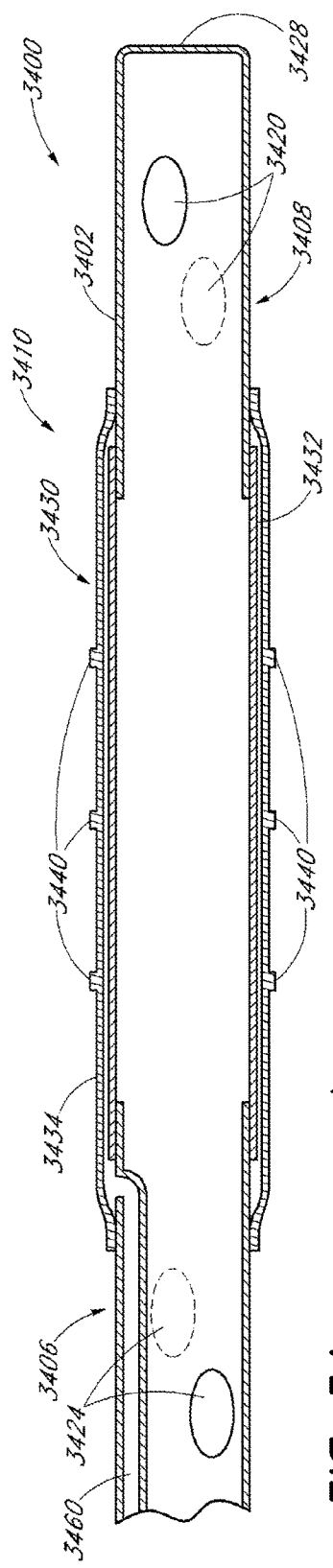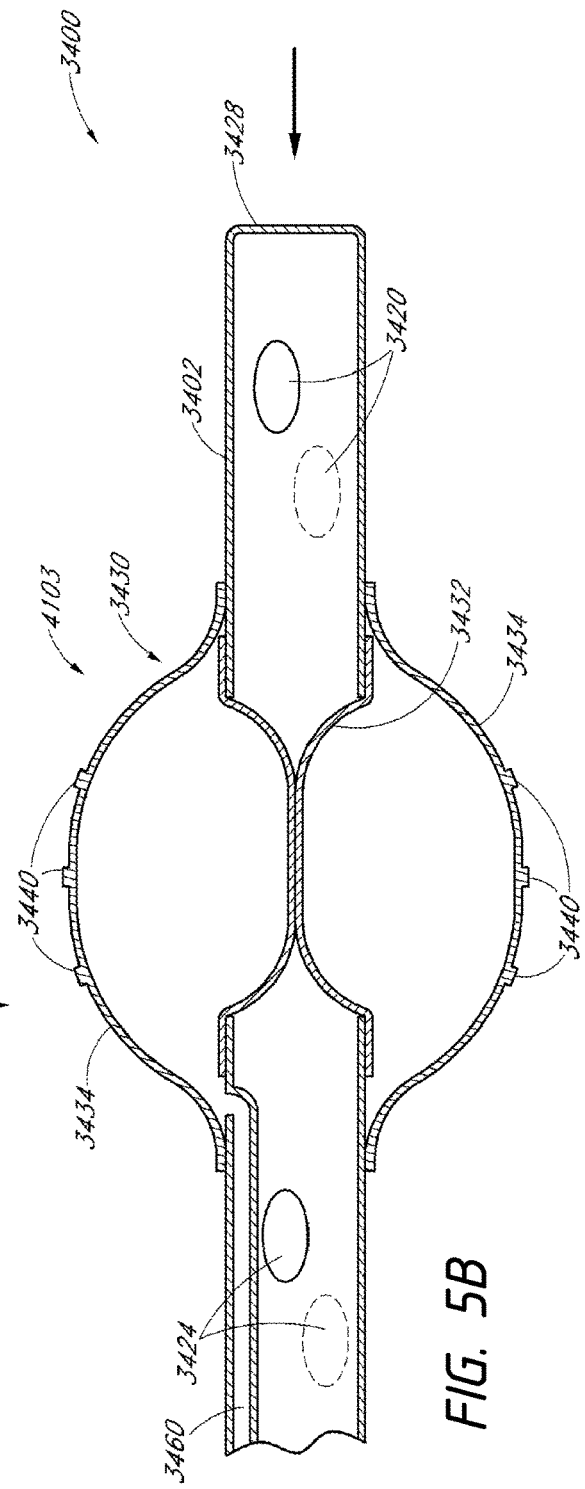
FIG. 5A
FIG. 5B

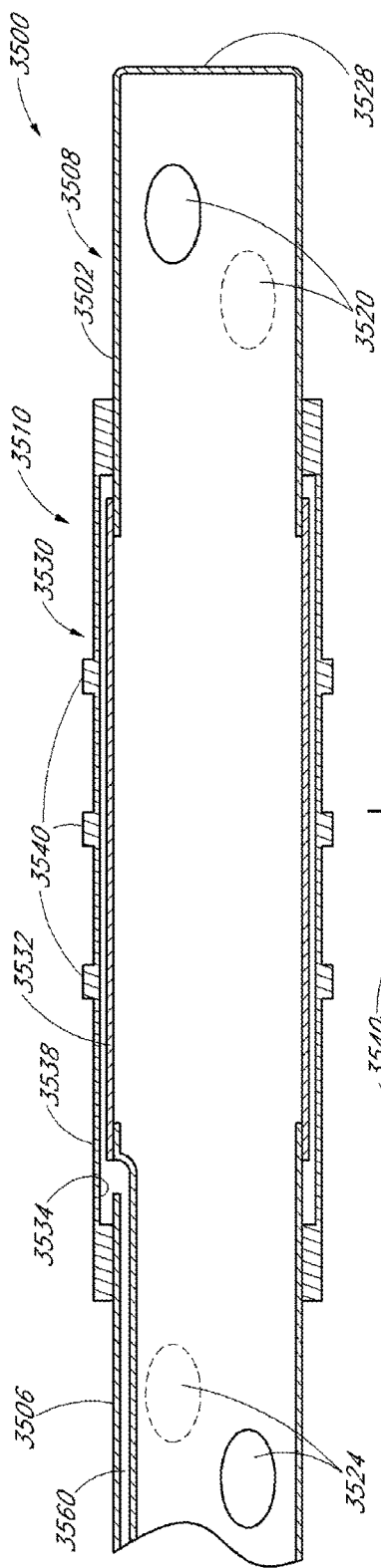
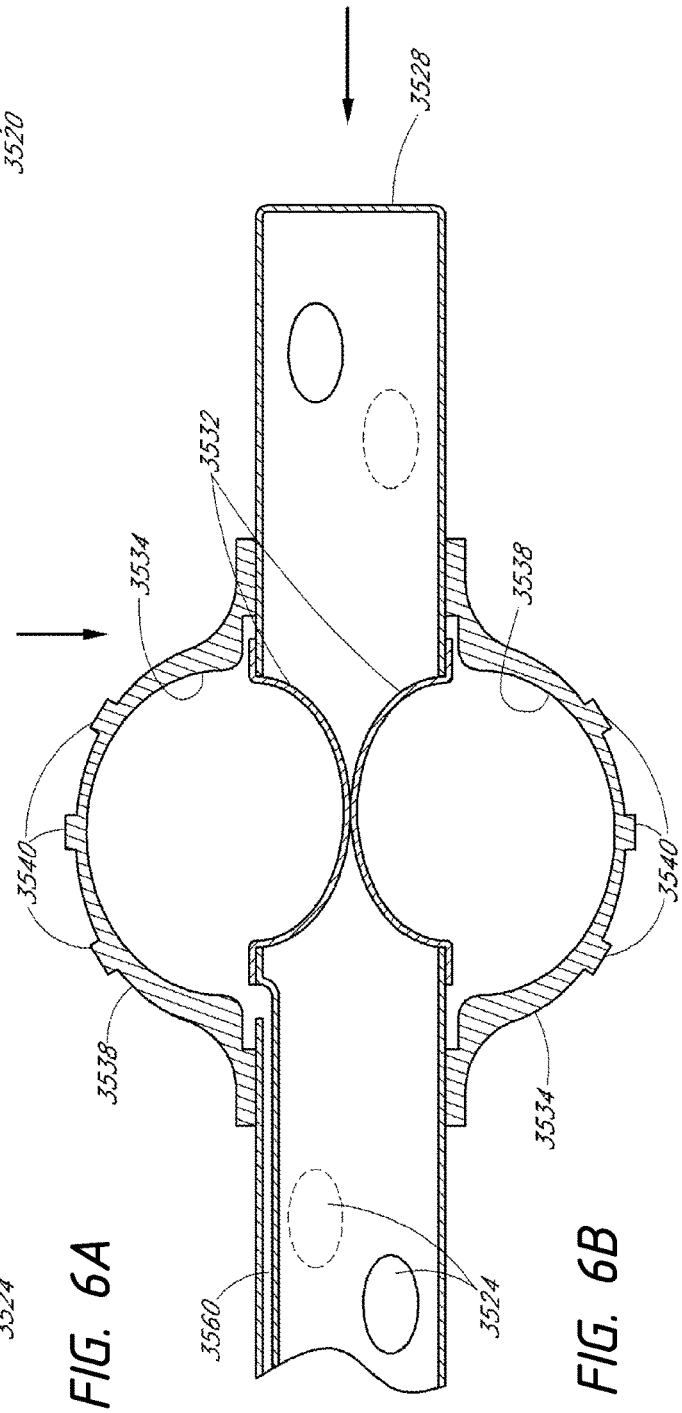
FIG. 6A
FIG. 6B

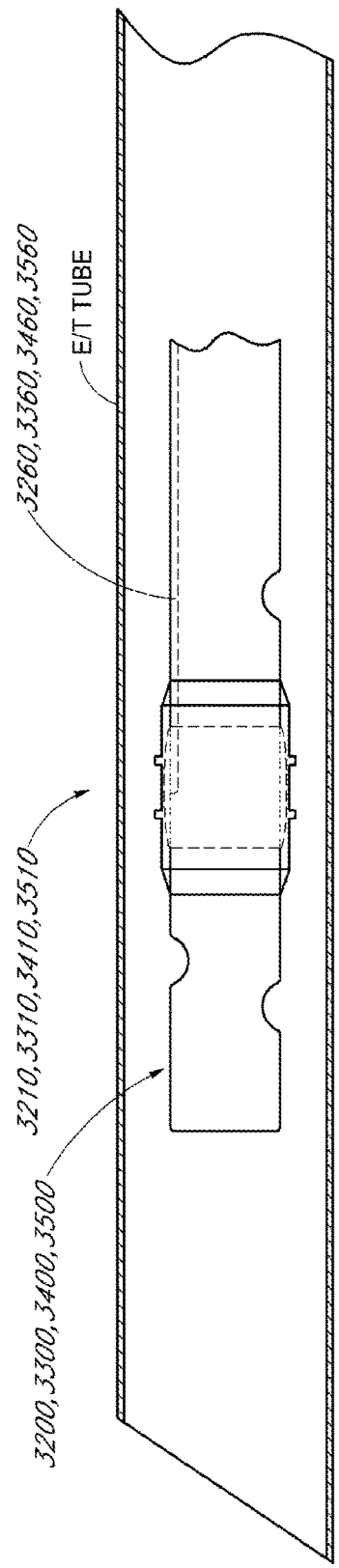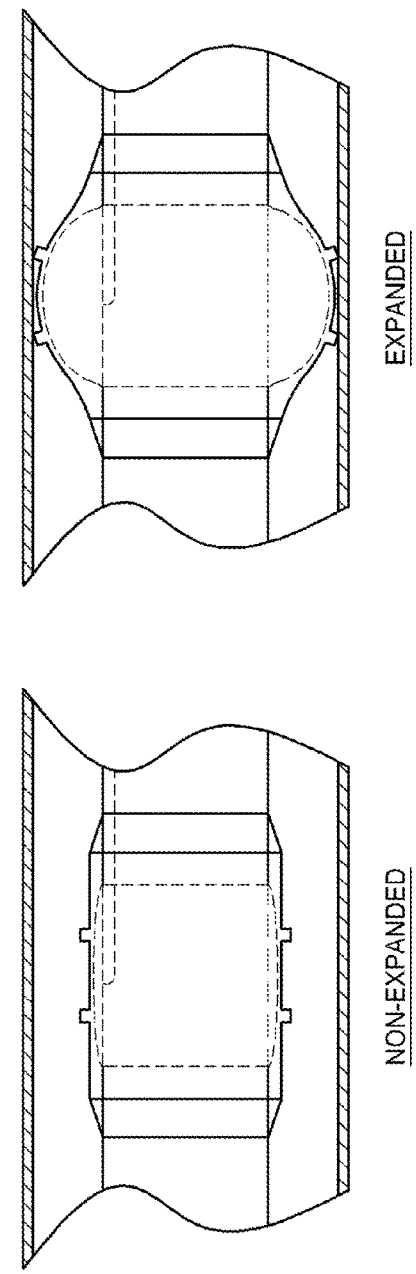
FIG. 7A
FIG. 7B NON-EXPANDED
FIG. 7C EXPANDED

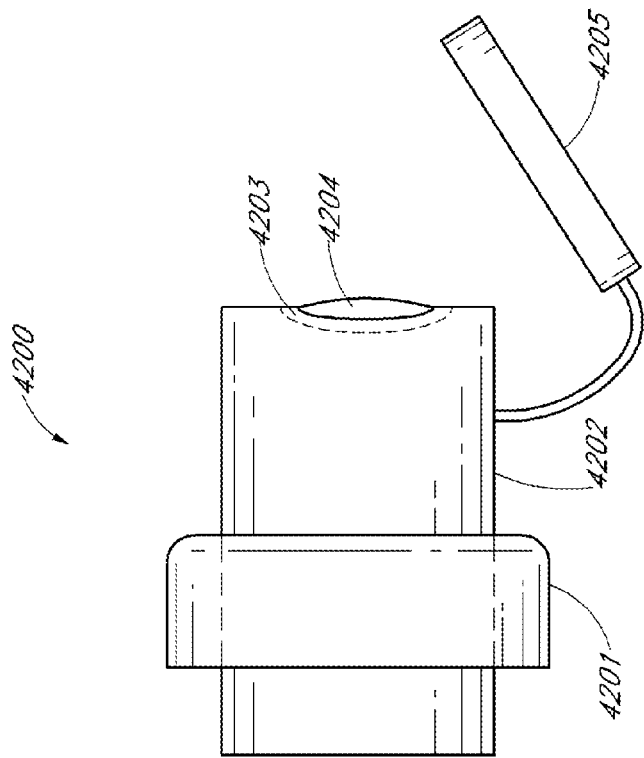
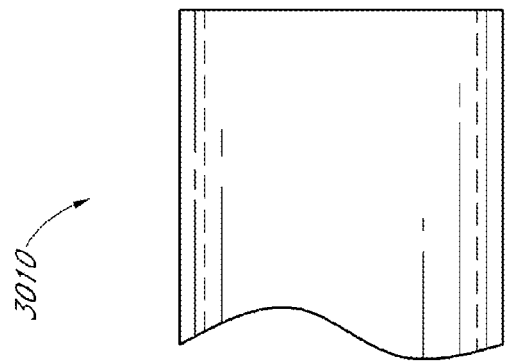
FIG. 12

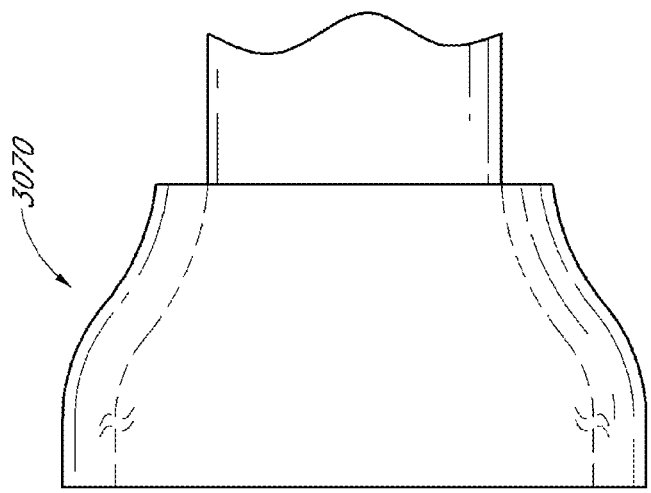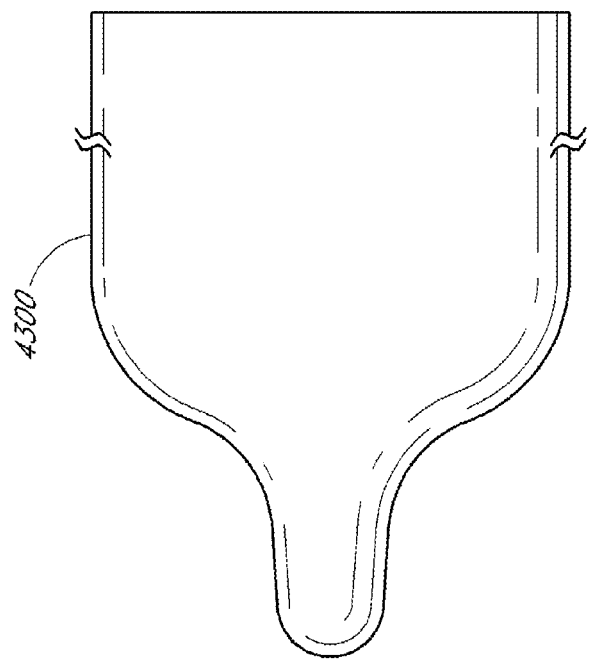
FIG. 13

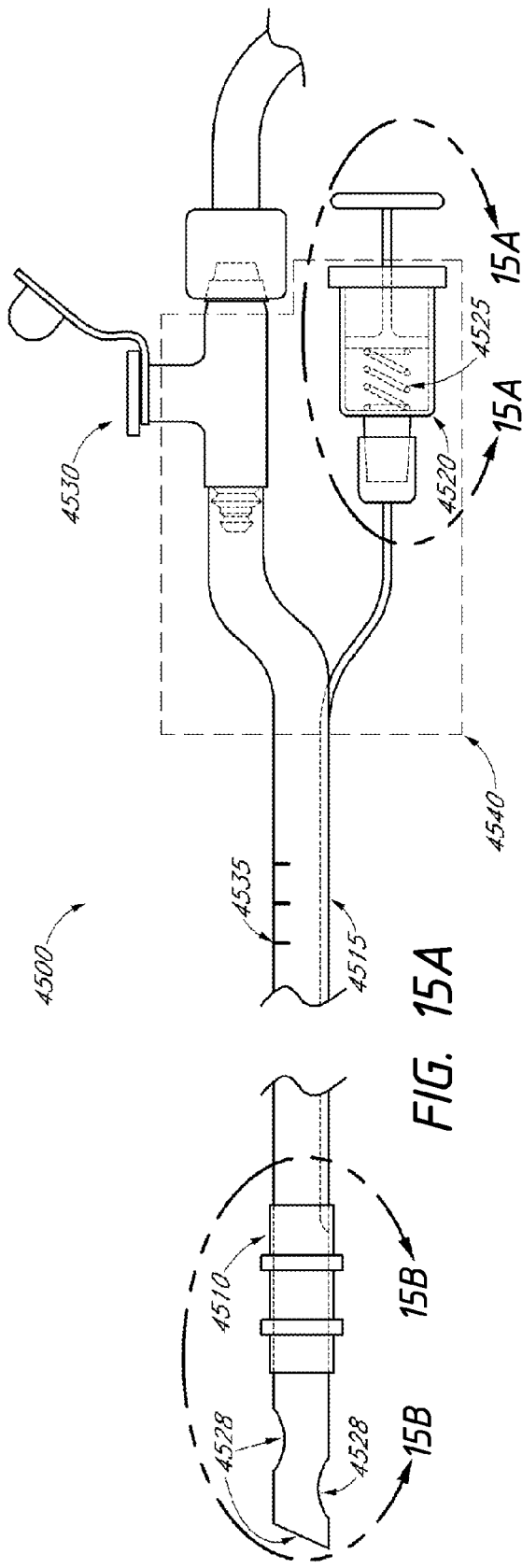
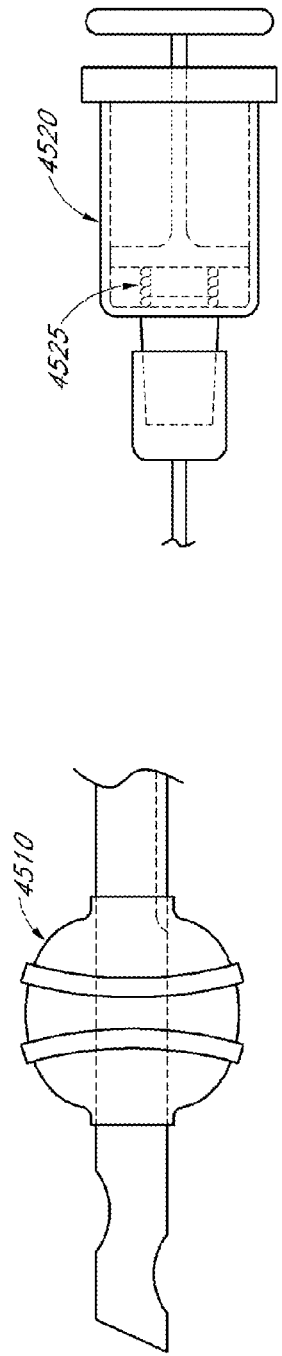
FIG. 15A
FIG. 15B
FIG. 15C

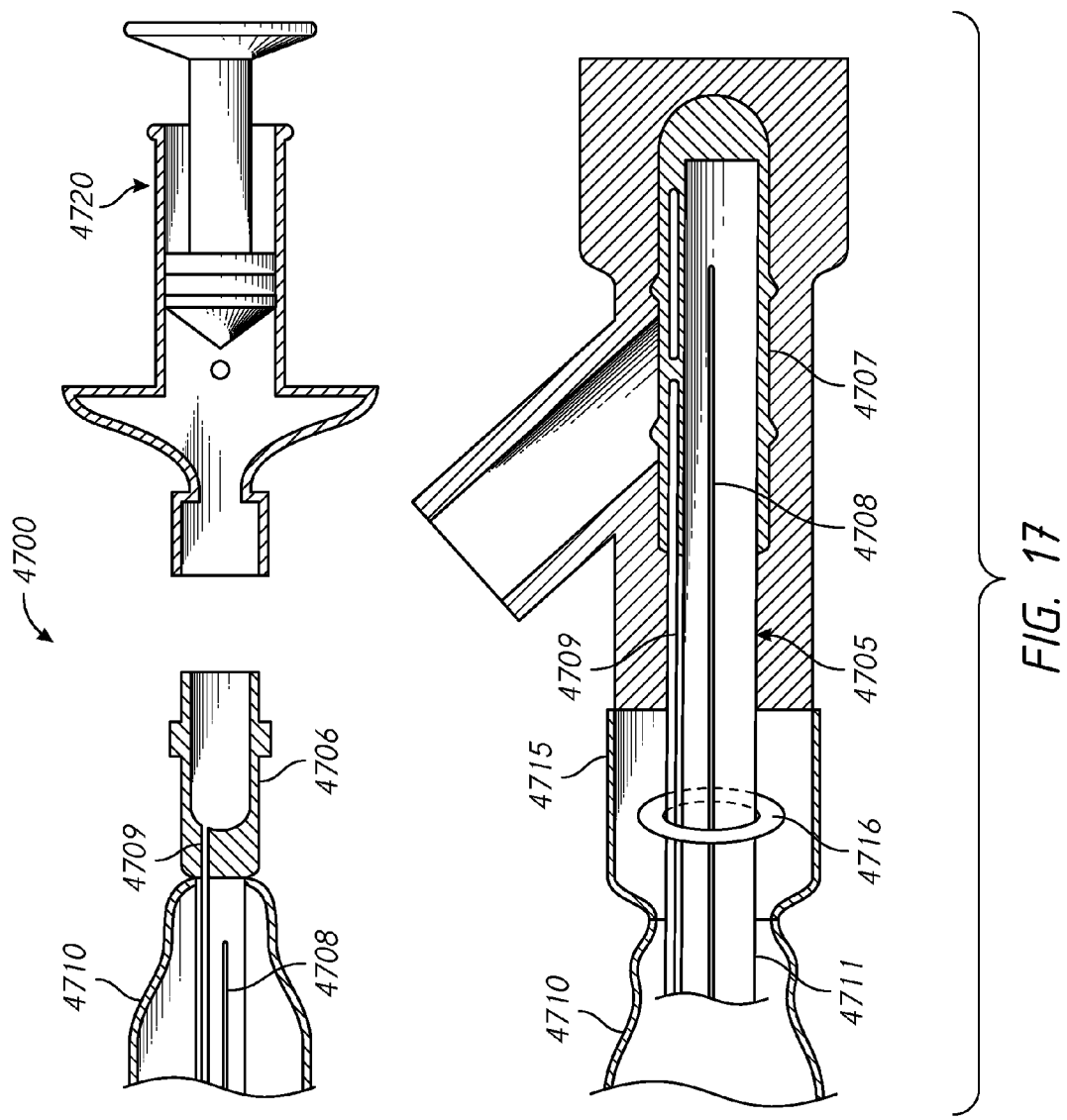

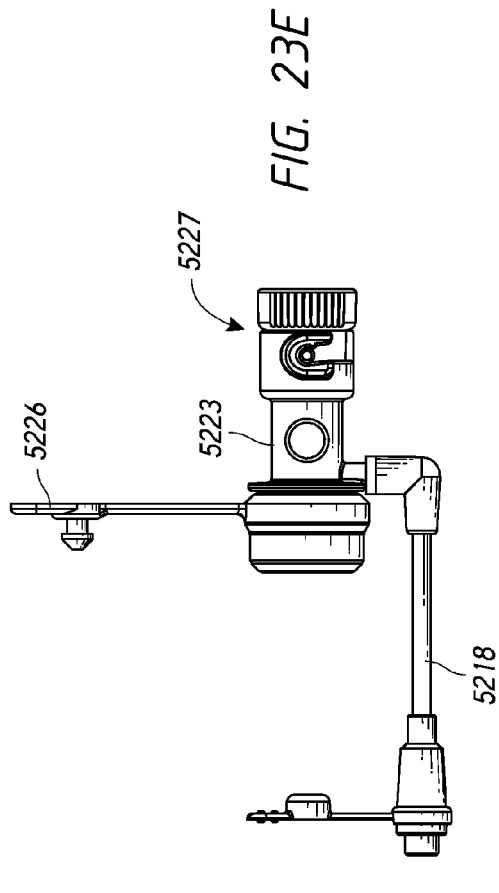
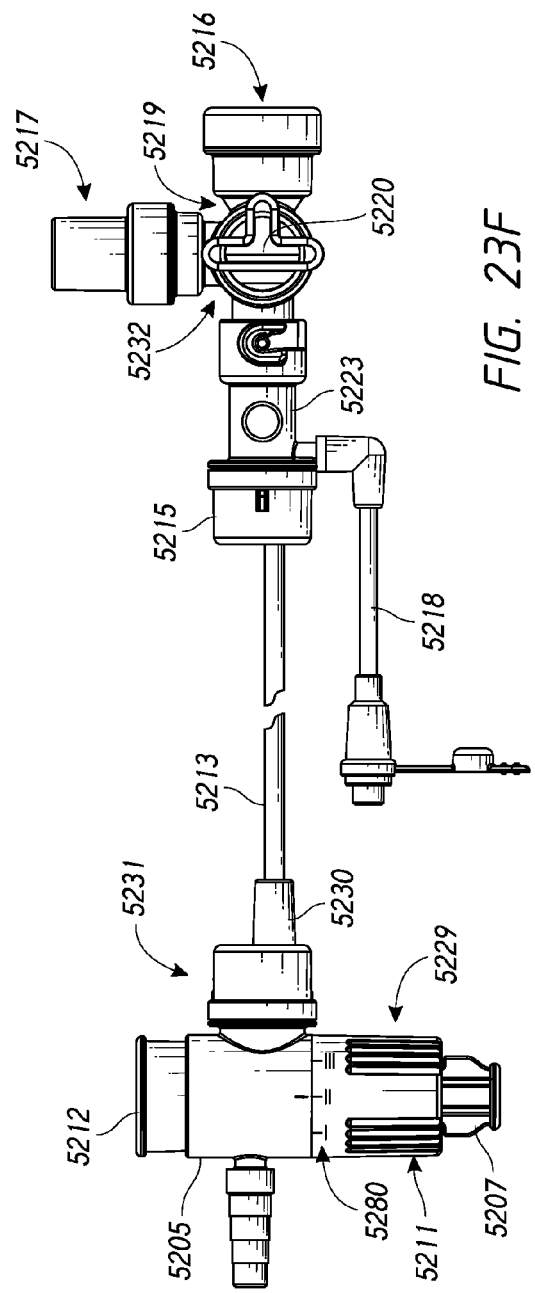

CLEANING DEVICES, SYSTEMS AND METHODS

RELATED APPLICATIONS

This claims priority under 35 U.S.C. § 119(e) to U.S. Provisional Application No. 62/007,328 filed Jun. 3, 2014, the entire content of which is hereby incorporated by reference herein.

This application is related to PCT Application No. PCT/US2013/072790, filed Dec. 3, 2013, published as WO 2014/089028 on Jun. 12, 2014, the entire content of which is hereby incorporated by reference herein.

FIELD

Embodiments disclosed herein relate generally to devices systems and methods for cleaning of body-inserted tubes (e.g., endotracheal tubes, chest tubes).

BACKGROUND

During an intubation procedure, endotracheal tubes can be placed in patients who are unable to effectively maintain life-sustaining ventilation and respiration on their own. An endotracheal tube is used in patient care to ensure a clear airway through the mouth, pharynx, and trachea into the lungs. Use of an endotracheal tube is appropriate when the integrity of the airway is, or may become, challenged due to trauma or pathology, or if a patient cannot otherwise breathe unaided. Often the endotracheal tube is coupled to a mechanical ventilator to aid the patient's respiration, and can be expected to remain in situ for an extended time until the patient is once again able to breathe on his or her own. The endotracheal tubes can be inserted within a patient's native airway for short periods of time (e.g., for a matter of hours during anesthesia for surgery) or the endotracheal tubes can remain in place to provide ventilator-assisted breathing for days or weeks.

The institution of mechanical ventilation can result in increased production of secretions within the patient's native airways and accumulation of those secretions within an artificial airway such as an endotracheal tube. The insertion of an endotracheal tube within the patient's trachea renders the normal cough mechanism for clearing of secretions ineffective, as the patient cannot transiently close the glottis to build up pressure in the airway that, when released, helps expel secretions. Also, the mucociliary system which helps transport secretions and debris from the tracheobronchial tree into the trachea for expectoration becomes ineffective in the sick, intubated patient. The secretions, therefore, can pool in dependent portions of the lung over time due to gravity and, if not removed in a timely manner, can result in ventilator-acquired pneumonia (VAP) or other undesired conditions or ailments. Closed suction systems may be coupled to the endotracheal tube and a suction catheter may be used to suction out the pooled secretions or other debris within the patient's native airways and/or the endotracheal tube. Intraluminal volume loss attributable to the accumulation of secretions on the interior wall of endotracheal tubes is not prevented by standard suctioning treatment. Secretion accumulation can lead to life-threatening occlusion of the endotracheal tube or at least increased work of breathing, which may result in increased difficulty in weaning, and prolonged mechanical ventilation and intensive care unit stay. Additionally, secretion accumulation on the inside of the endotracheal tube leads to colonization with potentially pathological organisms and this colonization is likewise implicated in the development of VAP.

Bronchoscopes are typically used to visualize the patient's airways. In order to insert the bronchoscopes within the patient's mouth and into (and possibly through) the endotracheal tube, the standard closed suction system must be removed, thereby at least temporarily removing the patient from the ventilator, which may not be feasible for patients with high ventilatory requirements. In addition, due to the large diameter of most bronchoscopes, air travel through the endotracheal tube may be substantially blocked during the visualization procedure.

SUMMARY

In accordance with several embodiments, a closed suction system module is provided. In one embodiment, the closed suction system module comprises a coupling member configured to couple to a suction port of a multi-port manifold or endotracheal tube adapter (e.g., dual-port or tri-port adapter). In one embodiment, the closed suction system module comprises a suction catheter configured to clean the interior surfaces of body-inserted tubes or artificial airways (alone or in addition to suctioning natural airways or portions of the respiratory tract or other body lumens). The suction catheter may comprise a cleaning portion at a distal portion of the suction catheter (e.g., near the distal end or tip of the suction catheter). In some embodiments, the cleaning portion comprises at least one deployable (e.g., expandable, inflatable) cleaning member (e.g., balloon, sleeve, wiper). The expandable cleaning member may have a smooth, regular profile. In some embodiments, the expandable cleaning member comprises one or more rings, shavers or other removal members. The rings, shavers or other removal members may comprise one or more shearing or squared (or substantially squared) edges or may comprise a smooth contact surface with rounded edges.

In some embodiments, the closed suction system module comprises an activation member configured to cause deployment (e.g., expansion, inflation) of the cleaning member and to control suction through the suction catheter. The closed suction system module may comprise multiple activation members, each configured to activate or control different functions. The one or more activation members may be components of a control unit positioned at or near the proximal end of the suction catheter (e.g., on or within a proximal housing). In some embodiments, a first activation member is configured to control suction through the suction catheter and a second activation member is configured to cause simultaneous expansion of the expandable cleaning member and initiation of suction through the suction catheter. In various embodiments, the expandable cleaning member is pneumatically expandable or mechanically expandable. In some embodiments, at least one activation member is configured to compress a fluid or gas reservoir in fluid communication with the expandable cleaning member, thereby causing the expandable cleaning member to expand (e.g., inflate). The activation members may comprise plungers, syringes, buttons or other devices configured to be activated by a single actuation motion with a single press or touch of a finger. The control unit may be configured to be held and controlled using a single hand.

In some embodiments, upon expansion of the expandable cleaning member, at least a portion of the expandable cleaning member is configured to contact an interior surface of a body-inserted tube (e.g., endotracheal tube) such that, when the suction catheter is withdrawn from the body-inserted tube, biofilm (e.g., debris or secretions) collected on the interior surface is removed by the expandable cleaning member. In one embodiment, the closed suction system module comprises a flexible sheath configured to, during use, prevent exposure of a portion of the suction catheter outside of the body-inserted tube to an external environment.

In accordance with several embodiments, the closed suction system module is coupled to a manifold or endotracheal tube coupling adapter to form an endotracheal tube cleaning system. The manifold or endotracheal tube coupling adapter may comprise multiple ports, such as a ventilator port, a suction port and a distal port. The distal port may be configured to directly or indirectly (e.g., via a universal endotracheal tube connector) couple to an endotracheal tube. A coupling member of the closed suction system module may be configured to couple to the suction port of the manifold or endotracheal tube coupling adapter. In some embodiments, the endotracheal tube adapter comprises a viewing window for viewing of markings (e.g., centimeter markings) on the suction catheter indicative of depth of insertion within the endotracheal tube, such that the suction catheter may be advanced to or slightly distal to the distal end (e.g., distal tip) of the endotracheal tube. The markings on the suction catheter may correspond to similar markings on the endotracheal tube.

In some embodiments, the cleaning member comprises a lubricant (e.g., a SURGILUBE lubricant) and/or a bactericide or antibacterial agent (e.g., chlorhexidine). The cleaning member alone, the suction catheter alone, or both the suction catheter and the cleaning member may be treated so that a bonded or integral lubricious coating (e.g., parylene) may facilitate insertion of the suction catheter and withdrawal of the suction catheter and deployed cleaning member(s). In one embodiment, the bactericide is activated by photodynamic means. In some embodiments, the suction catheter comprises at least a first suction port distal to the cleaning portion and at least a second suction port proximal to the cleaning portion. In some embodiments, the suction port or ports are only distal to the cleaning portion. In some embodiments, the suction port or ports are only proximal to the cleaning portion. In embodiments where the suction port or ports are only proximal to the cleaning member, the distal tip of the suction catheter may be closed or sealed off. The first and second suction ports may be dynamically controlled to allow suction distal and/or proximal to the cleaning portion when a distensible or expandable member of the cleaning portion is expanded. In some embodiments, suction is applied only to the suction port(s) proximal to the cleaning portion while the suction catheter is being withdrawn from an endotracheal or other body-inserted tube, thereby facilitating removal of biofilm (e.g., secretions, debris) that has been removed by the cleaning member of the suction catheter without risking adverse side effects due to removal of too much air from the lungs, which could occur if the distal suction ports were suctioning while the cleaning member is expanded within the body-inserted tube.

In accordance with several embodiments, a device configured to clean a body-inserted tube is provided. In one embodiment, the device comprises a suction catheter configured to clean an interior surface of a body-inserted tube. In some embodiments, the suction catheter comprises a cleaning portion located at or near a distal end of the suction catheter and a controller having one or more activation members located along a proximal end of the suction catheter. In one embodiment, the cleaning portion comprises at least one cleaning member. The at least one cleaning member may be configured to be radially expanded (e.g., mechanically or pneumatically) upon actuation of the activation member(s). In one embodiment, the controller is configured to selectively expand the at least one cleaning member and/or to control suction through the suction catheter. In one embodiment, at least one suction port is disposed proximal of the at least one cleaning member along a length of the suction catheter. In one embodiment, the at least one suction port is distal of the at least one cleaning member. The at least one suction port may be in fluid communication with a lumen of the suction catheter and, in some embodiments, is configured to suction at least a portion of the removed biofilm from the body-inserted tube along a proximal side of the cleaning portion. In one embodiment, the at least one cleaning member comprises at least one inflatable balloon and an outer sleeve positioned along an exterior of the at least one inflatable balloon. In one embodiment, the at least one cleaning member is positioned along (e.g., adhered to or placed over) the outer sleeve. In one embodiment, the at least one inflatable balloon comprises two inflatable balloons. The balloon(s) and suction catheter may be formed (partially or entirely) of silicone material having the same or similar durometer. The balloon and/or outer sleeve may be joined to each other and/or to the suction catheter using silicone adhesive.

In accordance with several embodiments, a method for cleaning an endotracheal tube and distal airways with a single cleaning device without removing a patient from a ventilator is provided. In one embodiment, the method comprises coupling an endotracheal tube adapter or manifold to the endotracheal tube. In one embodiment, the endotracheal tube adapter or manifold comprises multiple ports, such as a distal coupling port, a ventilator port, and a suction port. The method may further comprise connecting a coupling member of a closed suction system or module to the suction port of the endotracheal tube adapter or manifold. In one embodiment, the closed suction system or module comprises a suction catheter and a flexible sheath configured to enclose the suction catheter when it is withdrawn from the endotracheal tube. In some embodiments, the suction catheter comprises an expandable cleaning member and a control unit (e.g., at least one activation or actuation member) configured to control expansion and retraction of the expandable cleaning member and to control suction through the suction catheter.

In one embodiment, the method further comprises coupling a ventilator to the ventilator port of the endotracheal tube adapter or manifold and inserting a distal end of the suction catheter through at least a portion of an endotracheal tube. In one embodiment, the method comprises activating the at least one activation member with a single actuation motion to cause expansion of the expandable cleaning member to an expanded position. Upon expansion, the expandable cleaning member is configured to contact an interior surface of the endotracheal tube so that the endotracheal tube can be at least partially cleaned when the cleaning member is moved relative to the endotracheal tube. In one embodiment, the method comprises at least partially withdrawing the suction catheter from the endotracheal tube. The flexible sheath may be configured to shield the suction catheter from an outside environment between consecutive endotracheal tube cleaning or suction events while air is continuously supplied to the patient via a ventilator.

In some embodiments, the method comprises suctioning distal airways of a patient using the suction catheter. In one embodiment, the method comprises cleaning a distal tip of the suction catheter through an irrigation port of the endotracheal tube adapter. In some embodiments, the method comprises collecting a portion of the removed biofilm for microbiologic evaluation. The method may comprise identifying a type of bacteria present within the removed biofilm (such as by polymerase chain reaction, infrared light detection, or other real-time or substantially real-time diagnostic or evaluation methods).

In accordance with several embodiments, a visualization device module configured to provide visualization of a patient's airways within a closed suction environment is provided. In one embodiment, the visualization device module comprises a distal coupling member configured to couple to the endotracheal tube adapter. In one embodiment, the visualization device module comprises a visualization device sized and configured to extend from a mouth of a patient to distal portions of the respiratory tree of a patient (e.g., bronchoscope). In one embodiment, the visualization device module comprises a flexible sleeve coupled to the distal coupling member and extending proximally therefrom to enclose the visualization device when the visualization device is outside of the patient, thereby isolating the visualization device from exposure to outside air or external contamination. In one embodiment, the visualization device (e.g., flexible fiber optic scope) may be introduced via an angled irrigation port of a closed system manifold comprising a seal or mechanical coupling. In some embodiments, the visualization device includes a suction lumen, a visualization lumen, and/or an irrigation lumen.

In accordance with several embodiments, a method is provided for removal and collection of secretions, debris, biofilm or bacteria within a body-inserted tube using a suction catheter having at least one wiper or shaver to return the body-inserted tube to a nominal condition. The suction catheter may be a component of a closed suction system module that is coupled to the body-inserted tube. In several embodiments, the at least one wiper or shaver is disposed on, and/or a component of, an expandable cleaning portion near the distal end of the suction catheter. The expandable cleaning portion may be inflatable (e.g., pneumatically expandable) or mechanically expandable. In some embodiments, the at least one wiper or shaver comprises a lubricant (e.g., a SURGILUBE® lubricant) and/or a bactericide or anti-bacterial or anti-microbial agent (e.g., chlorhexidine). The suction catheter with the expandable cleaning portion may be used one, two, three, four, or more times a day to prevent the accumulation of secretions and biofilm in the body-inserted tube.

In some embodiments, the suction catheter has an outer diameter that is less than 70% (e.g., 20%, 25%, 30%, 35%, 40%, 45%, 50%, 55%, 60%, 65%) of the inner diameter of the body-inserted tube (e.g., endotracheal tube, chest drainage tube, urinary catheter). The outer cross-sectional dimension of the suction catheter may be sized such that the suction catheter does not significantly compromise airflow during its insertion, or during deployment and removal. In one embodiment, the outer diameter of the suction catheter is less than 50% of the inner diameter of the body-inserted tube. In one embodiment, the outer diameter of the suction catheter is no larger than 70% of the diameter of the lumen of the body-inserted tube.

In one embodiment, the suction catheter comprises a channel for insertion of a visualization device (e.g., fiber-optic scope). The visualization device may be inserted into the channel and used for visualization of the materials obstructing the body-inserted tube. In some embodiments, the visualization device may be communicatively coupled to an image capture system. The image capture system may include a graphic user interface. In some embodiments, a single touch of a user input on the graphic user interface enables the capture of a still image or a movie of the images that are being viewed by the visualization device. In some implementations, the images are communicated to a physician in a remote location (not at the bedside), thereby facilitating remote care. The images may be of a suitable quality that allows the physician to perform a diagnostic evaluation and bill for the images and related diagnostic care. Visualization may be used to assess the patency of the body-inserted tube, the position of the body-inserted tube and status of the surrounding airway, and/or the level and/or type of bacteria (or other microorganisms or materials) present within the body-inserted tube.

The body-inserted tube may be positioned within an airway (e.g., trachea) or other body lumen (e.g., blood vessel). In some embodiments, the material removed by the suction catheter is collected for the purpose of obtaining a culture to assess the bacteria in the body-tube, thereby allowing a clinician to prescribe specific antibiotics based on the bacteria present. In some embodiments, the culture can be obtained and/or the antibiotics may be administered between 24 to 48 hours after insertion of the body-inserted tube for early detection and treatment of hospital acquired infections.

In accordance with several embodiments, a "partially closed system" is provided in which any breaks or exchanges in the ventilatory circuit are performed in a manner to minimize infection, with superior ease of use and infection control for the purpose of introducing medicines, viewing tools or cleaning tools.

In some embodiments, the manifold or endotracheal tube adapter comprises one or more coupling members. For example, the manifold can comprise a coupling member having one or more inlet ports. In one embodiment, the manifold comprises a main in-line device insertion port and one or more branched inlet ports. The branched inlet ports can comprise, for example, an oxygen port configured to connect to an oxygen line or ventilator and an access port configured to receive a stylet (e.g., a malleable obturator). In some embodiments, the coupling assembly is a manifold of a closed system device comprising an endotracheal tube connection, ventilator connection, irrigation port(s), a selectable fluid path (e.g., stopcock) and a coupling for a suction catheter, cleaning member, bronchoscope or other such device that may be introduced into the endotracheal tube. The irrigation port(s) may be angled to allow small diameter (e.g., 1-2 mm outer diameter) scopes to enter the system without disconnecting any other coupling.

In some embodiments, the cleaning member can be mechanically expanded (e.g., using an actuation assembly) or is self-expanding and the cleaning device does not comprise an inflation channel. In some embodiments, the cleaning device comprises a control handle configured for one-handed operation of the cleaning device. In some embodiments, the cleaning device provides an "all-in-one" device configured to provide visualized cleaning of body-inserted medical tubes (e.g., endotracheal tubes) and visualized suctioning of distal airways (e.g., portions of lungs).

In some embodiments, the cleaning device comprises a scope retention assembly configured to exert a static backward force on a visualization scope inserted within the visualization channel to press the visualization scope against a window at the distal end of the visualization channel, thereby advantageously reducing glare and providing protection for the scope. In some embodiments, the scope retention assembly comprises an elastomeric sleeve and a scope retention member configured to interact with a locking or retention member coupled to the visualization scope to exert the static backward force. In some embodiments, the lens of the visualization scope is kept in constant contact or near contact with the viewing window of the visualization tube, or sheath, using the scope retention assembly.

According to several embodiments, a self-contained distal airway cleaning system for removing debris from one or more distal airways of a patient comprises a suction catheter comprising a main suction lumen and a pre-bent, distal end configured to facilitate steering of the suction catheter within the distal airways of the patient. The system can further comprise a standalone suction control unit configured to control a level of suction applied to the suction catheter. The system can also comprise an irrigation channel defined within the main suction lumen of the suction catheter, the irrigation channel configured to deliver fluid to the distal airways of the patient, and a standalone irrigation control unit configured to control the delivery of fluid to the distal airways of the patient. In some embodiments, the system comprises a control handle configured for one-handed control of the suction control unit and the irrigation control unit. The irrigation channel (or other optional delivery channel) may also be used to deliver medicaments, biologically active agents and/or other compounds to a patient. Ultraviolet (e.g., UVC), germicidal and/or antimicrobial treatment may be incorporated in several embodiments. Therapeutic modalities are included in some embodiments, including but not limited to, radiofrequency, ultrasound, laser, microwave, heat, and cryotherapy, or combinations thereof. In one embodiment, the therapy is used to effect fibrosis, stiffening and/or ablation.

According to some embodiments, a method for cleaning one or more airways of a patient comprises providing a cleaning device configured to remove biofilm from an interior wall of an endotracheal tube. In one embodiment, the cleaning device includes an elongate body, an expandable structure, a removal member, and an actuation assembly. In one embodiment, the removal member comprises a generally smooth outer surface that contacts the inner surface of the endotracheal tube. The method additionally includes inserting the cleaning device into the endotracheal tube while the expandable structure is in a collapsed position and actuating the expandable structure using the actuation assembly to expand the expandable structure from the collapsed position to an expanded position, thereby expanding the removal member to contact the biofilm. In some embodiments, the method further comprises withdrawing the cleaning device from the endotracheal tube while maintaining contact between the removal member and the biofilm to dislodge said biofilm and removing the cleaning device from the patient. In several embodiments, the method comprises providing a suction catheter system having a main suction lumen and distal end configured to facilitate steering of the suction catheter within one or more distal airways of the patient. In one embodiment, the suction catheter system comprises a suction control unit configured to control a level of suction applied to the suction catheter. The method additionally includes activating the suction control unit so as to provide suction through the main suction lumen to remove debris from one or more airways of the patient. In one embodiment, the suction catheter system is inserted into and removed from the one or more distal airways of the patient either before or after the cleaning device is used to remove biofilm from the interior wall of the endotracheal tube.

According to some embodiments, a method of removing biofilm (e.g., debris) from one or more airways of a patient includes providing an airway cleaning device comprising a steerable suction catheter having at least one suction lumen defined therein and a distal end configured to facilitate steering of the suction catheter within the airways of the patient. In one embodiment, the airway cleaning device comprises a visualization channel configured to removably receive a visualization scope having imaging and light delivery elements, wherein the visualization channel comprises a transparent window at its distal end. In several embodiments, the method of removing biofilm (e.g., debris) further comprises inserting the airway cleaning device within an airway of the patient, positioning the distal end of the airway cleaning device within a target region of a patient's airway and inspecting the target region for accumulated debris using the visualization scope positioned within the visualization channel. In some embodiments, the method additionally includes activating a suction force within the suction lumen of the suction catheter to remove accumulated debris from the airway of the patient and removing the airway cleaning device from the patient's distal airway.

According to some embodiments, a kit (e.g., system or collection of items for a common purpose) for removing biofilm (e.g., debris) that has collected within one or more airways (e.g., native airway, oral cavity, nasal passages, pharynx, larynx, trachea, and/or any portion of the lungs, including any of the branches of the tracheobronchial tree, endotracheal tube, etc.) of a patient is provided. The term "kit" as used herein should be given its ordinary meaning and should include any system, grouping and/or collection of devices, systems, components, features, materials and/or the like provided for a common goal. In one embodiment, the kit comprises one or more of the following, depending on the needs or clinical situations handled by the patient care facility: an endotracheal tube (e.g., having standard or non-standard size, shape, etc.), an endotracheal tube with built-in visualization channel, another type of endotracheal tube or other body-inserted tube or device, a visualization member (e.g., a visualization scope), a visualization device (e.g., tube or sheath) adapted to receive a visualization member, an endotracheal tube cleaning device, a tongue elevator, a suction catheter having an integrated tube cleaning member, a closed suction system or module, accessory caps, biofilm collection adapters, tubular extensions, an airway cleaning device and/or any other system, device or component. The kit can further comprise instructions for using the various devices, components and/or other features of the kit for a particular cleaning protocol or procedure. For example, such instructions for use can include details regarding the order in which the devices, systems or other components are used, the duration of use and/or the like.

According to several embodiments of the invention, a kit is provided that comprises a visualization device, a visualization scope configured to be removably inserted within the visualization device, a cleaning device and one or more removable manifolds or adapters. The cleaning device can comprise an endotracheal tube cleaning device, a suction catheter or a distal airway cleaning device. In some embodiments, the cleaning device comprises features configured to provide both visualized suctioning of the distal airways of a patient and cleaning of the interior surfaces of an endotracheal tube that is facilitating the patient's breathing. In some embodiments, the kit comprises an endotracheal tube. In some embodiments, the kit comprises one or more adapters, connectors or manifolds configured to couple the component parts of the kit together.

In accordance with several embodiments of the invention, the visualization scope or other visualization member (e.g., fiber optic scope) is reusable and can be used with one or more disposable components, devices, or systems. The reusable visualization scope can be combined with disposable components, for example, to view and verify the placement of an endotracheal tube and/or to view and clean an already-placed endotracheal tube. In some embodiments, the reusable visualization scope can be used with a disposable or reusable system that provides viewing combined with suctioning and irrigating of the lungs. In some embodiments, a visualization system that includes a sealed member around a flexible, non-articulating fiber optic scope or other member that is pressed against the viewing window at the distal end of the sealed member for optimal view and reusability without the need for sterilization creates a more efficient cost effective delivery of airway viewing and maintenance. Mineral oil, silicone oil, and/or other suitable fluids or substances can be used between these members to act as an optical coupling agent if there is not continuous and/or complete intimate contact between two adjacent mating surfaces. The fluids or other substances can create an approximately equivalent refractive index between the two materials (e.g., refractive index matching). The use of optical coating or optical coupling agents and/or other refractive index matching techniques can reduce reflection and/or improve the contrast of the images captured by the visualization system.

In some embodiments, one or more ports of the adapters or manifolds described herein can be shaped, angled or curved in a similar manner as the device being introduced through the port to aid in the ease of introduction, removal and collection of organized secretions or biofilm. The adapters or manifolds can be connected to any tube-like structure, including, but not limited to, endotracheal tubes, percutaneous tracheostomy devices, urinary catheters, or dialysis catheters, chest tubes, or other catheters and tubes. In some embodiments, the angled port is designed to accept a small diameter (e.g., 1-2 mm outer diameter) scope for verification of tube positioning.

In accordance with some embodiments of the invention, the adapters or manifolds can be used with "closed suction" systems. The adapter or manifold can include three ports, with one port or tube for connection to oxygen tubing or directly to a ventilator, one port or tube for a "closed suction" catheter, and one port or tube for introduction of visualization, irrigation, distal airway cleaning device, endotracheal tube cleaning device, suction device, bronchoscope and/or the like. Any ports or tubes not in use can be sealed and capped. The device adapter or manifold can be configured to be used multiple times or a single time.

In some embodiments, a method comprises coupling a closed suction system to the main port of the endotracheal tube coupling adapter. The step of cleaning the endotracheal tube further may comprise mechanically or pneumatically expanding the removal member to contact the inner surface of the endotracheal tube. The cleaning device may comprise a suction catheter comprising one or more cleaning and/or removal members for cleaning endotracheal tubes in addition to suctioning distal airways of the patient. In some embodiments, the method comprises inserting a visualization scope (e.g., fiber optic scope, bronchoscope) through the flap valve of the biofilm collection member. In some embodiments, the method comprises inserting a small visualization scope through a 30-45 degree angled irrigation port.

In accordance with several embodiments, a method of facilitating collection of biofilm removed from an endotracheal tube while providing continued access to a patient's airway and without requiring disconnection from the ventilator is provided. In some embodiments, the method comprises coupling a multi-port endotracheal tube adapter (such as the multi-port coupling members or adapters described herein) to an endotracheal tube. In some embodiments, the method comprises inserting a visualization device (such as the visualization devices described herein or a bronchoscope) through a one-way valve of a main shaft of the multi-port endotracheal tube adapter and advancing the visualization device into the endotracheal tube. In some embodiments, the visualization device is configured to confirm proper positioning of the endotracheal tube during and/or following intubation. In some embodiments, the method comprises removing the visualization device from the multi-port endotracheal tube adapter. In some embodiments, the method comprises inserting a small (e.g., 1-2 mm outer diameter) visualization scope through a 30-45 degree angled irrigation port.

In accordance with several embodiments, a device or system configured to clean a body-inserted tube is provided. The device or system may be configured to be used in an open suction system or a partially open suction system. The device or system includes a suction catheter configured to clean an interior surface of a body-inserted tube and/or airways (e.g., lungs or portions of tracheobronchial tree) beyond a distal tip of the body-inserted tube. The suction catheter may include a cleaning portion located at or near a distal end of the suction catheter. The cleaning portion may comprise at least one cleaning member configured to be radially expanded (e.g., inflated by a gas or liquid or mechanically expanded). The device or system may also include a bivalved housing located at a proximal end of the suction catheter. The bivalved housing may comprise a suction control unit configured to control suction through the suction catheter and an activation mechanism (e.g., syringe) configured to selectively expand the at least one cleaning member. Upon expansion of the at least one cleaning member, at least a portion of the at least one cleaning member may be configured to contact an interior surface of a body-inserted tube such that when the suction catheter is withdrawn from the body-inserted tube, biofilm collected on the interior surface is removed by the at least one cleaning member. In some embodiments, at least one suction port is disposed distal of the at least one cleaning member. In some embodiments, at least one suction port is disposed proximal of the at least one cleaning member.

In some embodiments, the suction catheter comprises a pilot channel extending from the activation mechanism to the cleaning portion. The activation mechanism may comprise a syringe mechanism configured to inflate the expandable cleaning member by delivering a predetermined amount of gas or liquid to the at least one cleaning member through the pilot channel. In one embodiment, the at least one cleaning member comprises a balloon. The balloon may comprise one or more rings or wipers positioned around the outer surface of the balloon. In some embodiments, a leading edge of the rings or wipers comprises a squared or substantially squared edge. In some embodiments, at least a portion of the rings or wipers is smooth. The cleaning member and/or a portion of the length of the suction catheter may comprise a lubricant coating, which may be integral or removable.

In accordance with several embodiments, a cleaning system adapted to clean a body-inserted tube, (e.g., endotracheal tube) comprises a suction catheter adapted to clean an interior surface of a body-inserted tube. The suction catheter comprises a cleaning portion located at or near a distal end of the suction catheter. The cleaning portion comprises a deployable (e.g., expandable) cleaning member. The suction catheter also comprises a proximal controller located at a proximal end of the suction catheter. The proximal controller is adapted to facilitate operation in one of the following three operational states: i) a first operational state in which only the cleaning member is functional, ii) a second operational state in which only suction is functional, or iii) a third operational state in which neither suction nor the cleaning member is functional. Upon expansion of the expandable cleaning member, at least a portion of the cleaning member is adapted to contact the interior surface of the body-inserted tube such that when the suction catheter is withdrawn from the body-inserted tube, biofilm or other debris collected on the interior surface is removed by the cleaning member. The suction catheter also comprises a distal suction port disposed distal of the cleaning member along a length of the suction catheter, the distal suction port being in fluid communication with a lumen extending from the proximal controller to the distal suction port. The distal suction port is adapted to facilitate suctioning distal to the cleaning member. The suction catheter may comprise a plurality of distal suction ports and/or one or more suction ports proximal to the cleaning portion.

Transition between operational states may be accomplished by rotation of a portion of the proximal controller with respect to a main body of the proximal controller. In some embodiments, a portion of the proximal controller is adapted to rotate between three rotational positions, each rotational position corresponding to one of the three operational states. In some embodiments, a locking mechanism prevents suction and/or deployment (e.g., expansion) of the cleaning member in particular operational states and during transitions between operational states or configurations. The proximal controller may include visual indicia (e.g., alphanumeric characters, graphical icons or symbols, colors, and/or mechanical features such as protrusions or recesses) corresponding to each rotational position and corresponding operational state. In accordance with several embodiments, rotation between each rotation position is adapted to be confirmed by an audible confirmation, a visual confirmation and a tactile confirmation, thereby providing increased safety. The audible confirmation and the tactile confirmation may result from toggling between detents on or within the proximal controller upon rotation of the portion of the proximal controller with respect to the main body.

In various embodiments, the proximal controller comprises a first actuation member (e.g., button, switch) adapted to control expansion (e.g., inflation/deflation) of the cleaning member and a second actuation member adapted to control suction through the suction catheter. The actuation members may be configured to be continuously actuated to deploy the cleaning member or maintain suction or may be configured to toggle on and off with a single press or other actuation action. In one embodiment, the cleaning member comprises an inflatable balloon having one or more integrated rings or wipers. The leading edge of the rings or wipers may include a squared or substantially squared edge. In some embodiments, the cleaning member and/or a portion of the length of the suction catheter comprises an integral lubricious coating to facilitate movement while the cleaning member is expanded within the body-inserted tube. The cleaning member and/or a portion of the length of the suction catheter may comprise an antimicrobial coating in addition to or without the lubricious coating. In some embodiments, the suction catheter and the cleaning member are formed (partially or entirely) of the same material. In one embodiment, the material is silicone. The cleaning member may be adhered or joined to the suction catheter using a silicone adhesive.

In some embodiments, the suction catheter is coextruded over a wire (e.g., braided or solid wire). The cleaning member may comprise a sponge-like material that, when compressed, is adapted to deliver antimicrobial or other solutions or gels or compounds to the body-inserted tube. In some embodiments, the proximal controller comprises an air or fluid reservoir or cylinder. The volume of the inflatable balloon may be controlled by one or more holes positioned along a length of the air reservoir. The hole(s) may be positioned at locations corresponding to differing sizes of internal diameters of body-inserted tubes (e.g., endotracheal tubes). The hole(s) may advantageously accommodate leaks to the external environment by allowing the system to recharge.

In accordance with several embodiments, the cleaning system further comprises a manifold, or adapter, adapted to removably couple to the body-inserted tube and a flexible enclosure adapted to extend from the proximal controller of the suction catheter to the manifold, thereby preventing exposure of the suction catheter to an external environment. The manifold may comprise a swivel connector having a tapered surface without step-offs or edges within the manifold so as to prevent hang-up of the suction catheter and so as to reduce collection of biofilm or other debris in the manifold as the suction catheter is being withdrawn into and through the manifold. The manifold may comprise a diaphragm or valve to seal off the external environment and/or to facilitate scraping off the biofilm or other debris from the cleaning member.

In some embodiments, the cleaning system comprises a polymeric tubular extension coupled to the manifold and extending into the flexible enclosure, wherein the tubular extension is configured to receive a flexible catheter and pull the flexible catheter at least partially into the body-inserted tube through the manifold. The polymeric tubular extension may be particularly advantageous for soft, pliable catheters or instruments and/or catheters having outer diameters of less than 5 mm (e.g., catheters designed for neonate or pediatric patients).

In accordance with several embodiments, a cleaning device adapted to clean a body-inserted tube comprises a proximal end, a distal end and an elongate body extending from the proximal end to the distal end. A material is coextruded with at least a portion of the elongate body so as to increase pushability and/or reduce stretch of at least the portion of the elongate body. The embodiment of the device comprises a deployable cleaning member located at or near a distal end of the elongate body. The cleaning member may be deployed (e.g., expanded) by inflation (e.g., pneumatic or hydraulic means) or by mechanical means (e.g., a mechanically-expandable mesh scaffold). The embodiment of the device also comprises a proximal controller located at a proximal end of the elongate body. The proximal controller comprises a suction control unit configured to control suction through a lumen of the elongate body and a deployment mechanism configured to selectively deploy (e.g., expand) the cleaning member. Upon deployment (e.g., expansion) of the cleaning member, at least a portion of the cleaning member is configured to contact an interior surface of a body-inserted tube such that when the device is withdrawn from the body-inserted tube, biofilm collected on the interior surface is removed by the cleaning member. The embodiment of the device further comprises at least one suction port disposed distal of the cleaning member.

In some embodiments, the coextruded material is braided wire or solid wire. In one embodiment, the device comprises a pilot channel extending from the deployment mechanism to the cleaning portion. The deployment mechanism may comprise a syringe mechanism configured to inflate the expandable cleaning member by delivering a predetermined amount of gas or liquid to the cleaning member through the pilot channel. In one embodiment, the cleaning member comprises an inflatable balloon having one or more integrated rings or wipers. A leading edge of the rings or wipers may be squared or substantially squared off. The cleaning member and/or a portion of the length of the elongate body may comprise an integral lubricant coating and/or an antimicrobial coating. In one embodiment, both the elongate body and the cleaning member are composed (partially or entirely) of silicone having the same or similar durometer. The cleaning member may be adhered or joined to the suction catheter using silicone joint adhesive.

In accordance with several embodiments, a cleaning device adapted to clean a body-inserted comprises a catheter (e.g., elongate tube or wire or other medical instrument) having a proximal end and a distal end. A material is coextruded with at least a portion of the catheter during manufacture that is configured to increase pushability and/or reduce stretch of at least the portion of the catheter. The embodiment of the cleaning device also includes a cleaning member located at or near the distal end that is configured to be expanded. The cleaning device also includes a proximal controller located at a proximal end of the catheter. The proximal controller includes an actuation mechanism configured to selectively expand the cleaning member wherein, upon expansion of the cleaning member, at least a portion of the cleaning member is configured to contact an interior surface of a body-inserted tube such that when the catheter is withdrawn from the body-inserted tube, biofilm collected on the interior surface is removed by the cleaning member. In accordance with several embodiments, the cleaning devices (e.g., catheters) described herein may be used to apply lubricant and/or antimicrobial agents to an inner surface of a body-inserted tube (e.g., endotracheal tube). For example, the lubricant and/or antimicrobial agents may be coated on the cleaning member and/or portion(s) of the catheter or may be delivered through openings along the cleaning member and/or portion(s) of the catheter.

In accordance with several embodiments, a method of cleaning a body-inserted tube (e.g., using any of the systems or devices described herein) comprises inserting a distal tip of a suction catheter of a closed suction system module into the body-inserted tube (e.g., endotracheal tube) and advancing the distal tip of the suction catheter to a first desired depth within the body-inserted tube. The closed suction system module comprises a flexible sleeve extending from a distal connection member (e.g., a modular connector) at a distal end of the closed suction system module to a proximal controller of the closed suction system module. The suction catheter comprises a distal inflatable cleaning member or other distensible cleaning member as described herein. The proximal controller comprises a first actuation member adapted to control suction through the suction catheter and a second actuation member adapted to cause inflation or other distension or expansion of the distal cleaning member such that at least a portion of the distal cleaning member comes in contact with an interior surface of the body-inserted tube. In one embodiment, the proximal controller is adapted to facilitate operation of the suction catheter in one of the following three operational states: i) a first operational state in which only the cleaning member is functional, ii) a second operational state in which only suction is functional, or iii) a third operational state in which neither suction nor the cleaning member is functional. The order of the states may be altered.

The method may comprise causing the proximal controller to operate in the second operational state and performing suctioning using the suction catheter by actuating the first actuation member while withdrawing the distal tip of the suction catheter out of the endotracheal tube and into the flexible sleeve. In one embodiment, the suctioning is performed for a duration of between 5-15 seconds. In some embodiments, the distal end portion of the suction catheter may comprise one or more marks that are visible inside the flexible sleeve when the suction catheter has been sufficiently withdrawn from the body-inserted tube and/or manifold. In one embodiment, the method comprises advancing the distal tip of the suction catheter to a second desired depth within the body-inserted tube. In some embodiments, the method further comprises causing the proximal controller to operate in the first operational state and inflating the inflatable member by actuating the second actuation member and withdrawing the distal tip of the suction catheter out of the endotracheal tube and into the flexible sleeve. In some embodiments, the cleaning may be performed without first performing suctioning. In other embodiments, suctioning is performed without performing cleaning using the inflatable or otherwise deployable cleaning member.

In some embodiments, inserting the distal tip of the suction catheter of the closed suction system module into the body-inserted tube and advancing the distal tip of the suction catheter to the first desired depth within the endotracheal tube is performed while the proximal controller is operating in the third operational state. In some embodiments, the method comprises coupling a distal port of a multi-port manifold to the body-inserted tube and coupling the distal connection member (e.g., modular connector) of the closed suction system module to a proximal port of the multi-port manifold. The method may further comprise irrigating the manifold and/or the distal portion of the suction catheter (including suction holes or the distal cleaning member) through an irrigation port of the distal connection member of the closed suction system module. In one embodiment, the manifold may comprise an irrigation port.

In some embodiments, the method comprises suctioning the manifold with the suction catheter while the proximal controller is operating in the first operational state to remove debris or secretions within the manifold created during irrigation or withdrawal of the suction catheter into the manifold. The method may optionally comprise disconnecting the closed suction system module from the manifold and placing a cap over the distal connection member of the closed suction system module. Irrigation may be performed at this time to clean the distal portion of the suction catheter. In some embodiments, the method comprises coupling an accessory adapter to the proximal port of the manifold after disconnecting the closed suction system module. A visualization and/or cleaning instrument (e.g., bronchoscope, bronchioalveolar lavage catheter, endotracheal tube cleaning device or distal airway cleaning and/or visualization device) may be inserted through the accessory adapter and the manifold and into the body-inserted tube. The visualization and/or cleaning instrument may then be removed and the accessory adapter may be decoupled from the manifold. After removing the accessory adapter, the cap may be removed from the closed suction system module and the closed suction system module may be reconnected to the proximal port of the manifold. The modularity of the system and methods may facilitate cleaning of the body-inserted tube, cleaning of distal airways, visualization, irrigation and/or sterilization without breaking the ventilation connection and/or without removing the body-inserted tube. The modularity may facilitate insertion of multiple instruments within or through the body-inserted tube without breaking the ventilation connection and/or without removing the body-inserted tube.

In some embodiments, the method comprises coupling a ventilator port of the manifold to a ventilation source (e.g., ventilator or ventilation unit). Ventilation may advantageously be maintained during performance of the entire method. In some embodiments, the manifold comprises a stopcock or other valve control adapted to open and close access to the body-inserted tube by the suction catheter while still maintaining ventilation. The stopcock may comprise a valve or diaphragm to seal off the manifold from exposure to the external environment or the flexible sleeve of the closed suction system module through the proximal port.

In accordance with several embodiments, a closed chest tube cleaning system comprises a closed system module comprising a cleaning catheter having a distal expandable cleaning member, a proximal controller, and a protective sheath. The cleaning system further comprises an adapter comprising three ports: a first port configured to couple to a chest tube inserted within a lung space of a patient, a second port configured to couple to the closed system module, and a third port configured to couple to drainage tubing for suction. The protective sheath extends from the proximal controller to the second port of the adapter.

In one embodiment, the expandable cleaning member comprises an inflatable balloon having one or more integrated shaving rings. The one or more integrated shaving rings may comprises a squared leading edge. The expandable cleaning member may be inflatable or mechanically expandable. The proximal controller may be configured to cause expansion (e.g., inflation) of the expandable cleaning member. In some embodiments, the adapter comprises a swivel connector configured to be coupled to and rotate between two chest tubes. The closed chest tube cleaning system may be used to clean one or more chest tubes inserted within a lung of a patient.

According to some embodiments, the devices and/or systems disclosed herein are advantageously disposable and relatively inexpensive to manufacture. Thus, such embodiments do not require subsequent cleaning, sterilization, and repackaging. Some embodiments are advantageous because they can be performed via the natural airway of a patient while a patient undergoes assisted ventilation utilizing an endotracheal or tracheostomy tube. Several embodiments provide high quality optics and imaging while being easy to use without extensive, specialized training. Some embodiments of the inventions include low-cost visualization members, elements, or scopes that can be reused many times (e.g., 20-200 times) to provide high quality optics and visualization at a very low cost per use, thereby enabling hospitals or other patient care facilities to provide better, more cost effective, health care.

In some embodiments, the devices, methods and systems described herein facilitate intubation by direct visualization of the patient's native airway as the endotracheal tube is inserted and/or provide for confirmation of the position of the endotracheal tube within the native airway (e.g., trachea) after insertion of the endotracheal tube. In some embodiments, an image of the position is obtained to document the position for the patient's medical record and is stored in a memory device. The embodiments described herein advantageously obviate the need to perform a chest x-ray of the patient to confirm the position of the endotracheal tube. Depending on how busy the x-ray department is at the time and other unpredictable factors, such as time of day and number of personnel available, a confirmatory chest x-ray can take a relatively long time to be obtained and interpreted, which can seriously threaten the survival of an acutely ill patient. In addition, chest x-rays are relatively expensive and expose the patient to unnecessary or undesirable radiation. In some embodiments, confirmation of the position of the endotracheal tube can be obtained at the bedside of an already intubated patient in the ICU. The embodiments described herein may obviate the need for a confirmatory x-ray or bronchoscopy, which can be especially harmful for neonatal and pediatric patients whom often undergo multiple x-rays during their stay in the ICU.

In several embodiments, the cleaning device is particularly advantageous because it rejuvenates endotracheal tubes that have been clogged or otherwise contaminated with biofilm. In one embodiment, the cleaning device removes biofilm such that endotracheal tube resistance is decreased by at least 90% after cleaning, thus enhancing the functionality of the endotracheal tube. In some embodiments, the cleaning device removes greater than 99% of bacteria (as determined by colony counts in the biofilm) from the endotracheal tube. Thus, in several embodiments, the cleaning device offers significant economic and clinical benefits. Some embodiments disclosed herein are particularly advantageous because they do not require performance by a physician and do not require sedation, short acting paralytics, increased intravenous fluid administration, and/or vasopressors. Some embodiments of the inventions are advantageous because they are minimally invasive and they minimize pain and discomfort to the patient and minimize the overall time of cleaning. Some embodiments of the inventions reduce the number of times that suctioning must be performed in a twenty-four hour period.

For purposes of summarizing the disclosure, certain aspects, advantages and novel features of embodiments of the inventions have been described herein. It is to be understood that not necessarily all such advantages can be achieved in accordance with any particular embodiment of the inventions disclosed herein. Thus, the embodiments disclosed herein can be embodied or carried out in a manner that achieves or optimizes one advantage or group of advantages as taught herein without necessarily achieving other advantages as can be taught or suggested herein. The methods summarized above and set forth in further detail below describe certain actions taken by a practitioner; however, it should be understood that they can also include the instruction of those actions by another party. Thus, actions such as "inserting a suction catheter" include "instructing the insertion of a suction catheter." Further aspects of embodiments of the invention will be discussed in the following portions of the specification. With respect to the drawings, elements from one figure may be combined with elements from the other figures.

BRIEF DESCRIPTION OF THE DRAWINGS

FIGS. 2A-2C illustrate various views of various embodiments of a valve or stopcock configured to be incorporated into a manifold, such as the one illustrated in FIG. 1.

FIGS. 3A and 3B illustrate one embodiment of a distal portion of a suction catheter device comprising an expandable cleaning portion.

FIGS. 4A and 4B illustrate one embodiment of a distal portion of a suction catheter device comprising an expandable cleaning portion.

FIGS. 5A and 5B illustrate one embodiment of a distal portion of a suction catheter device comprising an expandable cleaning portion.

FIGS. 6A and 6B illustrate one embodiment of a distal portion of a suction catheter device comprising an expandable cleaning portion.

FIGS. 7A-7C illustrates various views of an embodiment of a suction catheter device comprising an expandable cleaning portion positioned within an interior of an endotracheal tube or other body inserted tube.

FIGS. 11A, 11B and 12 illustrate embodiments of alternative adapters and devices configured to be coupled to the manifold of the closed suction cleaning system of FIG. 1.

FIG. 13 illustrates a sealing member configured to be inserted within a distal end of the closed suction system module upon removal of the closed suction system module from the manifold of the closed suction cleaning system of FIG. 1.

FIG. 15A-15C illustrate a schematic representation of an embodiment of an open suction cleaning system.

FIG. 17 illustrates an embodiment of an endotracheal tube cleaning device for complementary cleaning in an open suction environment.

FIGS. 23A-23E provide more detailed views of assembled sub-components of the closed suction system of FIG. 23.

FIG. 23F is an isometric side view of the closed suction system of FIG. 23 illustrated without the sleeve or enclosure for illustration purposes.

DETAILED DESCRIPTION

Figure 1:
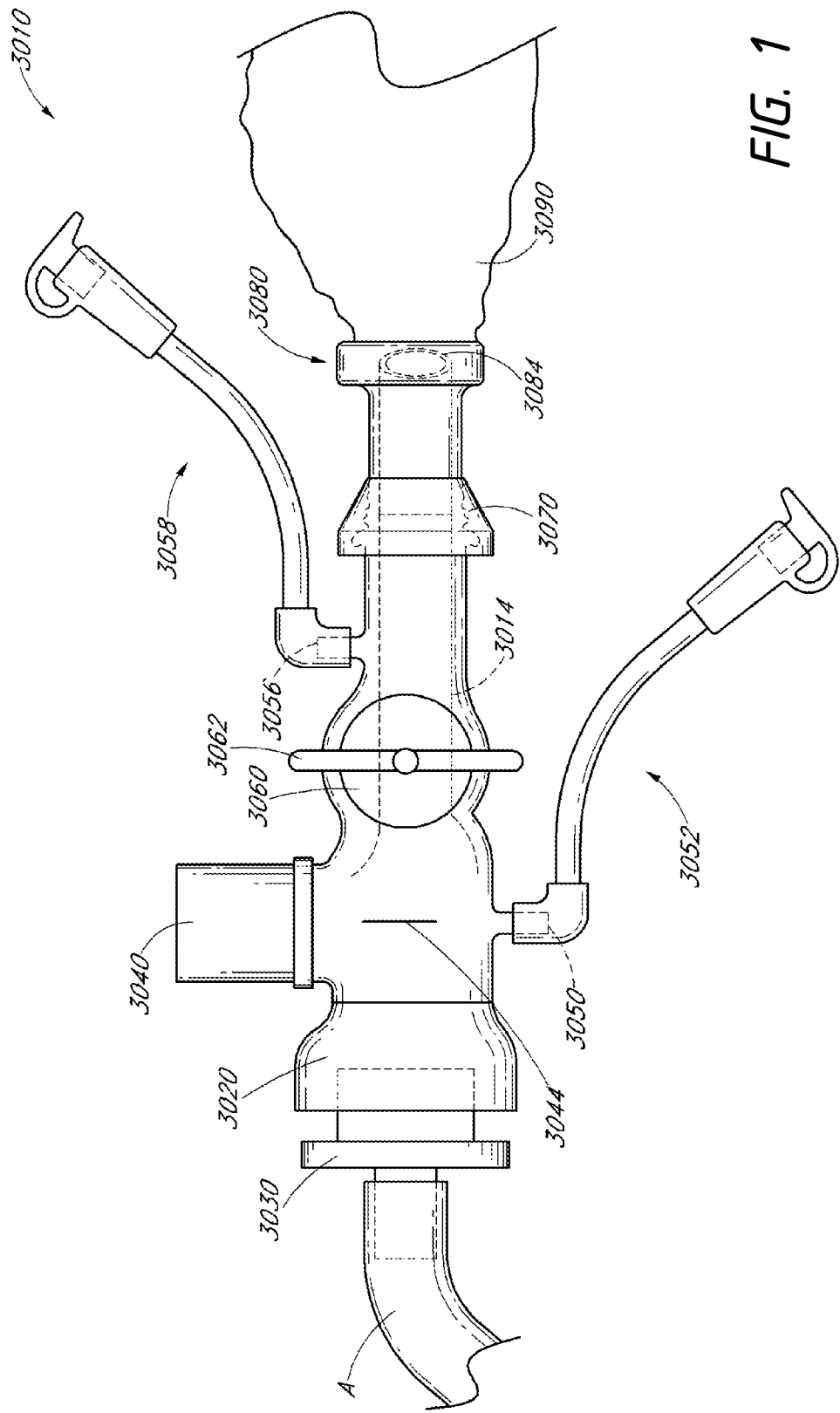
FIG. 1 illustrates one embodiment of a manifold configured to be used with a suction catheter device.

Several embodiments of cleaning systems, devices and methods described herein are particularly well-suited to remove biofilm (e.g., secretions, debris and/or other materials) from body-inserted tubes (e.g., endotracheal tubes) and the respiratory tract or tree of a patient within a closed or partially closed suction system while a patient is connected to a ventilator Several embodiments of visualization systems, devices and methods described herein are particularly well-suited to facilitate positioning of an endotracheal tube within a patient's native airway. The various devices, systems, methods and other features of the embodiments disclosed herein may also be utilized or applied to other types of apparatuses, systems, procedures, and/or methods, whether medically related or not. For example, the embodiments disclosed herein can be utilized for, but are not limited to, bronchoscopes, chest drainage tubes, gastrostomy drainage tubes, abdominal drainage tubes, other body drainage tubes, feeding tubes, endoscopes, percutaneous dialysis catheters, urinary catheters, urethral catheters, Foley catheters, and any other percutaneous or per os catheters or body-inserted tubes. In addition, the various embodiments disclosed herein can be used to facilitate positioning of other body-inserted members or devices. The visualization features described herein can be used to visualize the internal features of any anatomical structure, such as the colon, esophagus, nasal passages, ear passages, lungs, abdomen, uterus, urethra, abdominal cavity, thoracic cavity, peritoneal space, joints (e.g., knees, ankles, wrists, shoulders, hips), blood vessels, and/or any other anatomical passage or location.

The materials used for the various components of the cleaning and/or visualization devices and systems described herein can advantageously comprise one or more biocompatible materials. Such materials can be rigid or semi-rigid and/or flexible, as desired or required for a particular application or use. The materials used can include, but are not limited to, polyether ether ketone (PEEK), Nylon 6/6, polyethylene, polypropylene, polyethylene terephthalate (PET), glycol-modified PET, polyvinyl chloride (PVC), thermoplastic elastomers (TPEs) such as PEBAX TPEs, other natural or synthetic polymers (e.g., KRATON polymers), silicone, natural rubber, latex, polycarbonate, K resin, acrylonitrile butadiene styrene (ABS), styrenes and/or other thermoplastic elastomers or polymers.

The terms "debris" and "secretions" as used herein shall be given their ordinary meaning and shall include, without limitation, biological fluids, solids, gels, deposits, films, debris, and/or secretions, such as mucosal secretions, blood, bacteria, biofilm, viruses, other microorganisms, protein, feces, urine, albumin and/or any other biological or biologically-related materials. The term "native airway(s)" as used herein shall be given its ordinary meaning and shall include, without limitation, the oral cavity, nasal passages, pharynx, larynx, trachea, and/or any portion of the lungs, including any of the branches of the tracheobronchial tree.

The term "biofilm" as used herein shall be given its ordinary meaning and shall include, without limitation, biological fluids, solids, gels, deposits, films, debris, and/or secretions, such as mucosal secretions, blood, blood clots, bacteria, viruses, other microorganisms, protein, feces, urine, albumin and/or any other biological or biologically-related materials. In some embodiments, the biofilm may comprise any debris that can be deposited and come to rest within a lumen of an endotracheal tube, such as blood clot material, mucus, secretions, biofilm, or any other type of particulate matter that might find itself within the lumen of an endotracheal tube. In some embodiments, the biofilm may comprise any debris collected or removed from airways of a patient.

FIG. 1 illustrates one embodiment of a manifold 3010 configured to be used in a closed-suction endotracheal tube and distal airway cleaning system. As shown, the manifold 3010 comprises an endotracheal tube coupling 3020 for placing the manifold 3010 in fluid communication with an endotracheal tube A. In some embodiments, the endotracheal tube A is attached to the coupling 3020 of the manifold 3010 using a universal connector 3030. Such a universal connector 3030 can advantageously permit the manifold 3010 to attach to endotracheal tubes of various sizes and types. According to some embodiments, the coupling 3020 comprises a swivel connector that is configured to rotate (e.g., 360°) about its longitudinal axis. With further reference to FIG. 1, the manifold 3010 can additionally comprise a ventilator port 3040 sized, shaped and otherwise configured to removably attach to a ventilator conduit (not shown). In some embodiments, the ventilator port or coupling 3040 can be configured to swivel about its longitudinal axis (e.g., 360°). The manifold 3010 can comprise one or more lines 3044 or other markings or indicators that are used to determine and confirm the depth of insertion of marked (e.g., centimeter marked) closed suction catheters that are passed into the endotracheal tube A and/or respiratory tree (e.g., trachea, lung portions) of a subject.

With continued reference to FIG. 1, the manifold 3010 can comprise one or more additional ports, couplings and/or other connection points. For example, the illustrated embodiment includes a delivery port 3050 and an irrigation port 3056. In some embodiments, the delivery port 3050 is adapted to attach (e.g., releasably) to a metered dose inhaler (MDI) drug delivery system in order to allow a clinician (e.g., physician, nurse, physician's assistant, other practitioner, etc.) to selectively deliver a specific amount of one or more medicaments (e.g., pharmaceuticals, other fluids, etc.) into the manifold 3010. In some embodiments, each of the ports or couplings 3050, 3056 comprise an openable cover 3052, 3058. The cover 3052, 3058 can be configured to be permanently or removably attached to the corresponding port or coupling, as desired or required. For instance, with respect to the embodiment of FIG. 1, fluid can be passed through one or both of the covers 3052, 3058 in order to irrigate and clear the manifold 3010 (e.g., should it become fouled with endotracheal tube or pulmonary contents, other debris, etc.). In one embodiment, the irrigation port 3056 is used to clean a distal tip of a closed suction catheter, a closed suction catheter with an endotracheal tube cleaner and/or any other device or instrument that can be inserted through the manifold 3010 into the endotracheal tube A and/or respiratory tree of the subject being treated. In some embodiments, the port(s) 3050 and/or 3056 is (are) angled proximally 30-60 degrees with respect to the manifold body. In such embodiment, the covers 3052 and/or 3058 are configured to accept fluids and a small diameter (e.g., 1-2 mm outer diameter) visualization scope or instrument.

In some embodiments, the manifold 3010 is configured to connect to a sleeve, condom, sheath or other collapsible and flexible member 3090 that surrounds and protects (e.g., from exposure to the external or outside environment) a suction catheter (not shown in FIG. 1) positioned within the sleeve 3090. For example, the sleeve 3090 protects the environment from contamination by material brought back from the endotracheal tube A and/or lung portions after a suction or other cleaning procedure. According to some embodiments, a diaphragm or other sealing barrier member 3080 can be positioned between the manifold 3010 and the sleeve 3090. Such a diaphragm 3080 can be configured to advantageously permit various instruments (e.g., with outer diameters in the range of approximately 1 mm-10 mm (e.g., 3 mm-8 mm) to be positioned and/or removed therethrough while maintaining or substantially maintaining a seal. Accordingly, no loss or substantially no loss of positive pressure in the ventilatory circuit can occur while the clinician is using the manifold, or adapter, 3010, in a closed suction system. In some embodiments, the diaphragm 3080 comprises one or more soft materials that provide one or more sealingly accessible openings 3084 that generally maintain a seal around catheters and/or instruments that are passed through the diaphragm 3080 at that location. Further, as illustrated in FIG. 1, the sleeve 3090 (and/or an adjacently coupled diaphragm 3080) can be secured to the manifold 3010 using a closed suction coupling 3070 of a closed suction system module or assembly.

In FIG. 1, the manifold 3010 comprises a valve or flow-regulating device 3060 (e.g., stopcock) that can be used to advantageously regulate if and by how much the internal passage of the manifold 3010 is opened or closed. For example, in some embodiments, by virtue of a rotation (e.g., 90° turn) of the handle or other actuator 3062, the manifold 3010 is switched between a first (e.g., "closed") position where there is no (or substantially no) ability of fluids to pass through the valve 3060 and a second (e.g., "open") position where fluids are able to pass through the valve 3060. Thus, in the first, closed position, there is no or substantially no fluid communication between the sleeve 3090 and the portion of the manifold 3010 distal to the valve 3060. Whereas, in the second, open position, there is fluid communication between the sleeve 3090 and the portion of the manifold 3010 distal to the valve 3060 (e.g., the endotracheal tube A). In some embodiments, the internal passage 3014 of the manifold 3010 and the opening within the valve 3060 is a minimum of approximately 10 mm. However, in other embodiments, the minimum opening can be smaller or larger than 10 mm (e.g., 6 mm, 7 mm, 8 mm, 9 mm, 10 mm, 11 mm, 12 mm, greater than 12 mm, smaller than 6 mm, ranges between the foregoing values, etc.), as desired or required.

FIGS. 2A-2C illustrate embodiments of the valve (e.g., stopcock) 3060 of the manifold 3010 that is adapted to allow selective placement of instruments and/or other devices into the distal endotracheal tube and respiratory tree of the subject being treated. As discussed above, devices that may be positioned through the valve 3060 and other internal passageways of the manifold 3010 include, but are not limited to, bronchoscopes, other visualization instruments, endotracheal tube cleaning devices, bronchioalveolar lavage catheters, plain suction catheters and other types of suction catheters, combined endotracheal tube cleaning devices and suction catheters (as discussed in greater detail herein) and and/or other devices that are capable of fitting through an endotracheal tube (e.g., instruments or devices having a maximum outer diameter of approximately 9 mm).

FIG. 2A schematically depicts a lateral view of one embodiment of a valve (e.g., stopcock) 3060 of the manifold 3010. In the illustrated position, the handle or actuator 3062 can be selectively rotated or otherwise manipulated (e.g., approximately 90° relative to the longitudinal axis of the internal passageway extending through the manifold and the valve) so that the generally tubular passageway 3064 of the valve 3060 can either be "in-line" or "open," wherein generally free passage of air, other fluids and/or devices is permitted between the distal ventilatory circuit and the proximal access port on the manifold (e.g., closed suction coupling 3070, FIG. 1), or "closed," wherein no communication exists between the ventilatory circuit and a proximal manifold port.

FIG. 2B schematically illustrates different axial views of one embodiment of a manifold valve 3060 having a generally spherical housing. Further, FIG. 2C schematically illustrates different axial views of one embodiment of a manifold valve 3060 having a generally cylindrical housing. In other embodiments, the shape and general design of the valve 3060 and its various components can vary, as desired or required.

In use, according to some embodiments, a closed suction catheter, a combined suction catheter and endotracheal cleaning device, a visualization device and/or other device or instrument is withdrawn rearwardly or cephalad through the manifold 3010 such that the distal tip of such device or instrument resides just proximally to the valve 3060, which may then be closed by rotating 90°. The tip of the catheter or other device may then be cleaned by injection of water or saline (e.g., via selective delivery of such fluids through the irrigation port 3056) and, in some embodiments, the application (e.g., simultaneous or not) of suction (e.g., through the suction catheter). As discussed above, positioning the valve 3060 in the "closed" position and incorporation of a diaphragm or other sealing member 3070 within the manifold 3010 help to advantageously prevent or reduce the likelihood of fluids injected through the irrigation port 3056 from migrating into other portions of the manifold 3010 or proximally into the sleeve or flexible protective sheath 3090. Accordingly, such embodiments can advantageously allow both suctioning of the endotracheal tube and distal respiratory tree, as well as cleaning of the inside of the endotracheal tube by a cleaning portion or member of a suction catheter without opening the ventilatory system or allowing loss of positive pressure within the ventilatory circuit.

As discussed above, the closed suction system (e.g., one utilizing a sleeve, condom or other flexible member 3090 attached to a proximal end of the manifold 3010) can be configured to house a suction catheter 3200 and shield such a suction catheter from the outside environment, thereby preventing or minimizing the risk of contamination. With reference to FIGS. 3A and 3B, the suction catheter 3200 can additionally comprise an endotracheal tube cleaning portion 3210 along or near its distal end. Although these types of suction catheters with an endotracheal tube cleaning portion or member are described herein with use in closed suction systems, such devices can be used in non-closed or open suction systems. For example, devices that can be used in open suction systems or in partially-closed/partially-open suction systems are illustrated and described in connection with FIGS. 15 and 16. In other words, such combined suction and endotracheal tube cleaning devices can be used independently of a manifold and/or a protective sleeve. Further, any of the combined suction and endotracheal tube cleaning devices can incorporate any of the mechanically-expandable cleaning members or other cleaning members disclosed herein or in U.S. Publ. No. 2011/0023885, U.S. Publ. No. 2013/0104884, and PCT Publ. No. WO 2011/126812, the entireties of each of which are hereby incorporated by reference herein, such as a mechanically-actuated scaffold (e.g., a mesh scaffold actuated by movement of two concentric tubes attached to opposite ends of the mesh scaffold with respect to each other).

With continued reference to the embodiment illustrated in FIGS. 3A and 3B, the distal end of the suction catheter device 3200 comprises an endotracheal tube luminal wiper or cleaning portion 3210. In some embodiments, the catheter body 3204 of the device 3200 comprises one or more side suction holes, openings or ports 3220, 3224 (e.g., distal alone (3220), distal and proximal (3220 and 3224), or proximal alone (3224)) distal and/or proximal to the cleaning device 3210, as desired or required. Such side holes, openings or ports 3220, 3224 are configured to be in fluid communication with one or more internal fluid passageways of the catheter body 3204. Further, the distal end 3228 of the catheter device can be at least partially open and in fluid communication with an interior passage of the catheter body 3204. Thus, suction can be accomplished along one or more different locations of the suction catheter. The number, size, and positioning of the suction holes, openings, or ports may be variably altered as part of the suction catheter design and manufacture in order to direct varying degrees of suction at specific locations along the suction catheter 3204. In addition, varying amounts of suction may be applied to the proximal and distal ports 3220, 3224. Such variations may be required depending on the overall dimensions and diameter of the suction catheter 3204 and the amount of suction (in mm Hg) intended for delivery at the suction holes, openings, or ports 3220, 3224, thereby allowing for dynamic suction control. In accordance with several embodiments, a suction catheter device comprising suction holes, openings, or ports 3220, 3224 both proximal and distal to the cleaning portion 3210 advantageously facilitates suction on both sides of the cleaning portion 3210. Suction holes, openings, or ports 3224 positioned proximal to the cleaning portion 3210 advantageously facilitate suction (and removal) of biofilm or other debris removed by the cleaning portion 3210 (e.g., cleaning members or wipers 3240) while the suction catheter device is being withdrawn, and may be the only source of suction if the main suction lumen of the suction catheter device 3200 is occluded by members of the cleaning portion 3210 (such as balloons).

As depicted In FIGS. 3A and 3B, the wiper or cleaning portion 3210 can comprise one or more distensible or extendable wiper members 3230, such as, for example, an expandable sleeve, ring or balloon. Such balloons or other distensible members 3230 can be configured to be moved between a collapsed position, where they remain adjacent the catheter body 3204 to which they are secured (as shown in FIG. 3A), and an expanded position, where they move away from the central axis and the outer diameter of the catheter body 3204 (as shown in FIG. 3B). As shown, in some embodiments, the cleaning portion 3210 is configured to at least partially contact the inside surface of a body-inserted tube (e.g., endotracheal tube) when the balloon or other distensible or expandable member 3230 is in the radially-expanded position. Accordingly, as the device 3200 is withdrawn (e.g., retracted rearwardly from inside the endotracheal tube or other body-inserted tube), biofilm and/or other debris is removed from within the tube. As shown in FIG. 3B, fluid or other air used to selectively expand the balloon or other distensible member 3230 can be routed to the interior of the balloon or other distensible member 3230 through one or more fluid passages 3260 of the catheter body 3204 and/or another interior portion of the catheter device 3200. In some embodiments, the wiper or cleaning portion 3210 is comprised of silicone of 50 A-70 A durometer.

With continued reference to FIGS. 3A and 3B, the cleaning portion 3210 of the catheter device 3200 comprises one or more cleaning, wiping or shearing members 3240 that are configured to engage and contact the inside wall of the body-placed or body-inserted tube (and/or the biofilm or other debris that has collected therein). For example, in the illustrated embodiment, the balloon or distensible member 3230 consists of a total of two shaving rings or cleaning members 3240. Such rings or other cleaning members 3240 can extend completely or partially around the circumference of the cleaning portion 3210, as desired or required. The rings or other cleaning members 3240 can have generally square or sharp (e.g., approximately 90°) edges. However, in other embodiments, the cleaning members 3240 comprise more rounded (non-sharp or smooth) profiles. Further, in other embodiments, the cleaning portion 3210 comprises more (e.g., 3, 4, 5, more than 5, etc.) or fewer (e.g., 1) rings or other cleaning members 3240. As discussed in greater detail below, the balloon or distensible member 3230 (and thus the cleaning portion 3210) is expanded (e.g., to engage the inside wall of the body inserted tube and/or the debris accumulated thereto) by selectively delivering a volume of fluid (e.g., air) to the balloon or distensible member 3230 via one or more "pilot channels" or air or fluid injection channels 3260 attached to or within the catheter device 3200.

According to some embodiments, the balloon or other distensible member 3230 is secured to the adjacent catheter body 3204 using any attachment method or device, as desired or required. For example, in the arrangement illustrated in FIGS. 3A and 3B, the balloon 3230 is connected to the catheter body 3204 using one or more adhesive joints 3236. Such adhesions or other joints can be located, either intermittently or continuously, along any distal, proximal and/or central portion of the balloon 3230. In some embodiments, the cleaning portion 3210 (e.g., balloon 3230, cleaning members 3240) and adjacent catheter body 3204 are composed (partially or entirely) of silicone and the adhesive joint is achieved with silicone adhesive.

According to some embodiments, the balloon 3230 and/or sleeve member comprises a generally soft material with memory and recoil characteristics such that when fluid or air is withdrawn from the balloon 3230, the cleaning portion 3210 returns to its collapsed position, immediately adjacent the suction catheter body 3204. In some embodiments, the balloon, wiper or sleeve member comprises a smooth surface along a portion of or the entire length and does not comprise any shaving rings or cleaning members. The balloon, wiper or sleeve member may comprise one or more of urethane, silicone, PEBAX thermoplastic elastomer, or PVC materials. In some embodiments, the balloon, wiper or sleeve member is comprised of silicone of 50 A-70 A durometer.

In some embodiments, such a catheter device 3200 is used for suction only without expansion of the cleaning portion 3210. Alternatively, the device 3200 can be utilized without suction and with only expansion of the cleaning portion 3210, as desired or required. In other embodiments, such devices 3200 advantageously enable a user to perform both (e.g., simultaneous) suctioning and cleaning of the body-inserted tube (e.g., endotracheal tube) via expansion of the cleaning portion 3210 and balloon or other distensible member 3230. In other embodiments, when the catheter device 3200 is withdrawn from the body inserted tube after expansion of the cleaning portion 3210, biofilm or other debris removed from the inside walls of the body-inserted tube that has collected proximally to the cleaning portion 3210 is removed by the application of suction to proximal suction ports 3224. In some embodiments, the suction ports 3220, 3224 may be designed (e.g., by varying the size, position, number, and suction pressures) to provide dynamic control of suction distal and/or proximal to the cleaning portion 3210. In one embodiment, when the balloon or other distensible member 3230 is expanded and suction is applied, only the proximal suction port(s) 3224 are activated. Additional details regarding the design and construction of a proximal control unit that allows the catheter devices 3200 to be used in varying modes are provided below.

FIGS. 4A and 4B illustrate another embodiment of a suction catheter device 3300 comprising a cleaning portion 3310 along its distal end 3328. This device is similar to the one illustrated in FIGS. 3A and 3B and discussed herein; however, the device 3300 depicted in FIGS. 4A and 4B comprises an additional balloon 3350 positioned along an interior of the outer balloon 3330. Thus, the cleaning portion 3310 of the illustrated device 3300 comprises a generally two-piece expansion mechanism. As shown, the inner balloon or other distensible or expandable member 3350 is distended by injection of air or other fluid through one or more pilot or fluid channels 3360 (e.g., located within or adjacent the wall of the catheter body 3304 and/or any other portion of the device 3300).

With continued reference to FIGS. 4A and 4B, in some embodiments, the outer balloon, sleeve or distensible member 3330 expands passively in response to distention of the inner balloon 3350. As with the embodiment of FIGS. 3A and 3B, one or more wipers and/or other shearing or cleaning members 3340 positioned along an exterior of the outer balloon 3330 are configured to contact the interior wall of the endotracheal tube or other body-inserted tube when the cleaning portion 3310 is in an expanded position. The cleaning member 3340 can comprise at least one squared edge that contacts the inside wall of the body-inserted tube with expansion. As discussed with reference to the device in FIGS. 3A and 3B above, this embodiment of the device may be used for suction only, distention of the cleaning member only, or with suction and distention of the cleaning member simultaneously, as desired or required.

According to some embodiments, the outer balloon or sleeve member 3330 and the inner balloon or extensible member 3350 both comprise one or more generally soft materials with memory and recoil characteristics such that when air or fluid is withdrawn from the inner balloon 3350, the cleaning portion 3310 (e.g., the combination of the inner balloon 3350 and the outer sleeve 3330) returns to its collapsed position, immediately adjacent the suction catheter body 3304.

FIGS. 5A and 5B illustrate another embodiment of a suction catheter device 3400 comprising a cleaning portion 3410 along its distal portion. As discussed above with reference to other embodiments, the illustrated device 3400 can be used in a closed suction system; however, in other arrangements, the device 3400 can be used in non-closed, partially-closed, or open suction systems or applications, as desired or required. As shown, the illustrated device 3400 comprises a two-walled balloon structure at the cleaning portion 3410. Accordingly, as best depicted in the expanded orientation of the lower view in FIG. 5, the balloon structure distends inwardly and outwardly simultaneously when air or other fluid is delivered therein. In some embodiments, in order to accomplish this type of expansion, the suction catheter body 3402 is generally discontinuous. For example, in the illustrated embodiment, the catheter body 3402 comprises a proximal portion 3406 and a distal portion 3408 (e.g., along the opposite side of the cleaning portion 3410). In some embodiments, the discontinuous portions 3406, 3408 of the suction catheter body 3402 are connected by the balloon structures 3430, 3432. In some embodiments, the adjacent catheter body 3402 is constructed of silicone of 50 A-80 A durometer and the wiper or cleaning member 3440 of a higher durometer (for example, 55 A-85 A) with respect to the adjacent catheter body 3402. In this embodiment, the adjacent catheter body 3402 will collapse beneath the wiper or cleaning member 3440, thereby closing distal suction communication as fluid is applied until it is fully collapsed and the wiper or cleaning member 3440 begins to expand.

With continued reference to FIGS. 5A and 5B, the balloon or other distensible structure 3430 comprises an inner component 3432 and an outer component 3434. As shown, the outer component 3434 of the balloon 3430 comprises one or more wipers or other cleaning members 3440. In some embodiments, the cleaning members 3440 comprise one or more square or sharp corners or portions. However, in other arrangements, the cleaning members 3440 can comprise a rounded or smooth profile, as desired or required. This applies to the cleaning members of any of the devices disclosed herein or equivalents thereof. As with other inflatable embodiments of the cleaning portion disclosed herein, one or more pilot or inflation channels or passages 3460 within the catheter body 3402 and/or any other portion of the device 3400 can be used to selectively deliver a volume of air or other fluid (e.g., other gas, liquid, etc.) to at least partially inflate the balloon structure 3430. As illustrated in FIG. 5B, when fluid is injected through an inflation channel 3460, the cleaning portion 3410 is expanded by deploying the balloon structure 3430 inwardly toward itself and outwardly toward the inside wall of a body inserted tube (e.g., endotracheal tube).

According to some embodiments, inflation of the balloon structure 3430 results in the inner component of the balloon structure 3430 occluding the ability to apply suction distally of the cleaning portion 3410 (e.g., at or along the distal opening 3428 and/or the distal suction openings 3420). Simultaneously, the outer sleeve or outer portion 3434 of the balloon structure 3430 can contact the inside wall of the body inserted tube. Accordingly, in such circumstances, if suction is applied to the catheter device 3400 proximally with the cleaning member deployed, the suction is only active at the proximal suction openings 3424. Such a configuration can help maximize or otherwise enhance suction at proximal suction openings 3424 so that debris removed on withdrawal of the catheter device is more likely to be suctioned into the lumen of the catheter body 3402 itself. In some embodiments, the distal portion 3408 of the catheter body 3402 moves proximally when the cleaning portion 3410 is deployed or expanded. As with other embodiments disclosed herein, the depicted device 3400 can be used with suction only, deployment of the cleaning portion only and/or deployment of the cleaning member and the application of suction simultaneously, as desired or required. The occlusion of the lumen of the suction catheter device 3400 may be one example of a way to dynamically control suction within the suction catheter device 3400 between the proximal and distal suction openings 3420, 3424. Other means of providing dynamic suction control may also be used.

According to some embodiments, the balloon structure or other distensible member 3430 comprises one or more generally soft materials with memory and recoil characteristics such that when air or fluid is withdrawn from the balloon structure 3430, the cleaning portion 3410 returns to its collapsed position, immediately adjacent the suction catheter body 3402.

FIGS. 6A and 6B illustrate another embodiment of a suction catheter device 3500 similar to those described above with reference to FIGS. 5A and 5B. In fact, the balloon structure 3530 of the suction catheter device 3500 of FIGS. 6A and 6B comprises an identical or similar two-layer design as the device 3400 of FIGS. 5A and 5B, in that it includes an inner balloon component 3532 and an outer balloon component 3534.

With continued reference to FIGS. 6A and 6B, an outer sleeve 3538 is positioned along the exterior of the expandable balloon (e.g., along the outside of the outer component 3534) and is configured to be expanded together with the outer component. As shown, the outer sleeve 3538 comprises one or more wipers or other cleaning members 3540. In some embodiments, the cleaning members 3540 comprise one or more square or sharp corners or portions. However, in other arrangements, the cleaning members 3540 can comprise a rounded or smooth profile, as desired or required. This applies to the cleaning members of any of the devices disclosed herein or equivalents thereof. As with other inflatable embodiments of the cleaning portion disclosed herein, one or more pilot or inflation channels or passages 3560 within the catheter body 3502 and/or any other portion of the device 3500 can be used to selectively deliver a volume of air or other fluid (e.g., other gas, liquid, etc.) to at least partially inflate the balloon structure 3530 (e.g., the inner and outer balloon components 3532, 3534). As illustrated in FIG. 6B, when fluid is injected through an inflation channel 3560, the cleaning portion 3510 is expanded toward the inside wall of a body-inserted tube (e.g., endotracheal tube). Therefore, the outer sleeve 3538, which is positioned along the outside of the inner and outer balloon components 3532, 3534 can be "passively" expanded so that the cleaning members 3540 (e.g., wipers) attached or incorporated thereto engage the body-inserted tube (e.g., endotracheal tube) in order to selectively remove biofilm or other debris collected on an inner surface of the body-inserted tube.

According to some embodiments, the balloon 3530 and the passively expanding sleeve 3538 comprise generally soft materials with memory and recoil characteristics such that when fluid or air is withdrawn from the balloon 3530, the cleaning portion 3510 returns to its collapsed position, immediately adjacent the suction catheter body 3508.

FIGS. 7A-7C illustrate various views of a suction catheter device 3200, 3300, 3400, 3500 positioned within a body-inserted tube (e.g., endotracheal tube). As discussed herein, the device 3200, 3300, 3400, 3500 can be used in a closed suction system. For example, the device 3200, 3300, 3400, 3500 can be configured to retract within a flexible enclosure, either with or without a manifold (e.g., manifold 3010). In such systems, the catheter device 3200, 3300, 3400, 3500 can be selectively retracted into a sleeve (e.g., sleeve 3090 in FIG. 1). Accordingly, the biofilm, other debris and/or other unwanted materials removed from the subject being treated can be safely maintained within the sleeve and away from the exposed external environment, thereby allowing the clinician to reuse the device over a particular time period. Further, as discussed, the clinician is provided with great flexibility when using such a device 3200, 3300, 3400, 3500, as he or she can choose to use the device 3200, 3300, 3400, 3500 for suction only, for body-inserted tube cleaning only, for cleaning of portions of the respiratory tract or tree, and/or combinations thereof, as desired or required.

Proximal controllers for existing closed suction systems only control the opening and closing of the suction channel or lumen between the distal end of the suction catheter and the origin of the suction (e.g., a wall-mounted suction unit). In accordance with several embodiments, a proximal controller or control unit of an endotracheal tube and/or distal airway cleaning system (such as the systems described herein) advantageously controls both the operation of the suction capability of the catheter device (e.g., device 3200, 3300, 3400, 3500) and the operation of the expandable cleaning portion near the distal end of the catheter device.

In several embodiments, the proximal controllers of the suction catheter devices described herein independently control the suction and cleaning portion activation (e.g., expansion) functions, thereby allowing the suction to function independently, the cleaning portion to be activated and function independently, or both suction and the cleaning portion to be activated simultaneously, as desired or required. In some embodiments, the proximal controller or control unit comprises a locking mechanism to prevent inadvertent activation of the suction and/or deployment of the expandable cleaning portion. The locking mechanism may advantageously be easy to use and to interpret, thereby reducing user error and improving user satisfaction. Unintended activation of the suction could significantly decrease ventilator circuit pressures, volumes, and/or flows, each of which may potentially cause significant adverse effects on an intubated patient. Unintended deployment of the expandable cleaning member or portion could significantly obstruct the artificial airway (e.g., endotracheal or other body-inserted tube), which could potentially cause significant clinical deterioration if left deployed for an extended period of time. In some embodiments, the locking mechanism is incorporated into the proximal controller or control unit. A portion (e.g., operational guide) of the proximal controller or control unit may be rotational or otherwise transitional in 1, 2 or 3 steps or detents. For example, the operational guide may rotate between three rotation positions each corresponding to a different operational state. In such embodiment, the initial position corresponds to an operational state in which suction and activation of the cleaning member are both locked or prevented, the second position corresponds to an operational state that allows suction only (with activation of the cleaning portion being locked or prevented), and the third position corresponds to an operational state that allows activation of the cleaning member only (with suction being locked or prevented). In this embodiment, risk of severe negative pressures and major atelectasis can be minimized or otherwise reduced. The transitions between the positions may be effected by rotation or other transitional movement. For rotational embodiments, continued rotation beyond the third position may cause transition back to the first position in a full circle. In various embodiments, the operational guide advantageously facilitates audible, visual and/or tactile confirmation of a transition between operational states or positions. In some embodiments, both suction and cleaning member activation are prevented when the operational guide is in a transition between the first, second or third positions. The locking mechanism may prevent suction in the initial position, prevent activation (e.g., expansion) of the cleaning member in the second position and prevent suction in the third position. The positions and corresponding functions are interchangeable in various embodiments. In some embodiments, only two operational states exist (suction only and combined suction and cleaning member operation).

In accordance with several embodiments, a method for cleaning an endotracheal tube with the endotracheal tube and distal airway cleaning system comprises inserting a closed suction catheter (e.g., device 3200, 3300, 3400, 3500) through a multi-port adapter or manifold (e.g., manifold 3010) coupled to an endotracheal tube and then advancing the distal end of the suction catheter to the distal end of the endotracheal tube (e.g., as determined by lining up centimeter markings or other visual indicia on the suction catheter with corresponding marks or other visual indicia on the endotracheal tube). Markings may prevent against over-insertion and reduce the risk of damage to portions of the respiratory system (e.g., trachea). In some embodiments, suction alone is activated by the proximal controller and applied to the suction catheter as the suction catheter is withdrawn back through the manifold and into a cleaning chamber of the manifold. The first pass of the suction catheter with suction alone may remove some amount of loose and more easily suctionable material from the inside of the endotracheal tube. In some embodiments, a second pass of the suction catheter is performed such that the suction catheter is again inserted to the distal end of the endotracheal tube. In several embodiments, the cleaning portion of the suction catheter is then activated by the proximal controller, thereby expanding an expandable or distensible cleaning member of the cleaning portion to contact an interior surface of a body-inserted tube. Suction may or may not be applied as the suction catheter is again withdrawn through the multi-port adapter or manifold and into the cleaning chamber. In accordance with several embodiments, the first pass utilizing suction alone decreases the volume of debris or biofilm that is removed during the second pass, thereby decreasing the likelihood of contaminating or hindering the closed suction system module manifold by dragging a substantial volume of biofilm or other debris (e.g., several cubic centimeters) through the manifold 3010 en route to the cleaning chamber, or inadvertently depositing some amount of that debris within the manifold 3010 itself. In some embodiments, the cleaning portion of the suction catheter is activated without a prior suctioning pass. In this embodiment, suction is only used to clean the suction catheter after active cleaning. This embodiment may minimize or reduce derecruitment of the patient and can avoid potentially hazardous side effects of suctioning.

In accordance with several embodiments, the proximal controller is configured to be operated with a single hand while a second hand is used to stabilize the endotracheal tube and manifold 3010. In some embodiments, the second hand may also be used to turn a manifold valve (e.g., stopcock) 3060 between a closed and open position, or vice-versa. In some embodiments, the proximal controller includes a first activator to activate suction alone and a second activator to activate suction and to initiate distension or expansion of the distensible or expandable member of the cleaning portion of the suction catheter simultaneously, thereby facilitating clarity and ease of use, without any manipulation of the proximal controller between first and second passes.

Figure 8A:
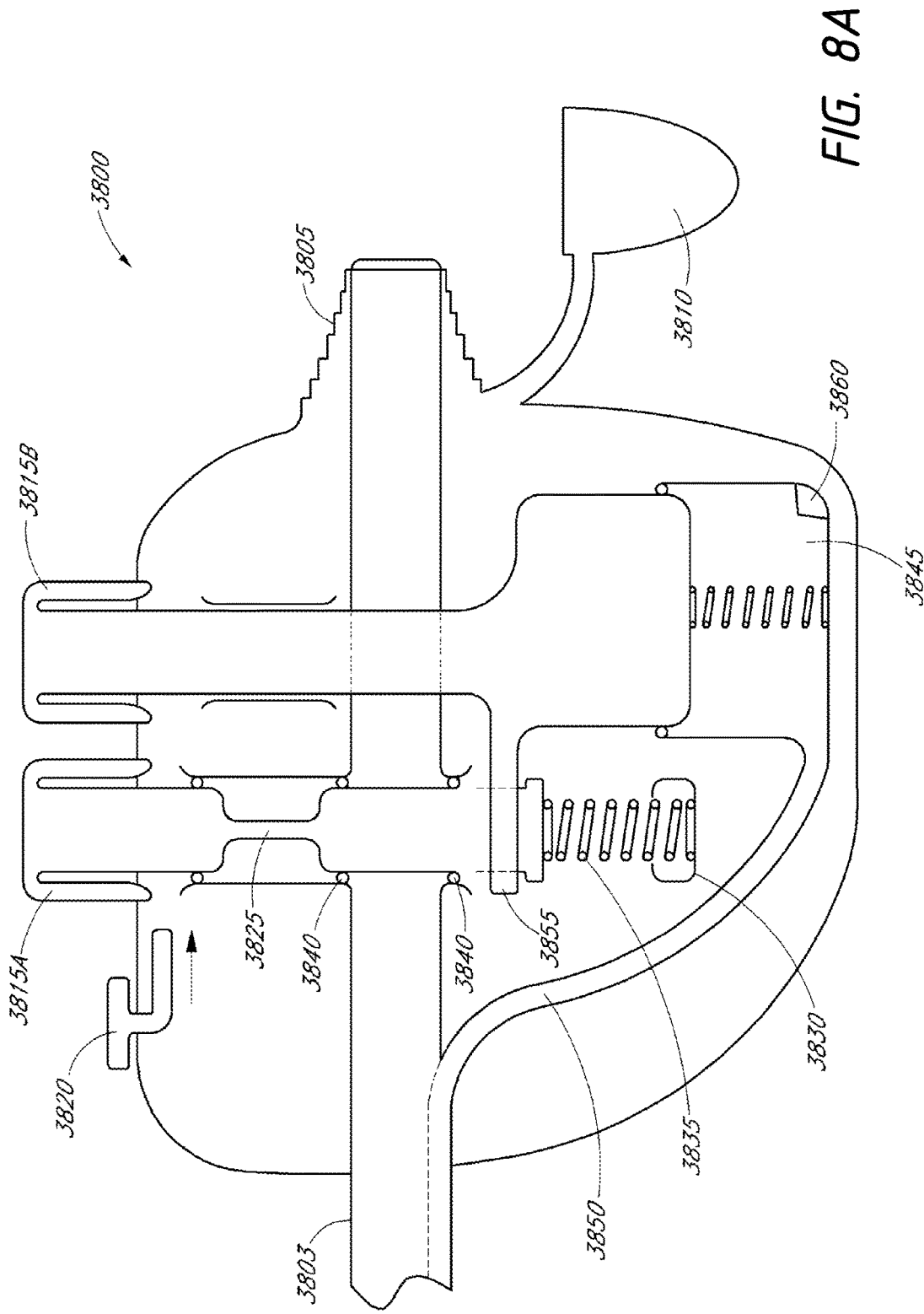
FIGS. 8A-8C, 9 and 10 illustrate embodiments of control mechanisms for the closed suction cleaning system of FIG. 1.

FIG. 8A illustrates a cutaway view of a schematic drawing of an embodiment of a proximal controller 3800 of a suction catheter of an endotracheal tube and airway cleaning system. As shown, a proximal portion of the suction catheter (e.g., device 3200, 3300, 3400, 3500) is received within the proximal controller 3800. The proximal portion of a suction channel 3803 traverses the proximal controller 3800 and terminates at a suction connector 3805 at the proximal end of the proximal controller 3800. In some embodiments, the suction connector 3805 comprises a standard connection for suction tubing coming from a suction source (e.g., wall suction unit). The suction connector 3805 may have a stepped profile as shown for connecting to suction tubing; however, other profiles and designs may be used. In some embodiments, the suction connector 3805 is configured to be covered at least temporarily by a cover or sealing member 3810 when suction tubing from a wall suction unit or other suction source is not connected to the suction connector 3805. In some embodiments, the cover or sealing member 3810 is configured to prevent against or reduce the likelihood of contamination and facilitate cleanliness and sterility. The cover or sealing member 3810 may comprise a tethered or non-tethered cap.

The proximal controller 3800, in some embodiments, comprises two activation members 3815A, 3815B that may be activated separately. As shown in FIG. 8A, the activation members 3815 may comprise plungers having a proximal portion external to a housing or shell 3802 of the proximal controller 3800 that is configured to be pressed by a clinician. Plunger 3815A is configured to control the operation of the suction capability of the suction catheter. Plunger 3815B is configured to control operation of both the suction capability and the operation (e.g., expansion and compression) of the distensible or expandable members of the cleaning portion of the suction catheter. The activation members 3815 may advantageously be operated by a single press of a finger. In some embodiments, the activation members 3815 are configured to be pressed and held to maintain suction and/or distension or expansion of structural components of the cleaning portion. In other embodiments (not shown) one or both of the activation members 3815 may have a retention mechanism (e.g., latch) that can be used to retain the activation members in the "active" state (either for a pre-determined time period or until released by a clinician). The proximal portions of the activation members 3815 exterior to the proximal controller 3800 may be shaped as buttons and/or may be sized and ergonomically shaped to facilitate being pressed by one or more fingers of a clinician. In some embodiments, the portions configured to be activated by a user comprise padding or other features configured to provide comfort and/or anti-slip features configured to improve grip and deter slipping. In some embodiments (not shown), the activation members 3815 are positioned on opposite sides of the housing or shell 3802.

The proximal controller 3800 may comprise a locking member 3820 configured to prevent or limit movement of the activation members 3815, thereby preventing distension or expansion of members of the cleaning portion of the suction catheter and/or activation of suction through the suction catheter. As shown, the locking member 3820 may be movable (e.g., slidable) between a "locked" position and an "unlocked" position. In some embodiments, the "locked" position corresponds to movement of the locking mechanism 3820 caudally until it engages underneath the periphery of the proximal portion of the activation member 815A. When in the "locked" position, neither activation member 3815A nor activation member 3815B can be depressed. When the locking member 3820 is in the "unlocked" position (e.g., when moved cephalad), each of the activation members 3815 can be depressed or otherwise activated.

In some embodiments, activation member 3815A comprises a narrow portion 3825 (e.g., a narrow cylindrical column having a substantially reduced diameter or other cross-sectional dimension compared to the adjacent portions of the main body of the activation member 3815A) that is sized and configured to be positioned within the suction channel 3803 when activation member 3815A is depressed and in an active state, thereby allowing suction and debris to pass through the proximal controller 3800 and into the suction tubing connected to the wall suction unit or other suction source. In some embodiments, the proximal controller 3800 comprises a stop 3830 that is configured to prevent further depression of activation member 3815A than is necessary. A spring 3835 or other elastic and/or resilient member may be attached to a distal end of activation member 3815A and to stop 3830 to restore activation member 3815A to its nominal "inactive" position when pressure or activation on activation member 3815A is released, thereby effectively closing the suction channel 3803. In some embodiments, the proximal controller 3800 comprises sealing members 3840 (e.g., O-rings) at the connection points to the suction channel 3803 within the proximal controller 3800 that are configured to provide an effective seal to reduce the likelihood of or prevent loss of pressure or air leakage during suctioning and/or to reduce the likelihood of or prevent against internal contamination.

Activation member 3815B may comprise an external proximal portion configured to be pressed (e.g., a button-like member), a main body and a distal portion configured to initiate deployment of an expandable cleaning portion of the suction catheter. In some embodiments, when activation member 3815B is activated or pressed, the distal portion of activation member 3815B compresses a volume of gas, fluid or liquid within a reservoir 3845 that is forced into a pilot channel portion 3850 and then into a pilot channel (e.g., air or fluid infusion or inflation channel 3260, 3360, 3460) extending along a length of the catheter device (e.g., device 3200, 3300, 3400, 3500). The size and shape of the distal portion of activation member 3815B is configured to correspond to the size and shape of the reservoir 3845 such that movement of the distal portion of activation member 3815B within the reservoir 3845 forces the air or fluid from the reservoir 3845 into the pilot channel portion 3850. The pilot or inflation channel or passage of the suction catheter may be connected to (e.g., in fluid communication with) an air- or fluid-activated distensible or expandable member or portion of the suction catheter (such as the balloons or other distensible members described above), thereby causing distension or expansion of the distensible or expandable members.

In some embodiments, activation member 3815B comprises an extension 3855 with a cutout or aperture that is configured to receive the distal portion of activation member 3815A. The cutout or aperture is sized such that when the extension 3855 moves when activation member 3815B is pressed, the extension 3855 engages a flange at the distal end of activation member 3815A, thereby causing movement of activation member 3815A toward stop 3830. Accordingly, activation of activation member 3815B effectively controls both suction and deployment of the distensible or expandable member of the suction catheter simultaneously with a single activation action (e.g., press of a button or button-like member). When the proximal end of activation member 3815A is pressed, the distal portion of activation member 3815A can freely slide within the cutout or aperture of extension 3855. In some embodiments, the proximal controller 3800 comprises a stop 3860 configured to prevent over-insertion of activation member 3815B.

If the occasion arises that a clinician wishes to activate the cleaning portion (e.g., cleaning member) of the suction catheter alone, suction tubing can be removed from suction connector 3805 or effectively clamped, thereby disabling the suction capability. Depressing activation member 3815B with the suction tubing clamped or removed results in expansion of the distensible or expandable member of the cleaning portion of the suction catheter without suction being activated (even though activation member 3815A is depressed).

Figures 8B, 8C:
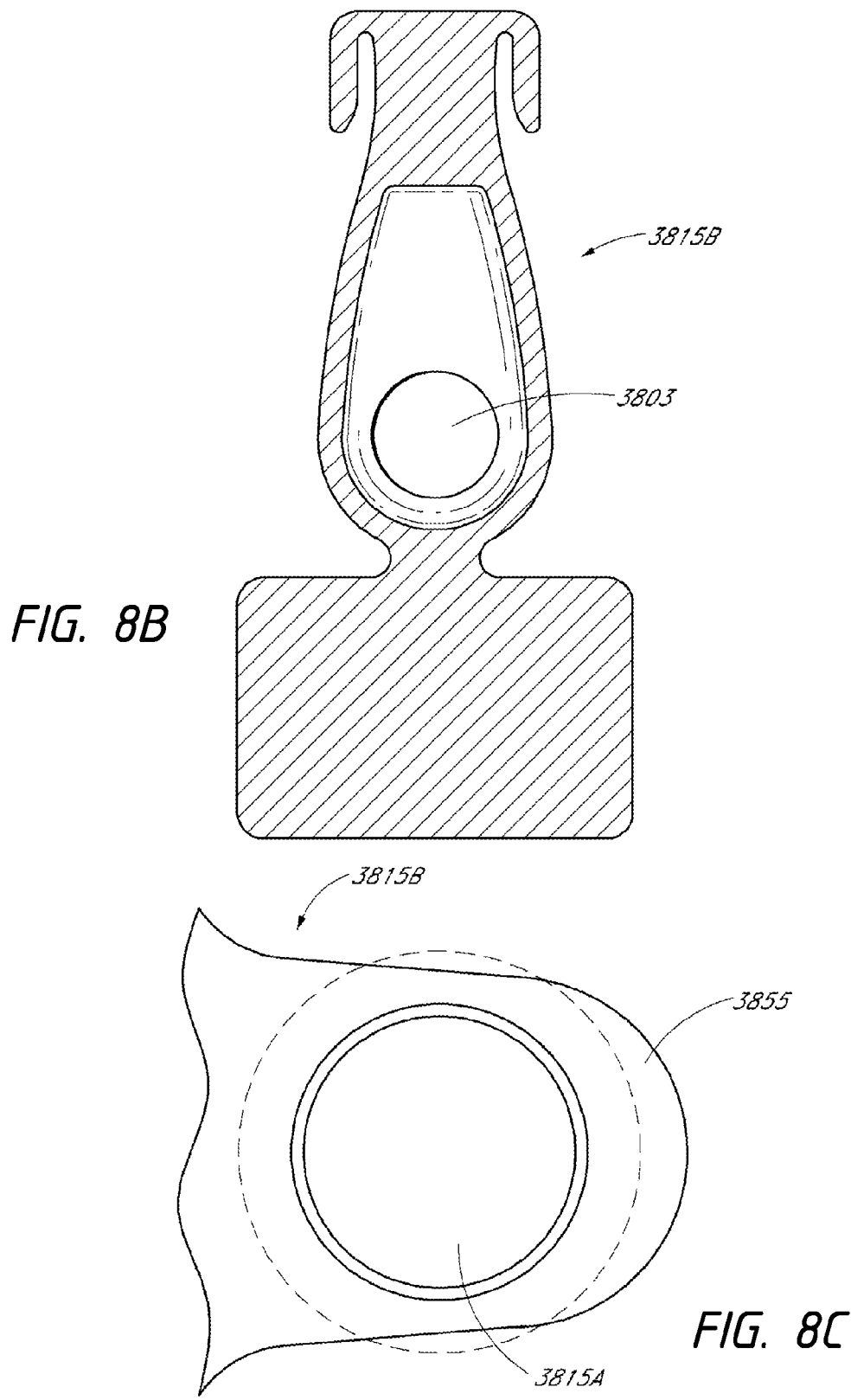

FIG. 8B illustrates a cutaway view of activation member 3815B viewed from a position posterior to the proximal controller 3800. As shown, activation member 3815B comprises a cutout portion or aperture in the main body that is sized and shaped such that activation member 3815B can move across its entire range of motion without interference from, or interfering with, the suction channel 3803.

FIG. 8C illustrates a top view of the overlapping portions of activation member 3815B and activation member 3815A. Activation member 3815A extends through the cutout or aperture of the extension 3855 of activation member 3815B such that a flange on the distal end of activation member 3815A is engaged by movement of activation member 3815B (as described in connection with FIG. 8A).

Figure 9:
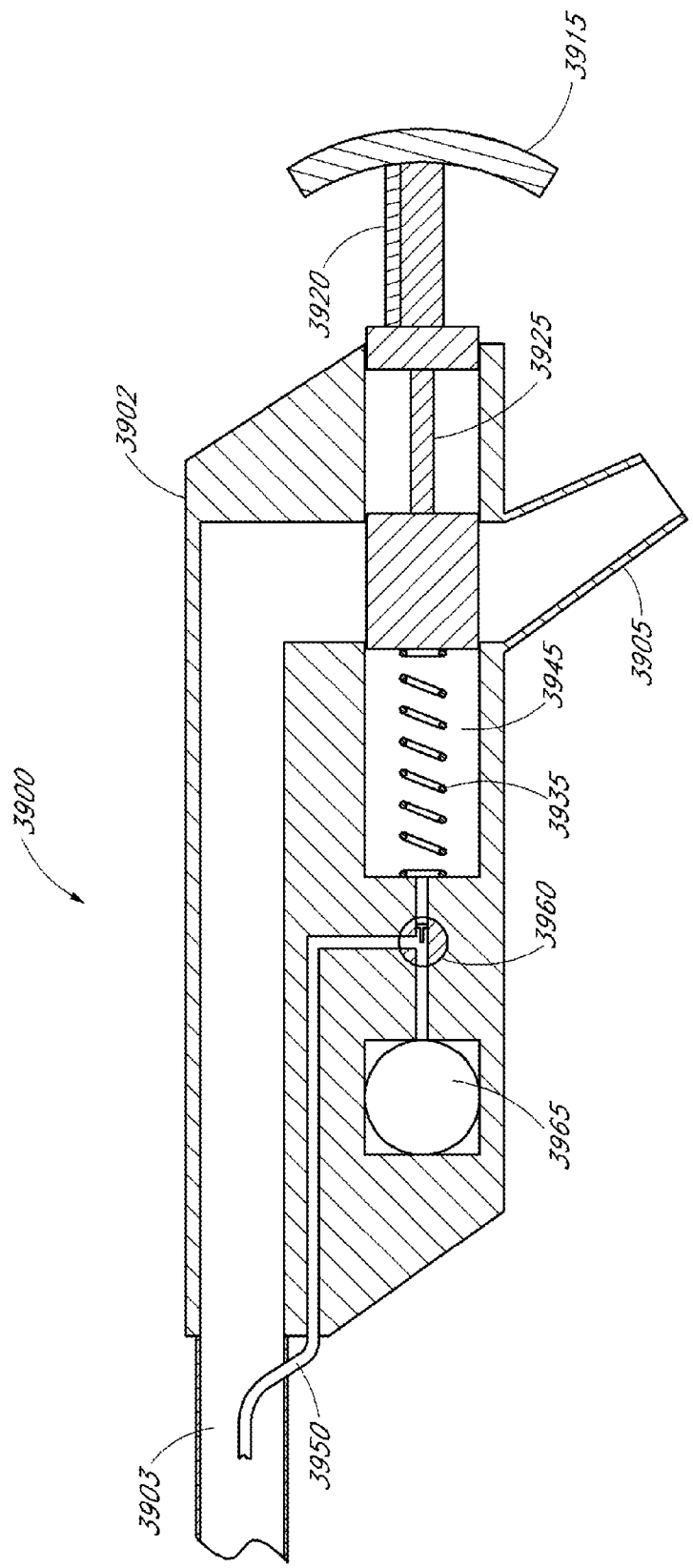

In some embodiments, the proximal controller or control unit comprises a single actuation mechanism that simultaneously activates suction and distension or expansion of the cleaning portion but that requires a secondary maneuver to allow the two actions to occur individually if desired. FIG. 9 is a cutaway longitudinal representation of an alternative embodiment of a proximal controller 3900. The proximal controller 3900 comprises a housing or shell 3902, a suction connector 3905, an activation member 3915, a locking member 3920, a spring 3935 or other elastic and/or resilient member, a first air or fluid reservoir 3945, a pilot channel portion 3950, a flow-regulating member 3960, and a second air or fluid reservoir 3965. In some embodiments, the suction channel of the suction catheter is configured to interface with the proximal controller 3900, with the proximal controller comprising a passageway between the suction channel or lumen of the suction catheter to the suction connector 3905. Suction tubing may be connected to the suction connector 3905 and to a wall suction unit or other suction source.

In some embodiments, activation member 3915 comprises a plunger with a rotatable locking member 3920 configured to prevent activation member 3915 from moving when desired and/or required. The activation member 3915 comprises a narrow portion 3925 sized and positioned along the length of the body of the activation member 3915 such that, when a proximal portion of the activation member 3915 is depressed, the narrow portion 3925 (e.g., central column) moves into the suction channel 3903, thereby allowing suction and debris to pass through the suction catheter, around the narrow portion 3925, and into the suction tubing attached to the suction connector 3905.

As described above in connection with FIGS. 8A-8C, actuation of activation member 3915 causes the injection of air or fluid from the reservoir 3945 into the pilot channel portion 3950 and then into a pilot or inflation channel or passage extending along a length of the suction catheter. The pilot channel is connected to a distensible or expandable member of the cleaning portion of the suction catheter such that actuation of the activation member 3915 effects deployment of the distensible or expandable member. The flow-regulating member 3960 may comprise a stopcock, valve, or other flow control mechanism that allows activation member 3915 to inject air or fluid into the expandable cleaning portion through the pilot or inflation channel when in an "open" position. When the flow regulating member 3960 is in a "closed" position, depression of the proximal button of activation member 3915 results in the reservoir 3945 being discharged into the inner space of the controller housing 3902 or into the second reservoir 3965 and not into the distensible or expandable members of the cleaning portion of the suction catheter, thereby allowing suction to be activated individually without activation of the cleaning portion. Upon release of activation member 3915, spring 3935 forces activation member 3915 back into its neutral "inactive" position. In some embodiments, the second reservoir 3965 comprises an elastic reservoir and the fluid or air within the second reservoir 3965 is simultaneously emptied back into the first reservoir 3945 as activation member 3915 returns to its neutral position.

In some embodiments, an endotracheal tube cleaning method using the proximal controller 3900 could occur in two passes as follows: First, valve member 3960 may be toggled (e.g., turned, switched) to a "closed" position so that depression of activation member 3915 discharges the air or fluid from the first reservoir 3945 into the housing or shell 3902 or into the second reservoir 3965 of the proximal controller 3900 and not into the pilot or inflation channel of the suction catheter. The suction catheter may then be inserted to the distal end of the endotracheal tube as determined by aligning centimeter markings or other visual indicia on the suction catheter with corresponding markings or other visual indicia on the endotracheal tube. In some embodiments, activation member 3915 is then depressed to activate suction and the suction catheter is withdrawn through the manifold 3010 and into a cleaning chamber. For the second pass, flow regulating member 3960 may be toggled (e.g., turned, switched) to the "open position" such that depression of activation member 3915 discharges reservoir 3945 into the cleaning portion of the suction catheter. The suction catheter could again be inserted to the distal end of the endotracheal tube. In some embodiments, activation member 3915 is then depressed (e.g., until it engages stop 3930), thereby simultaneously activating suction and distension or expansion of the cleaning portion of the suction catheter. The suction catheter may then be withdrawn through the manifold 3010 and into the cleaning chamber or into the sleeve or enclosure of a closed suction system.

Figure 10:
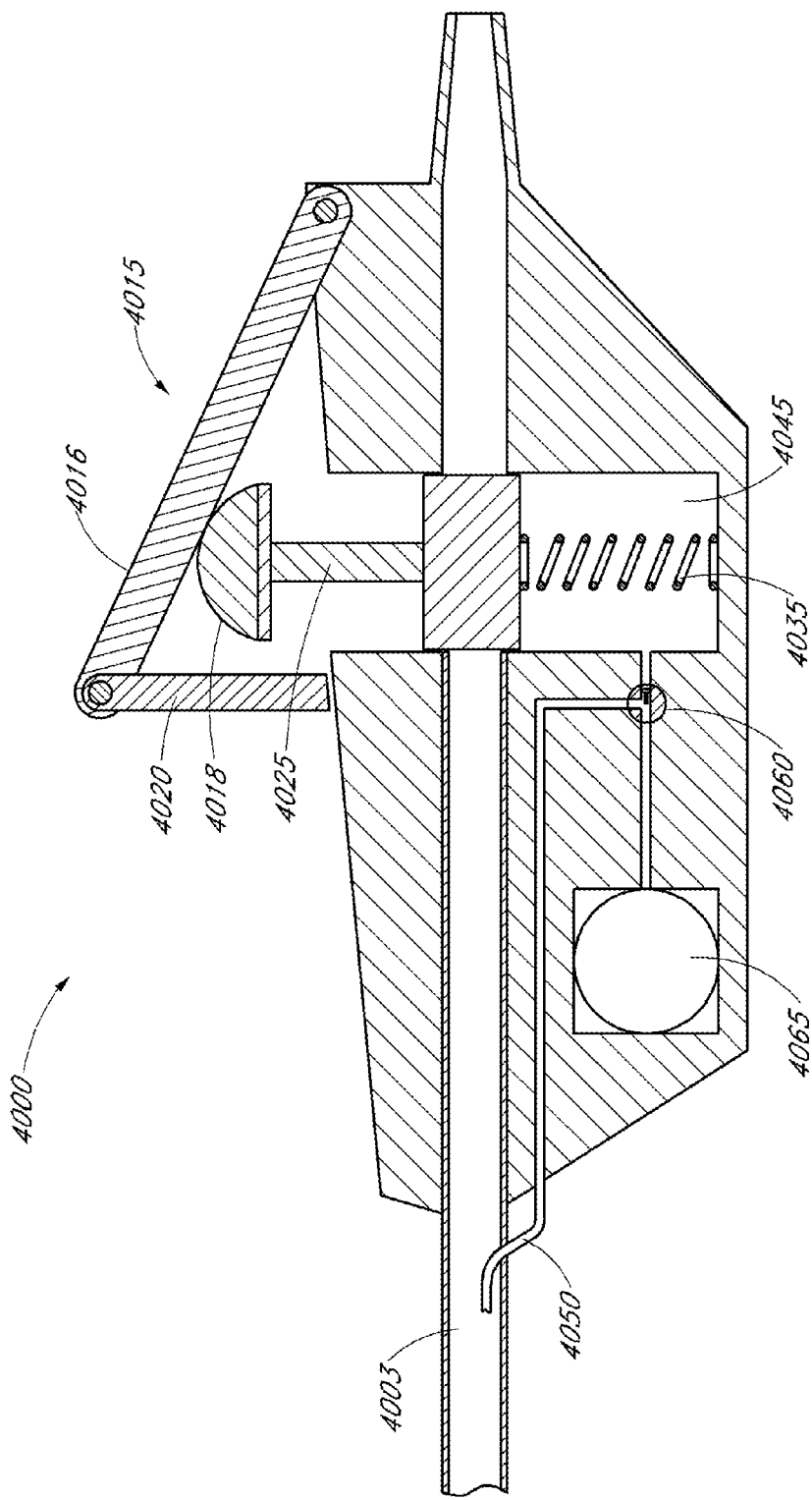

FIG. 10 illustrates a cutaway longitudinal view of another embodiment of a proximal controller 4000. The proximal controller 4000 comprises a housing or shell 4002, a suction connector 4005, an activation member 4015, a locking member 4020, a spring 4035 or other elastic and/or resilient member, a first air or fluid reservoir 4045, a pilot channel portion 4050, a flow regulating member 4060, and a second air or fluid reservoir 4065. As shown, the suction connector 4005 may be aligned with the suction channel of the suction catheter. In some embodiments, the activation member 4015 comprises an activating lever 4016 and a plunger 4018. The plunger 4018 may comprise a narrow portion 4025 (e.g., central supporting column) that is sized and positioned to align with the suction channel when the plunger 4018 is depressed into an "active" position. The locking member 4020 may be connected to a distal end of the activating lever 4016 and to the housing or shell 4002 and may be configured to prevent depression of the plunger 4018 by the activating lever 4016 when in a "locked" position. The flow regulating member 4060 may comprise a stopcock, valve, or other flow control structure.

In some embodiments, an endotracheal tube cleaning method using the proximal controller 4000 could occur in two passes as follows. First, flow regulating member 4060 is toggled (e.g., turned, switched) to a "closed" position such that depression of the plunger 4018 would discharge reservoir 4045 into the housing or shell 4002 or into the second reservoir 4065 of the proximal controller 4000. The suction catheter could then be inserted to the distal end of the endotracheal tube by lining up centimeter markings or other visual indicia on the suction catheter with corresponding markings or other visual indicia on the endotracheal tube. In some embodiments, activating lever 4016 is then depressed, causing plunger 4018 to move inferiorly so that the narrow portion 4025 of plunger 4018 is positioned and comes to rest within the suction channel 4003. The positioning of the narrow portion 4025 within the suction channel 4003 allows suction and debris to flow through suction channel 4003, around narrow portion 4025, and into suction tubing attached at the suction connector 4005. With activating lever 4016 depressed, the suction catheter is then withdrawn through the manifold 3010 and into the cleaning chamber. Release of activating lever 4016 allows spring 4035 to return the activating lever 4016 to its neutral "inactive" position. In some embodiments, the second reservoir 4065 comprises an elastic reservoir and the fluid or air within the second reservoir 4065 is simultaneously emptied back into the first reservoir 4045 as activation lever 4016 returns to its neutral position.

For the second pass, flow control member 4060 is toggled (e.g., turned, switched) to the "open" position such that depression of plunger 4018 causes displacement of the air or fluid in reservoir 4045 to move into the pilot or inflation channel of the suction catheter and then into the distensible or expandable members of the cleaning portion. In some embodiments, the suction catheter is again inserted to the distal end of the endotracheal tube with corresponding centimeter markings or other visual indicia aligned. Activating lever 4016 may then be depressed, thereby causing both expansion of the expandable cleaning portion and application of suction to the suction catheter. The suction catheter may then be withdrawn through the manifold 3010 and into the cleaning chamber or a sleeve or enclosure of a closed suction system.

In accordance with several embodiments, the closed suction system module (3070, 3080, 3090) is interchangeable with other modules or adapters. For example, a visualization device module (e.g., bronchoscopic visualization and/or suction module) may be connected to the proximal end of the manifold 3010 after removal of the closed suction coupling 3070. The visualization device module may be configured to operate in a closed suction system environment (e.g., with a sleeve or enclosure surrounding the visualization device, such as sleeve 3090 of FIG. 1) or a non-closed or open suction system environment (e.g., without a sleeve or enclosure).

Figure 11A:
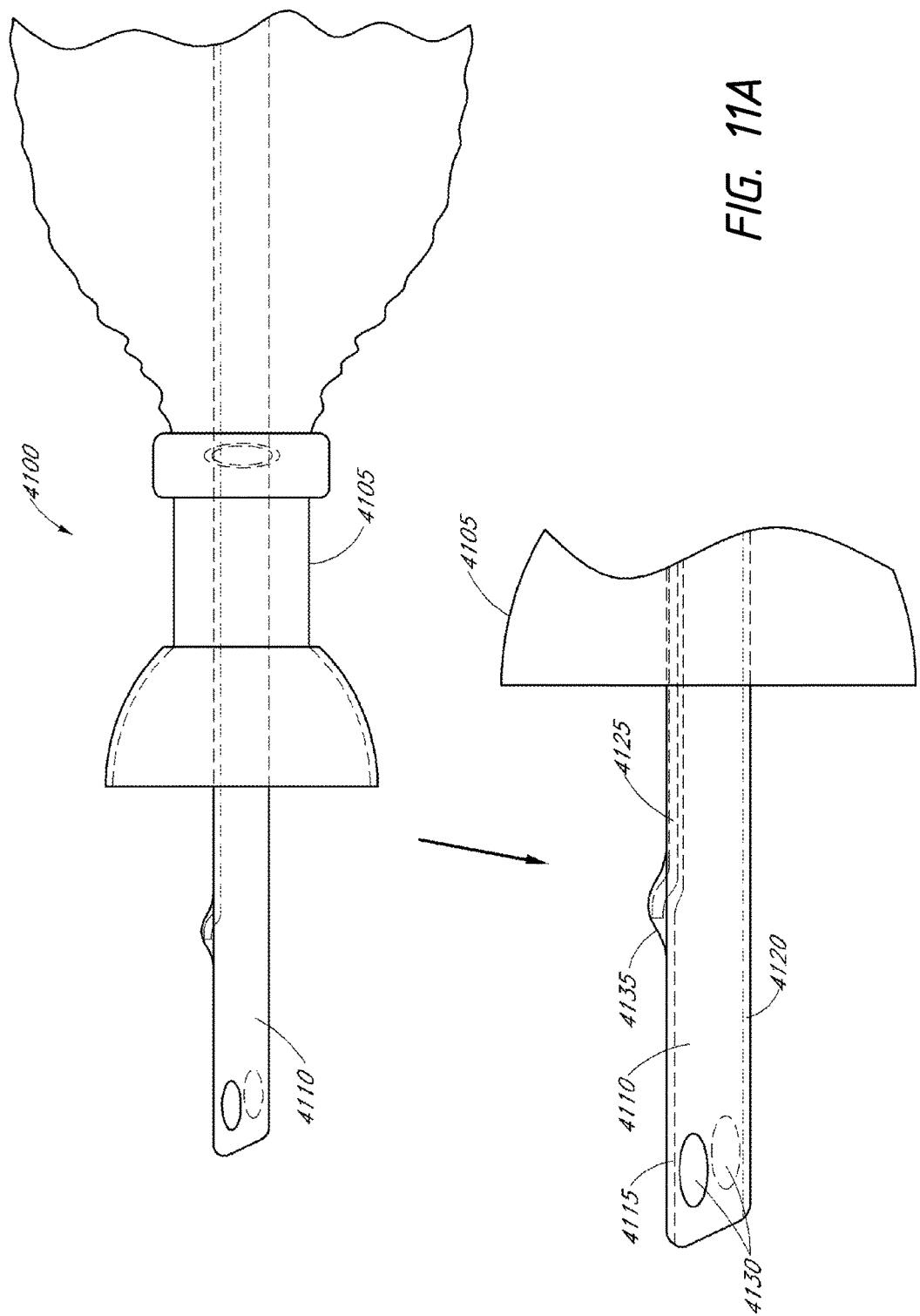
Figure 11B:
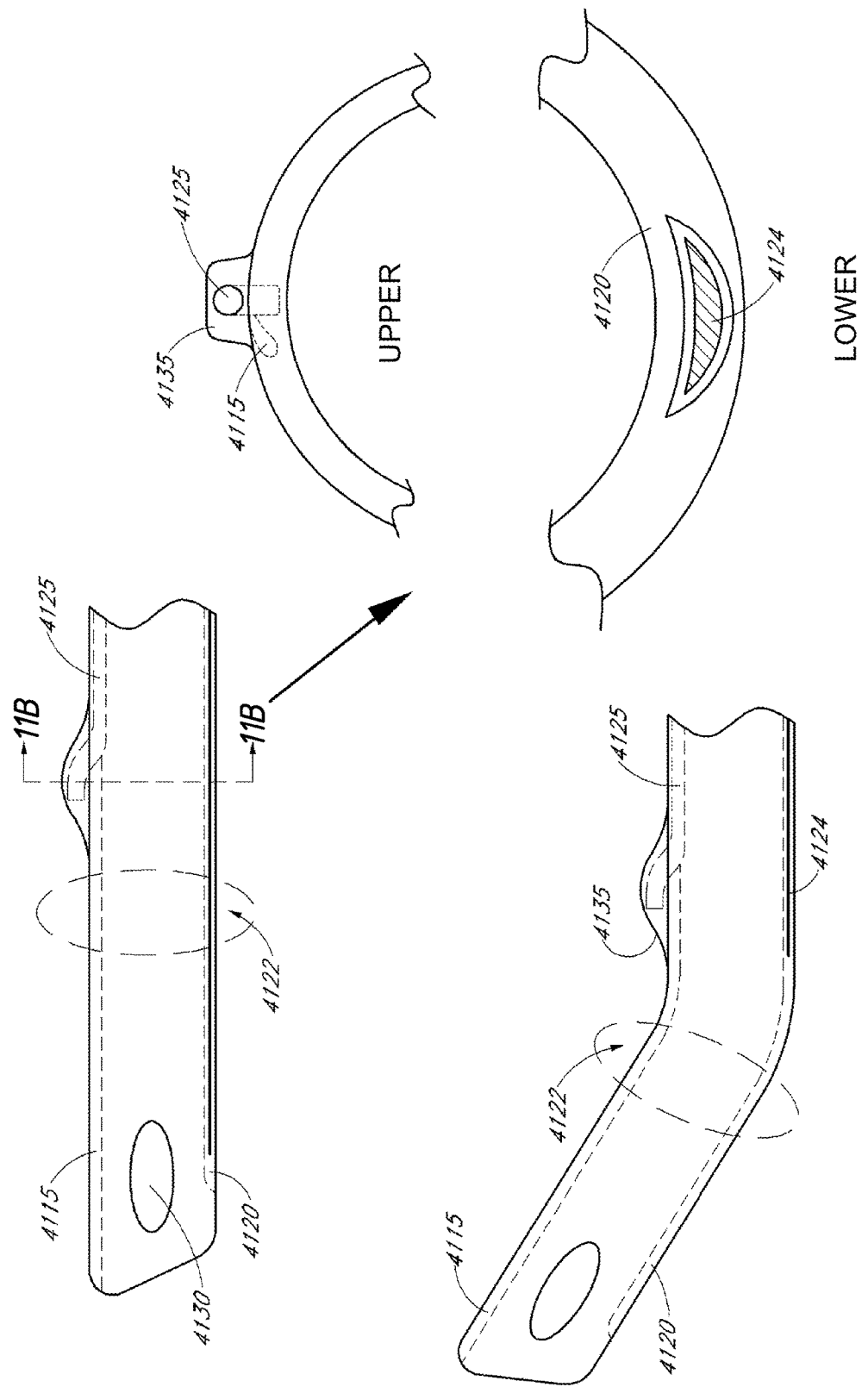

FIGS. 11A-11C illustrates an embodiment of a visualization device module 4100 configured to be coupled to the proximal port of manifold 3010. In some embodiments, the visualization device module 4100 comprises a closed suction modular adapter that includes a closed suction assembly 4105 and a distal airway cleaning device (e.g., a suction catheter) 4110. In some embodiments, the visualization device module 4100 comprises a standalone bronchoscopic replacement device. The closed suction assembly 4105 may comprise a coupling member for connecting to the proximal port of the manifold 3010 and a sleeve or enclosure coupled to the coupling member and extending proximally to enclose or sheath the distal airway cleaning device 4110 (e.g., similar to the sleeve or enclosure 3090 of FIG. 1). The distal airway cleaning device 4110 may comprise any of the structural features of the distal airway cleaning devices and/or suction catheters described herein or disclosed herein, including the visualization, suctioning, cleaning, irrigation and steerability features.

Visual inspection of the endotracheal tube and distal airways of an intubated patient, clearing of pooled secretions within the lungs, visual guidance into specific segments for diagnostic bronchioalveolar lavage (BAL), and visual guidance for percutaneous tracheostomy are typically performed in the intensive care unit (ICU) setting using a fiber-optic bronchoscope. The bronchoscopes are predominantly reusable and require cleaning, reprocessing, and resterilization between uses. The cleaning and sterilization process removes the bronchoscope from availability for at least a few hours. Because of all the internal components and channels within a reusable bronchoscope, sterility is difficult if not impossible to achieve. Existing bronchoscopes have relatively small suction channels (e.g., less than 3 mm) that provide less than ideal suction capability while at the same time being housed in an overall outside diameter (typically 6 mm or greater) that causes at least partial and sometimes quite significant obstruction of an artificial airway (e.g., endotracheal or other chest drainage tube) when the bronchoscope is in place. In accordance with several embodiments, the distal airway cleaning device 4110, either as a standalone bronchoscopic replacement or as part of a closed suction visualization module, advantageously provides constant availability, avoids reprocessing and sterilization, provides a superior suction channel compared to existing bronchoscopes (e.g., greater than 3 mm), and maintains a maximum outside diameter that reduces obstruction of the artificial airway (e.g., less than 5.5 mm).

In some embodiments, the visualization device module 4100 is configured to replace the closed suction system module (3070, 3080, 3090). The distal airway cleaning device 4110 comprises a suction catheter having an irrigation channel 4115, a steerability channel 4120, a visualization channel 4125, and suction holes or apertures 4130 near the distal end of the suction catheter. The irrigation channel 4115 may be used for bronchioalveolar lavage. In some embodiments, the steerability channel 4120 is configured to receive a rigid or stiff member (e.g., ribbon wire) that can be moved longitudinally within the steerability channel 4120 in order to facilitate flexion or extension of the catheter tip, as will be described in more detail in connection with FIG. 11B. The visualization channel 4125 may be configured to receive a visualization or imaging member (e.g., a fiber-optic scope). In some embodiments, the distal airway cleaning device 4110 comprises a ramped projection 4135 at a location corresponding to a distal end of the visualization channel 4125. The ramped projection 4135 may comprise an optical window. The optical window may comprise any of the structural properties or features of the windows or lenses described herein.

In some embodiments, when the visualization device module 4100 is connected to the manifold 3010, the distal airway cleaning device 4110 is introduced through the manifold 3010 and advanced into the endotracheal tube, and then distally into the more distal airways (e.g., bronchi or other lung fields). The distal airway cleaning device 4110 may advantageously provide visual diagnosis of endotracheal tube position and degree of obstruction, and/or status of the distal airways, visually directed bronchioalveolar lavage capability, improved suction capability of pooled secretions (e.g., due to increased diameter of the suction channel), and/or visualization for percutaneous tracheostomy or other procedures. In accordance with several embodiments, the visualization device module 1100 advantageously provides a visualization device (e.g., bronchoscopic device) that may be inserted within artificial and/or native airways (including the respiratory tree) of a patient within a closed suction environment (e.g., within a sleeve or enclosure). The visualization device may also include suctioning capabilities in addition to visualization capabilities. Because the visualization device module is configured to facilitate insertion of the re-usable visualization device (e.g., bronchoscope or fiber-optic scope) within a closed suction environment, the visualization device may be re-used within a shorter period of time than if the visualization device was not inserted within a closed suction environment and may be used without breaking the ventilation connection to remove an adapter connected to the endotracheal tube. In addition, because the visualization device module is configured to facilitate insertion of the reusable visualization device (e.g., bronchoscope or fiber-optic scope) within a sealed disposable component, the reusable visualization device may be re-used within a shorter period of time than a regular bronchoscope because it does not require high-level disinfection or sterilization between uses (e.g., less than one minute, less than two minutes, less than five minutes, less than ten minutes, less than twenty minutes, less than thirty minutes, less than an hour).

FIG. 11B illustrates more detailed views of the distal end of the distal airway cleaning device 4110. In some embodiments, a flexible portion 4122 of the suction catheter near the distal end of the distal airway cleaning device 4110 is an area of the suction catheter that is preformed to have an angulation of between 30° and 60°. In some embodiments, the angulation may facilitate advancement into bronchial segments or other distal airway passages. A longitudinal steering member 4124 (e.g., a stiff or rigid metal ribbon wire) may be advanced longitudinally in the steerability channel 4120 and, when advanced beyond the preformed flexible portion 4130, may straighten out the distal end of the suction catheter to approximately 0° to achieve the lowest profile possible. The straight profile may be desired and/or required during insertion of the distal airway cleaning device 4110 through the manifold 3010 and endotracheal tube. Proximal withdrawal of the longitudinal steering member 4135 within the steerability channel 4120 allows the catheter to resume the preformed tip angulation (e.g., for manipulation into segmental bronchi). The longitudinal steering member may be lubriciously coated, such as with a parylene coating. The lubricious coating may be integral with or bonded to the longitudinal steering member. The steering features described herein can also be adapted for use in the distal airway cleaning devices described herein.

FIG. 11B includes a cross-section view of the distal airway cleaning device 4110 taken along section line 11B-11B. In some embodiments, the irrigation channel 4115 comprises a side channel configured to be used to flush the window at the distal end of the visualization channel 4125. In other embodiments, the suction catheter of the distal airway cleaning device 4110 comprises a separate stand-alone flushing channel within the wall of the suction catheter in addition to the irrigation channel 4115. As described above in connection with FIG. 11A, the distal airway cleaning device may comprise a ramp-like protrusion or recess 4135 for the optical window at the end of the visualization channel 4125. In some embodiments, the protective protrusion or recess 4135 is smooth, without sharp edges, in order to avoid "hang-ups" during passage of the distal airway cleaning device or tissue injury as a result of direct contact.

In several embodiments, the distal airway cleaning device 4110 is configured to be used without being housed in the closed suction system 4105 (e.g., as a standalone device). For example, the distal airway cleaning device 4110 may be used without the protective flexible sheathing of the closed suction system similar to the way bronchoscopy has previously been practiced. In various embodiments, the distal airway cleaning device 4110 is configured to be inserted through any standard bronchoscopic adapter and may be compatible with any suction system (e.g., open or closed) into which a bronchoscopic adapter could be inserted.

Use of the distal airway cleaning device 4110 within the visualization device module 4100 advantageously facilitates cleaning of the distal tip of the distal airway cleaning device 4110 without removing it from the ventilatory circuit, allows for avoidance of the need for sterile gloves to perform visualization (e.g., bronchoscopic) procedures as the sheath of the closed suction system 4105 prevents direct hand or clean glove contact with the distal airway cleaning device 4110, and improves protection of healthcare workers and the environment from contamination by potentially infectious secretions and debris removed from the endotracheal tube and lungs during the procedure. After completion of the procedure, the visualization device module 4100 may be removed and the closed suction coupling 3070 may be reconnected.

Turning to FIG. 12, other adapters may be connected to the manifold 3010 to facilitate other diagnostic, cleaning or other therapeutic procedures to be performed that do not require a closed suction system or cannot be performed with the closed suction coupling 3070 in place. The other adapters may be coupled to the manifold 3010 without requiring removal of the manifold 3010 and without requiring temporary disconnection from a ventilator. FIG. 12 illustrates an embodiment of an adapter 4200 that is configured to be connected to the manifold 3010 to allow placement of multiple instruments and/or devices into an endotracheal tube or other chest drainage tube (artificial airway) and/or the respiratory system (natural airways). The instruments and/or devices to be inserted through the adapter 4200 may include bronchoscopes, endotracheal tube cleaning devices such as those described herein, bronchioalveolar lavage catheters, plain suction catheters, or other devices that would fit through an endotracheal tube or other body-inserted tube (e.g., instruments or devices having a maximum diameter of 9 mm).

FIG. 12 illustrates the proximal end of the manifold 3010 of FIG. 1 with the closed suction coupling 3070 removed. The adapter 4200 comprises a connection member 4201 configured to secure the adapter 4200 to the manifold 3010, a tubular body 4202, a valve 4203, a diaphragm 4204, and a cap 4205. The connection member may be configured to secure the adapter 4200 to the manifold 3010 by friction-fit coupling, snap-fit coupling, threaded coupling, adhesive coupling, or other removable coupling means. In some embodiments, the tubular body 4202 has a minimum inner diameter configured to substantially correspond to (e.g., be slightly smaller than) the inner diameter of the proximal end of the manifold 3010. For example, the inner diameter of the tubular body 4202 may be about 7 mm, 8 mm, 9 mm, 10 mm, 11 mm, 12 mm, etc. depending on the inner diameter of the proximal end of the manifold 3010. In some embodiments (not shown), an irrigation port comprising a cap is coupled to the tubular body 4202. In this embodiment, instruments (such as instruments with suction capability) can be cleaned by irrigating with saline while portions of the instruments are positioned within the adapter 4200.

The valve 4203 may comprise a "flap valve" that is configured to easily move out of the way upon device or instrument insertion but that is configured to completely cover the diaphragm 4204 upon device or instrument removal. In several embodiments, the valve 4203 advantageously limits or prevents against loss of positive pressure from the ventilatory circuit when the adapter 4200 is in place but no device or instrument inserted and the cap 4205 is open. In one embodiment, the diaphragm 4204 is a soft, flexible diaphragm that allows insertion of devices or instruments in the range of about 2 mm to 7 mm (e.g., 2 mm, 2.5 mm, 3 mm, 3.5 mm, 4 mm, 4.5 mm, 5 mm, 5.5 mm, 6 mm, 6.5 mm, 7 mm) but also closes down around the shaft of the device or instrument in such a way as to provide an effective seal to limit or prevent loss of positive pressure from the ventilatory circuit. The cap 4205 may be tethered to the adapter 4200. In some embodiments, the cap 4205 is not tethered to the adapter. The cap 4205 may be coupled to the adapter 4200 by threaded coupling, friction-fit coupling, snap-fit coupling, adhesive coupling, or other removable coupling means. In some embodiments, the cap 1205 is configured to be placed over the diaphragm 4204 and flap valve 4203 when no device or instrument insertion procedure is being utilized (e.g., to further prevent against loss of positive pressure and/or to prevent against contamination).

FIG. 13 illustrates a sealing member 4300 that is configured to be inserted within the closed suction system module (3070, 3080, 3090) upon removal of the closed suction coupling 3070 from the proximal end of the manifold 3010. In one embodiment, the sealing member 4300 comprises a removable cap. The sealing member 4300 may advantageously keep the distal end of the closed suction system module clean during the period of time the closed suction system module is removed in favor of other adapters or modules (e.g., visualization device module 4100 or adapter 4200). For example, the closed suction system module might be removed temporarily to allow placement of the adapter 4200 in a patient that is scheduled to undergo bronchoscopy. In some embodiments, the sealing member 4300 is configured to be placed over or within the closed suction coupling 3070 while the closed suction system module is set aside during the time that a bronchoscope or other instrument is being used for a diagnostic, visualization, cleaning or other therapeutic procedure. In some embodiments, at the end of the bronchoscopic or other procedure, the adapter 4200 is removed, the sealing member 4300 is removed from the closed suction coupling 3070, and the closed suction coupling 3070 is reconnected to the manifold 3010. In accordance with several embodiments, the valve member 3060 (e.g., stopcock) of the manifold 3010 advantageously allows these maneuvers and the device substitutions to be performed without opening the ventilation circuit, thereby allowing for maintenance of positive pressure at all times during any substitution of devices or connections to the proximal end of the manifold 3010. In some embodiments, the sealing member 4300 uses the same coupling mechanism as the closed suction coupling 3070 to the manifold 3010.

Figure 14A:
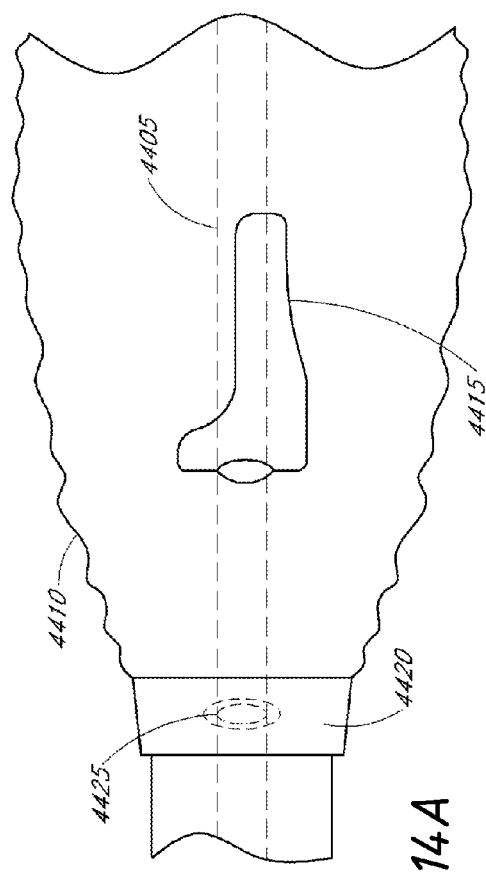
FIGS. 14A-14C illustrate various views of a schematic representation of a closed suction system.
Figure 14C:
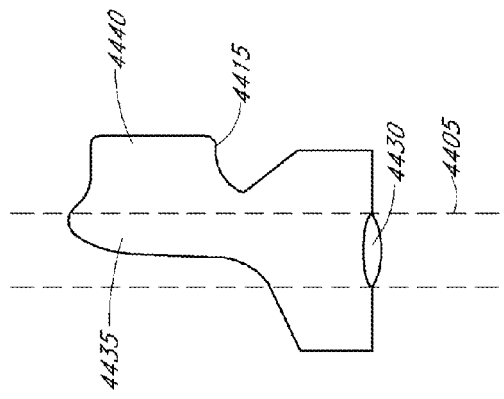
Figure 14B:
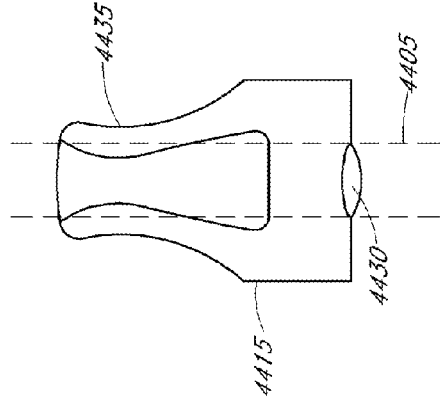

FIGS. 14A-14C illustrate various views of a schematic representation of a closed suction system 4400 comprising a suction catheter 4405, a flexible sheath 4410, a stop member 4415, and a coupling member 4420. The coupling member 4420 comprises a diaphragm or other sealing barrier member 4425. Such a diaphragm 4425 can be configured to advantageously permit the suction catheter 4405 to be inserted and removed therethrough while maintaining or substantially maintaining a seal. Accordingly, no loss or substantially no loss of positive pressure in the ventilatory circuit can occur while the clinician is using the suction catheter 4405 in a closed suction system. The stop member 4415 can be variably positioned along a length of the suction catheter 4405 so that the depth of insertion of the suction catheter 4405 can be mechanically and visually controlled.

In FIG. 14A, the stop member 4415 is shown snapped onto the suction catheter 4405. In accordance with several embodiments, as the suction catheter 4405 is inserted into a body-inserted tube (e.g., endotracheal tube) and/or body lumens of a patient (e.g., tracheobronchial tree), the stop member 4415 eventually abuts against the expandable diaphragm 4425 and the coupling member 4420 so that further insertion of the suction catheter 4405 is mechanically and/or visually prevented.

FIG. 14B illustrates a more detailed depiction of the stop member 4415. As shown, the stop member 4415 comprises an opening or aperture 4430 that is sized and configured to allow the stop member 4415 to easily slide along the length of the suction catheter 4405 for ease of positioning when not engaged with the diaphragm 4425. In accordance with several embodiments, once the stop member 4415 has been positioned at a desired location along the suction catheter 4405, the suction catheter 4405 can be snapped into protrusions or engagement members 4435 of the stop member 4415 such that suction catheter 4405 no longer slides relative to the stop member 4415. In one embodiment, the protrusions 4435 comprise two or more cylindrical, knobby protrusions. The stop member 4415 may be coupled to the suction catheter 4405 by snap-fit coupling, adhesive coupling, and/or other coupling methods or devices.

FIG. 14C illustrates a side view of an embodiment of a stop member 4415' in which the protrusions 4435 are able to be actively separated by squeezing two wings 4440 of the stop member 4415' together (such as in the usual mechanism for a hair clip). In accordance with several embodiments, once the stop member 4415' has been positioned at a desired position along suction catheter 4405, the wings 4440 are squeezed together, thereby causing the protrusions 4435 to open. The suction catheter 4405 may then be placed between the protrusions 4435 and the wings 4440 may then be released. The suction catheter 4405 is then captured either by the natural recoil of the design or, alternatively, by a spring mechanism, which can be placed between the wings 4440 so that when the wings 4440 are released, the protrusions 4435 actively capture the suction catheter 4405.

In some embodiments, the suction catheter 4405 has markings (e.g., centimeter markings) clearly visible along its length that correspond to markings on standard endotracheal tubes such that when identical centimeter markings are lined up, the distal tip of the suction catheter 4405 is positioned at the distal tip of the endotracheal tube, and not beyond. The alignment of the markings can be used to confirm proper positioning of the suction catheter 4405.

When the closed suction system 4400 is first connected to an endotracheal tube and the first suction procedure is performed, the markings on the suction catheter 4405 can be lined up with corresponding markings on the endotracheal tube to be certain that the distal tip of the suction catheter 4405 does not protrude beyond the distal tip of the endotracheal tube. This alignment may be advantageous in preventing injury to the native airway by the suction catheter 4405. In accordance with several embodiments, the markings constitute a reference so that if a particular clinical circumstance and clinical judgment demand, the suction catheter 4405 could be advanced beyond the distal tip of the endotracheal tube and the specific distance the suction catheter 4405 has been advanced beyond the distal tip of the endotracheal tube can be identified and recorded.

In accordance with several embodiments, the closed suction system 4400 can be used in combination with the manifold 3010 of FIG. 1. The suction catheter 4405 may comprise any of the structural features described herein, such as a cleaning portion. At the time of the first closed suctioning procedure and when the markings (e.g., centimeter markings) of the suction catheter 4405 and the endotracheal tube A are aligned, a marking number may appear visually in the manifold 3010 at the level of the line 3044. The marking number can be noted and recorded as an additional guide to subsequent depth of insertion. Also, at the time of the first closed suctioning procedure and when the markings on the suction catheter 4405 have been aligned with corresponding markings on the endotracheal tube A, the stop member 4415 can be positioned and reversibly attached to the suction catheter 4405 at a position corresponding to the location of the diaphragm 4425 to provide a mechanical and visual stop so as to prevent unintended over-insertion during subsequent suctioning and/or endotracheal tube cleaning procedures. In some embodiments, the distal tip of the suction catheter 4405 and/or the distal tip of the endotracheal tube A have embedded nanotechnology devices that are configured to communicate to a care provider or clinician an audible, tactile, or visual signal to indicate when the distal tip of the suction catheter 4405 has reached the end of the endotracheal tube A.

In accordance with several embodiments, the distal tip of the suction catheter 4405 is atraumatic or blunt so as not to cause injury to the trachea. In some embodiments, the suction catheter 4405 can be introduced in a safe manner such that the suction catheter 4405 does not contact the tracheal wall, carina or other structure outside the endotracheal tube such that the patient is protected from potential discomfort, damage to the trachea, or death due to catheter perforation of the wall of the trachea or other airway or vessel. In some embodiments, suction catheter 4405 is comprised of silicone of a softer durometer than PVC catheters (e.g. between 70 A and 80 A durometer).

FIGS. 15A-15C illustrate an embodiment of a suction catheter 4500 having an integral tube cleaning member 4510 that is configured to be used in an open suction system application or configuration, although it may be inserted through any port of an adapter or swivel connector that is part of a connection between a patient's endotracheal tube and a ventilator. FIGS. 15A-15C illustrate one embodiment of the cleaning member 4510; however, any form or type of cleaning member described herein may be used. The suction catheter 4500 includes a pilot channel 4515 within a lumen of the suction catheter 4500 that is configured to deploy (e.g., expand, inflate) the cleaning member 4510 (e.g., utilizing gas, air, fluid or liquid).

The suction catheter 4500 may include an activation, or deployment, mechanism 4520 (e.g., syringe mechanism) configured to contain a predetermined amount of gas or liquid to deploy the cleaning member 4510 to specified dimensions. For example, the specified dimensions may be dependent on the internal diameter of a tube (e.g., endotracheal tube) into which the suction catheter 4500 is being inserted. The activation, or deployment, mechanism 4520 may include a resilient member 4525 (e.g., spring) which, once the activation mechanism 4520 (e.g., the trigger or plunger of the activation mechanism 4520) is released, actively removes the predetermined amount of gas or liquid from the cleaning member 4510, thereby returning the cleaning member 4510 to its low-profile undeployed position on the suction catheter 4500. In one embodiment, the suction catheter 4500 comprises a wire 4708 (braided or otherwise constructed) that is coextruded with the suction catheter 4500. The wire 4708 (e.g., braided wire) may be configured to allow, facilitate or increase pushability and to minimize or otherwise reduce stretch or snapback when the suction catheter 4500 is removed or withdrawn with the cleaning member 4510 in a deployed, or expanded, configuration. The coextrusion may be particularly advantageous for small diameter, flexible catheters (such as silicone catheters designed for neonate or pediatric patients). If improved pushability is not required or desired, the suction catheter 4500 may be coextruded over another stretch-limiting material, such as suture, string, filament or other material.

The suction catheter 4500 may also comprise a pilot channel 4515 configured to receive air or fluid to cause the cleaning member 4510 to be inflated and expanded against the inside walls of the tube being cleaned. In use, when a predetermined amount of air or fluid is injected through the pilot channel 4515 by the fluid infusion device 4520, the cleaning member 4510 expands to a predetermined size appropriate for cleaning of the specific size tube being treated. The volume of air or fluid to be delivered may be controlled by one or more holes formed along a portion of a reservoir of the activation mechanism 4520. If multiple holes exist, the volume may be altered by covering one or more of the holes so as to provide the correct amount of fluid or air for the inner diameter of the endotracheal tube or other body-inserted tube to be cleaned. In the illustrated embodiment, the suction catheter 4500 comprises one or more depth or distance markings 4535. In other embodiments, a solid wire or mandrel may be coextruded to provide increased pushability and malleability. In other embodiments (not shown), a flexible tube (nylon, Teflon, PEEK, polyamide, etc.) may be used to provide or increase pushability, prevent or reduce stretch or snapback and/or provide an alternate fluid path for delivery of medicaments (e.g., chlorhexidine) or fluids (e.g., saline) distal of the cleaning member 4510. In one embodiment, the activation, or deployment, mechanism 4520 comprises a button-operated mechanism configured to expand (e.g., inflate) and retract (e.g., deflate) the cleaning member. In another embodiment, the activation, or deployment, mechanism 4520 comprises a lever or switch-activated mechanism. The activation, or deployment, mechanism 4520 may be configured to be operated with a single finger of a single hand.

In some embodiments, the suction catheter 4500 includes suction holes 4528 at a distal end of the suction catheter 4500. As shown, the suction holes may include an axial opening at a distal tip of the suction catheter 4500 and/or along one or more sides along the circumference of the suction catheter 4500. The suction catheter 4500 further includes a suction control unit 4530 coupled to a suction catheter 4500. The illustrated suction control unit 4530 comprises a suction control opening with a cap. In one embodiment, the suction control unit 4530 is a button-operated mechanism configured to toggle on and off the suction. In another embodiment, the suction-control unit 4530 comprises a lever or switch-activated mechanism. The suction control unit 4530 may be configured to be operated with a single finger of a single hand.

In some embodiments, at least a portion of the length of the suction catheter 4500 includes distance markings 4535 (e.g., centimeter markings) that match corresponding markings along the endotracheal tube and can be utilized to gauge depth of insertion of the suction catheter 4500 to the distal tip of the endotracheal or other medical tube, or if desired or required, beyond the distal tip. In some embodiments, the suction control unit 4530 and the syringe mechanism 4520 reside on or within a bivalved housing 4540 (exact configuration not shown). In one embodiment, the suction control unit 4530 and the activation mechanism 4520 reside on opposite sides of the proximal controller or housing FIG. 15B illustrates a close-up view of the distal end of the suction catheter 4500. The cleaning member 4510 is shown in a deployed configuration for contact with the inner walls of a tube being cleaned. FIG. 15C illustrates an embodiment of the activation mechanism 4520 in a state corresponding to deployment of the cleaning member 4510 as shown in FIG. 15B. The activation mechanism 4520 in FIG. 15C has been triggered in such a manner that the predetermined volume of gas or liquid has been transferred into the cleaning member 4510 through the pilot channel 4515. The resilient member 4515 is shown in FIG. 15C compressed and ready to return the trigger of the activation mechanism 4520 to a nominal resting position once the trigger has been released.

Figure 16:
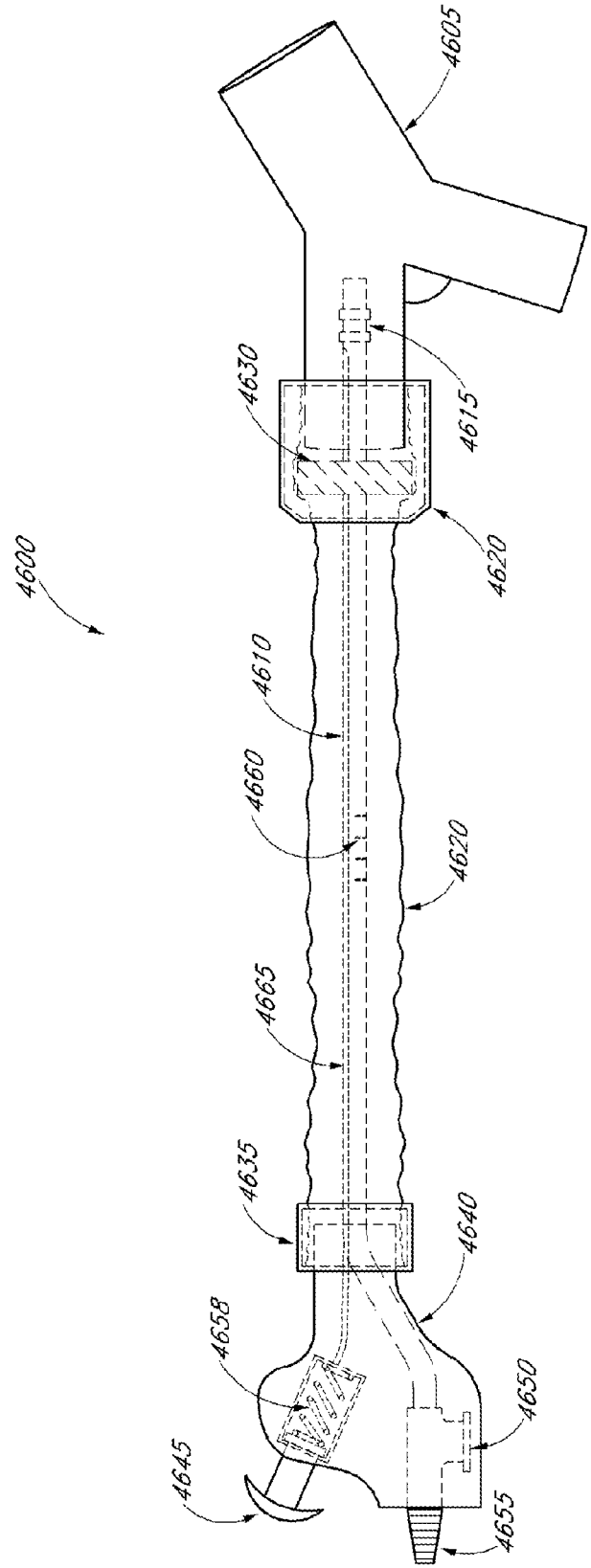
FIG. 16 illustrates a schematic representation of an embodiment of a partially-closed/partially-open suction cleaning system.

FIG. 16 illustrates an embodiment of a suction catheter system 4600 having an integral tube cleaning member that is configured to be used in a "semi-closed" or partially-closed or partially open (e.g., hybrid) configuration. In the illustrated embodiment, a multiport adapter 4605 with a first port configured to connect to a universal adapter of an endotracheal or other medical tube and a second port configured to connect to a ventilator (not shown). The system 4600 includes a suction catheter 4610 with a tube cleaning member 4615 that is enclosed within a flexible protective sheath 4620 and is connected to a third port of the multiport adapter 4605 by a distal connection member 4625.

In one embodiment, the suction catheter system 4600 (e.g., the connection member 4625) includes a flow loss prevention member 4630 (e.g., a washer with a flexible diaphragm) sized to close around the shaft of the suction catheter 4610 such that the suction catheter 4615 can still be moved in and out of an endotracheal or other medical tube connected to the multiport adapter 4605 and/or lungs or patient airways, but prevents loss of ventilated volume back into the sheath 4620. The sheath 4620 may be coupled at its proximal end to a proximal connection member 4635. The proximal connection member 4630 is configured to couple to a bivalved housing 4640. The multiport adapter 4605 may include fewer than three ports or more than three ports (e.g., 2, 4 or 5 ports). In some embodiments, the multiport adapter 4605 comprises an irrigation port 3056 and cap 3058 for cleaning the tip of the suction catheter 4610. In such an embodiment, the suction catheter system 4600 may be left in situ for up to 24 hours.

As shown in FIG. 16, the bivalved housing 4640 may include an activation mechanism (e.g., syringe mechanism) 4645 and a suction controller 4650. The suction controller 4650 may be configured to control suction finger occlusion of a hole or alternatively utilizing a button-operated mechanism. The bivalved housing 4640 includes a wall suction connector 4655 configured to be coupled to a wall suction unit (not shown). The syringe mechanism 4645 may be configured to store a predetermined (e.g., pre-measured) volume of gas or liquid that can be reversibly delivered through a pilot channel 4665 to deploy (e.g., expand, inflate) the cleaning member 4615. A resilient member 4658 (e.g., a spring) within the syringe mechanism 4640 may be configured to return the trigger of the syringe mechanism 4645 to a nominal position, thereby withdrawing the gas or liquid from the cleaning member 4615 and returning the cleaning member 4615 to a collapsed position around suction catheter 4610. As described above, the volume of air or fluid to be delivered may be controlled by one or more holes formed along a portion of a reservoir of the activation (e.g., syringe) mechanism 46450. If multiple holes exist, the volume may be altered by covering one or more of the holes so as to provide the correct amount of fluid or air for the inner diameter of the endotracheal tube or other body-inserted tube to be cleaned. In some embodiments, at least a portion of the length of the suction catheter 4610 includes distance markings 4660 (e.g., centimeter markings) that match corresponding markings along the endotracheal tube and can be utilized to gauge depth of insertion of the suction catheter 4610 to the distal tip of the endotracheal or other medical tube, or if desired or required, beyond the distal tip.

FIG. 17 illustrates a proximal portion and a distal portion of an embodiment of a body-inserted tube cleaning system 4700 for providing cleaning in an environment where patients may be mechanically ventilated with a body-inserted tube (e.g., endotracheal tube). The cleaning system 4700 may comprise a protected endotracheal tube cleaning device adapted for primary cleaning or complementary body-inserted tube cleaning when suctioning is being performed for routine maintenance of the endotracheal tube. The cleaning system 4700 comprises a catheter 4705 and optionally comprises a protective sheath 4710, a biofilm collection adapter or manifold 4715 and a fluid infusion device 4720. The catheter 4705 comprises a molded proximal end 4706 that is configured to connect to or couple with the fluid infusion device 4720. The catheter 4705 comprises a distal cleaning member 4707 such as the cleaning members described herein. For example, the distal cleaning member 4707 may comprise a silicone balloon wiper with two integrated rings each having at least one squared edge. In some embodiments, the balloon wiper does not comprise rings and may be smooth.

In some embodiments, the catheter 4705 comprises a Foley-type catheter or a percutaneous transluminal coronary angioplasty (PTCA)-type catheter. In one embodiment, the catheter 4705 comprises a wire 4708 (braided or otherwise constructed) that is coextruded with the catheter 4705. The wire 4708 (e.g., braided wire) may be configured to allow, facilitate or increase pushability and to minimize or otherwise reduce stretch or snapback when the catheter 4705 is removed with the cleaning member 4707 in a deployed, or expanded, configuration. If improved pushability is not required or desired, the catheter 4705 may be coextruded over another stretch-limiting material, such as suture, string, filament or other material.

The catheter 4705 may also comprise a pilot channel 4709 configured to receive air or fluid (e.g., gas or liquid) to cause the distal cleaning member 4707 to be inflated and expanded against the inside walls of the tube being cleaned. In use, when a predetermined amount of air or fluid is injected through the pilot channel 4709 by the fluid infusion device 4720, the cleaning member 4707 expands to a predetermined size appropriate for cleaning of the specific size tube being treated. In the illustrated embodiment, the catheter 4705 comprises one or more depth or distance markings 4711. For clarity, the fluid configured to be delivered by the fluid infusion device 4720 can be any gas or liquid.

In other embodiments, a solid wire or mandrel may be coextruded to provide increased pushability and malleability. In other embodiments, a flexible tube (nylon, Teflon, PEEK, polyamide, etc.) may be used to provide or increase pushability, prevent or reduce stretch or snapback and provide an alternate fluid path for delivery of medicaments (e.g., chlorhexidine) or fluids (e.g., saline) distally of the cleaning member 4707. In some embodiments, the catheter 4705 is less than 2 mm in diameter. In such embodiments, a semi-rigid tube (nylon, PEEK, Teflon, polyamide, PVC, etc.) is used as a sleeve between the cleaning member 4707 and fluid infusion device 4720 to provide or increase pushability.

The protective sheath 4710 may comprise a collapsible, flexible sheath and extends from the molded proximal end 4706 of the catheter 4705 to the distal biofilm collection adapter or manifold 4715. The distal biofilm collection adapter comprises a flexible diaphragm 4716 which, on withdrawal of the catheter 4705, scrapes off accumulated secretions that then remain in the distal biofilm collection adapter 4715 for disposal. In one embodiment, the fluid infusion device 4720 comprises a Luer lock syringe. In some embodiments, the fluid infusion device 4720 comprises one or more holes in a barrel or other reservoir of the device that is configured to control the volume of air or fluid delivered, thereby allowing the fluid infusion device 4720 (e.g., syringe) and the catheter 4705 to be prefilled with an appropriate volume for the endotracheal tube or other body-inserted tube to be cleaned, and prevents against or reduces the likelihood of inadvertent over or under inflation of the cleaning member 4707 by an operator. If multiple holes exist, the volume may be altered by covering one or more of the holes so as to provide the correct amount of fluid or air for the inner diameter of the endotracheal tube or other body-inserted tube to be cleaned, thereby facilitating adaptability of a single suction catheter system for multiple different sized tubes.

The cleaning system 4700 can be provided and used without the protective sheath 4710 and the biofilm collection adapter 4715, in which case the catheter 4705 may be inserted directly into the endotracheal tube with no adapter, or potentially with other adapters that allow insertion of the catheter 4705 into the endotracheal tube while still ventilating the patient.

Portions of, or the entire length of, the catheter 4705 (e.g., the cleaning member 4707) may comprise a lubricious coating configured to improve ease of insertion and withdrawal when the cleaning member 4707 is deployed and/or an antimicrobial coating. In some embodiments, the cleaning member 4707 is used to apply an antimicrobial coating to the inside of a body-inserted tube (e.g., endotracheal tube) such as by dipping the catheter tip in an antimicrobial solution or gel prior to passage into and subsequent extraction from the body-inserted tube. In some embodiments, the cleaning member 4707 is modified to include a sponge-like consistency material on the outside of the cleaning member 4707 that is configured to be soaked in antimicrobial compounds. Expansion of the cleaning member 4707 may cause release of the antimicrobial compounds along the inside of the body-inserted tube as the catheter 4705 is being withdrawn from the body-inserted tube to wipe or clean the body-inserted tube.

Figure 18A:
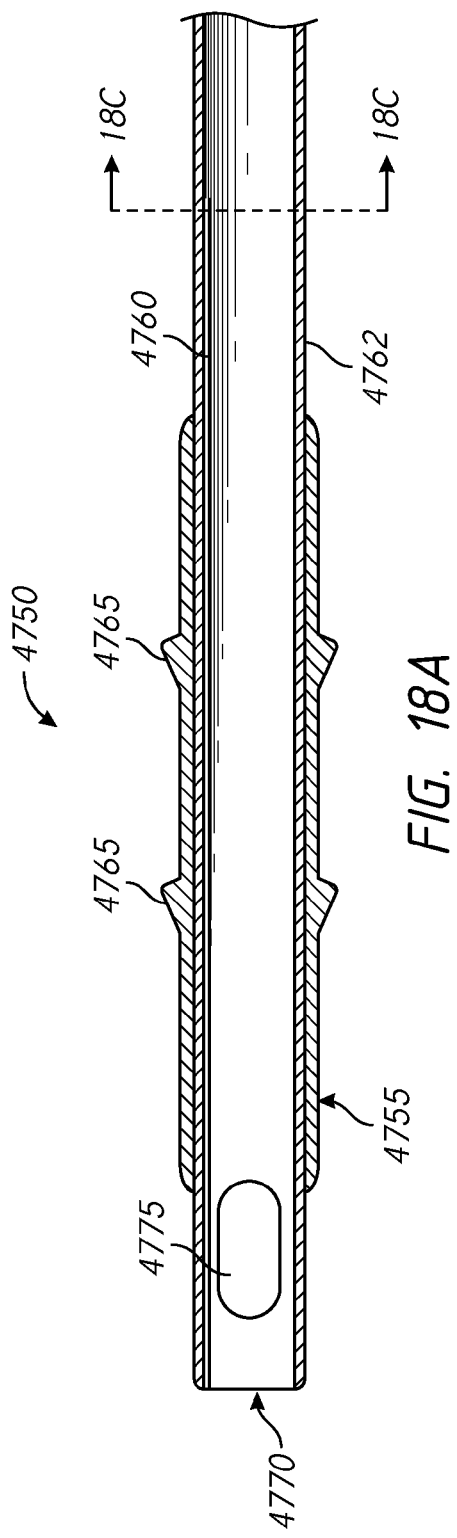
FIGS. 18A-18C illustrate an embodiment of a suction catheter with an integrated endotracheal tube cleaning member for use in a closed suction system
Figure 18C:
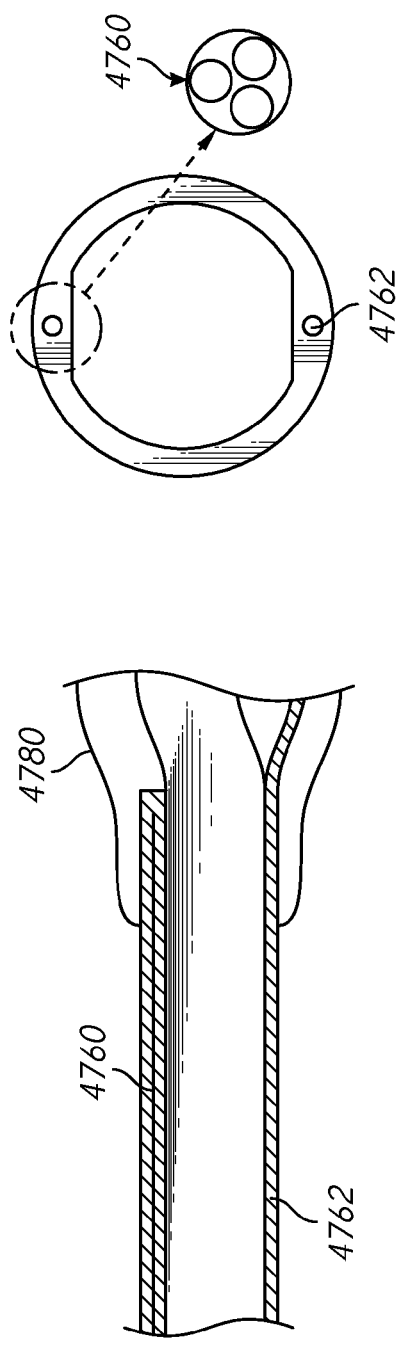
Figure 18B:

FIGS. 18A-18C illustrate an embodiment of a suction catheter 4750 having an integrated body-inserted tube cleaning member 4755 configured for use in a closed suction system. FIG. 18A illustrates a distal portion of the suction catheter and FIG. 18B illustrates a proximal portion of the suction catheter 4750. FIG. 18C illustrates a cross-sectional view of a section (taken along line 18C-18C) of the suction catheter 4750 proximal to the cleaning member 4755.

In some embodiments, the suction catheter 4750 comprises an extruded silicone catheter; however, other materials may be used as desired and/or required. The suction catheter 4750 comprises a wire 4760 that is co-extruded with at least a portion of the length of the shaft of the catheter and is adherent to the shaft along its length. In one embodiment, the wire 4760 is braided. As shown in the illustrated embodiment, the wire 4760 does not extend all the way to the distal tip of the catheter 4750 in order to prevent possible injury that might be caused by the wire 4760 should it protrude from the distal tip of the catheter 4750 during use. In some embodiments, the wire 4760 provides, facilitates or increases pushability to the catheter 4750 as it is inserted and prevents or otherwise reduces stretching or snapback when the catheter 4750 is removed from a body-inserted tube (e.g., endotracheal tube) with the cleaning member 4755 expanded. FIG. 18C illustrates an embodiment of the wire 4760. In other embodiments, a solid wire or mandrel may be coextruded to provide increased pushability and malleability. In some embodiments, a flexible tube (nylon, Teflon, PEEK, polyamide, etc.) may be used to provide or increase pushability, prevent or reduce stretch or snapback and provide an alternate fluid path for delivery of medicaments (chlorhexidine) or fluids (saline) distally of the cleaning member 4755. In one embodiment, the suction catheter 4750 is not coextruded with wire or another material.

The suction catheter 4750 may comprise a pilot channel 4762 through which air or fluid can be introduced to inflate or expand the cleaning member 4755. In the illustrated embodiment, the cleaning member 4755 comprises a silicone balloon with rings 4765 and is located at the distal end portion of the suction catheter 4750. The rings may be integrated with the balloon or non-integrated. In some embodiments, the balloon does not comprise rings and may be smooth. The balloon of the cleaning member 4755 may be bonded or otherwise affixed to the shaft of the suction catheter 4750 at its proximal and distal ends, thereby allowing a central portion to inflate. In one embodiment, the cleaning rings 4765 of the cleaning member 4755 have at least one squared edge that is integrated into the balloon. In an expanded or inflated state, the cleaning or shaving rings 4765 may be configured to engage an interior surface (e.g., wall) of a body-inserted tube (e.g., endotracheal tube) and clean the body-inserted tube as the suction catheter 4750 is withdrawn. In some embodiments, the suction catheter 4750 comprises a Foley-type catheter or a percutaneous transluminal coronary angioplasty (PTCA)-type catheter. The suction catheter 4750 may comprise a distal axial opening or port 4770 and two side holes, openings or ports 4775 (as shown in FIG. 18A). FIG. 18B illustrates a molded silicone connector 4780 that is configured to couple the suction lumen (e.g., main central lumen) and pilot channel lumen to a proximal controller (not shown) as disclosed elsewhere herein.

In accordance with several embodiments, using the same material(s) (e.g., silicone) with varying degrees of hardness for the catheter shaft, cleaning member 4755, and connector 4780 provides one or more benefits. First, using all silicone components may allow for robust bonding and may help protect against dislodgment of the cleaning member 4755 during use. Second, the memory features of silicone or other materials with elastic properties can allow the cleaning member 4755 to passively return to a low-profile state on the catheter 4750 when not actively deployed, or inflated. In some embodiments, the catheter shaft is silicone having a durometer of 80 A, the cleaning member 4755 is 60 A-65 A durometer silicone and the connector 4780 is 70 A-80 A durometer silicone.

The catheter shaft, cleaning member 4755, or both may comprise a lubricious coating configured to improve ease of insertion and withdrawal when the cleaning member 4755 is deployed (e.g., inflated). An antimicrobial coating may also be used to decrease colonization of the catheter shaft and cleaning member 4755 (for example, when used for several days in a closed system). The cleaning member 4755 may be used to apply an antimicrobial coating to the inside of a body-inserted tube (e.g., endotracheal tube), such as by dipping the distal catheter tip in an antimicrobial solution or gel prior to passage into and subsequent extraction from the body-inserted tube. In some embodiments, the cleaning member 4755 is modified to include a sponge-like consistency material on the outside of the balloon that could be soaked in antimicrobial compounds. Expansion (e.g., inflation) of the cleaning member 4755 may cause release of the antimicrobial compounds along the inside of the body-inserted tube as the suction catheter 4750 is being withdrawn from the body-inserted tube to wipe or clean the body-inserted tube. In some embodiments, the lubricious coating is Parylene, Duraglide™ or NuSil MED 10-6670 or other biocompatible coatings that reduce the coefficient of friction. These coatings may also include anti-microbial compounds (e.g., chlorhexidine).

The suction catheter 4750 may be used in a closed suction system comprised of a manifold that provides for connection of the body-inserted tube (e.g., endotracheal tube), a ventilator, and the suction catheter 4750; a protective flexible sheath that extends from the manifold to a proximal controller of the suction catheter 4750; and the proximal controller that allows for independent suctioning and cleaning of body-inserted tubes by expansion of the cleaning member 4755. The suction catheter 4750 may also be used without the manifold and protective sheath by practitioners preferring open suction systems. In open suction system environments, the suction catheter 4750 may be used in conjunction with a biofilm collection adapter (e.g., the biofilm collection adapters or systems illustrated in and described in WIPO Publication Number WO 2013/063520, which is hereby incorporated herein by reference). The suction catheter 4750 may also be used in a "semi-closed" fashion where it could be provided as the above-described catheter, a proximal controller, a protective sheath, and a biofilm collection adapter in a single, integrated unit. In some embodiments, the balloon is replaced by a mechanically-expandable balloon and/or comprises any of the structural features of the expandable cleaning members (e.g., mechanically-expandable or inflatable) described herein or in WIPO Publication Number WO 2013/063520 or in U.S. Publication No. 2011/0023885, the contents of each of which are hereby incorporated herein by reference, such as a mechanically-actuated scaffold (e.g., a mesh scaffold actuated by movement of two concentric tubes attached to opposite ends of the mesh scaffold with respect to each other).

Figure 19:
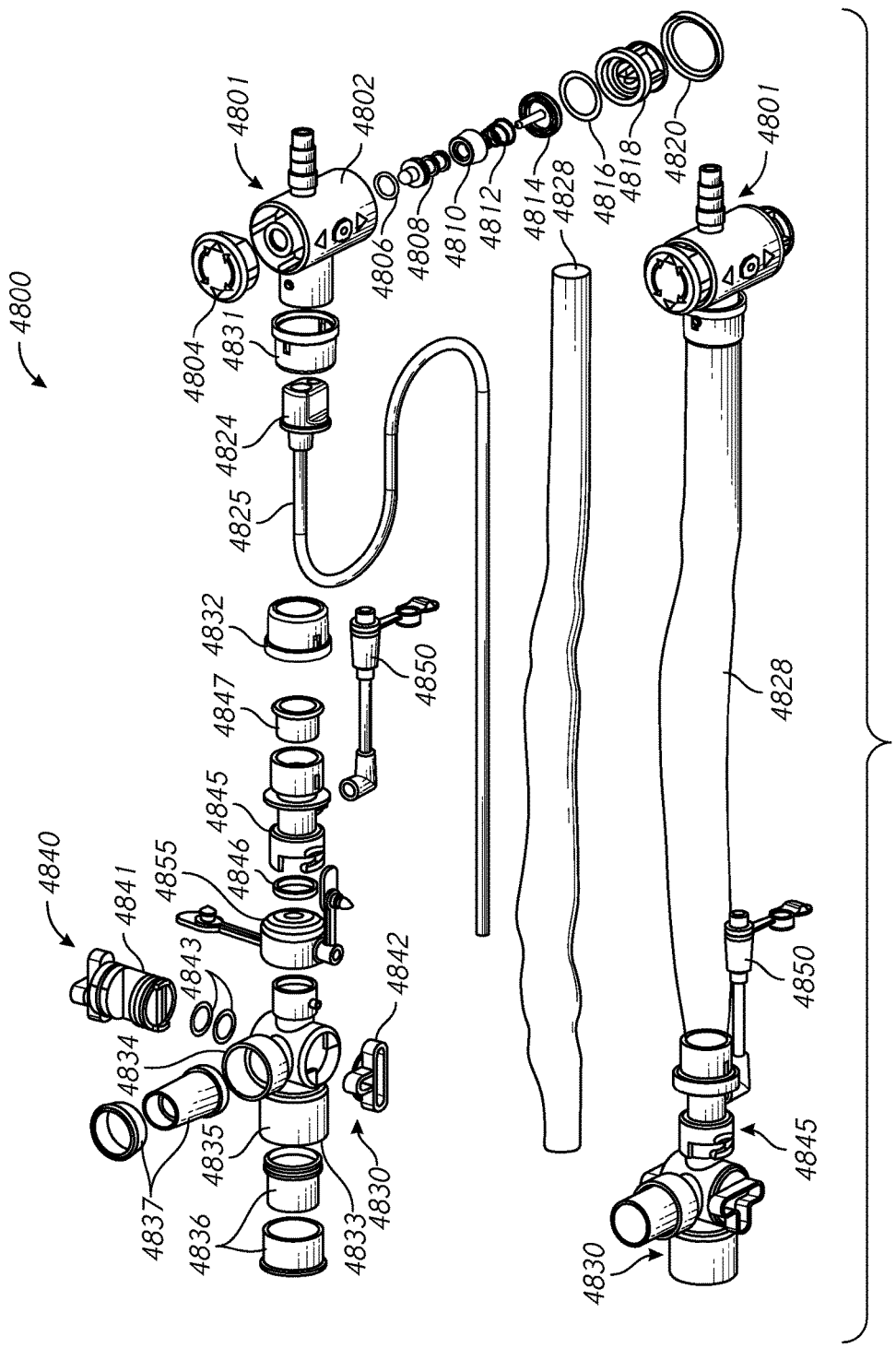
FIG. 19 is an exploded assembly view of an embodiment of a closed suction system including an integrated endotracheal tube cleaner.

FIG. 19 is an exploded view and a perspective assembled view of an embodiment of a closed suction system 4800 including a suction catheter having an integrated body-inserted tube cleaner. In the illustrated embodiment, the closed suction system comprises a proximal controller 4801 comprising a proximal control valve housing 4802 and a suction control valve cap 4804 having markings indicating that the suction control valve cap 4804 rotates and arrows indicating direction of airflow. The proximal controller 4801 may comprise an inlet port to be coupled to suction tubing. In one embodiment, rotation of the suction control valve cap 4804 ninety degrees makes the arrows perpendicular to the direction of airflow, showing closure, and locks the suction control valve cap 4804 so that it is unable to be depressed. The proximal controller 4801 of the illustrated embodiment comprises a first O-ring 4806, a pillar housing 4808, a pillar rubber gasket 4810, a pillar spring 4812, and a suction cap 4814 that, together with the control valve housing and the suction control valve cap 4804 perform the suction functions of the closed suction system 4800. The proximal controller 4801 comprises a second O-ring 4816, a syringe-like inflation valve 4818, and an inflation valve cap 4820 configured to perform the inflation functions of the closed suction system 4800. Like the suction control valve cap 4804, the inflation valve cap 4820 comprises arrows indicating appropriate rotation and positioning for function, and when the arrows are rotated ninety degrees to be perpendicular to the axis of the suction catheter, the inflation valve cap 4820 will not function. The amount of air to be displaced into the distal cleaning member of the suction catheter for the particular size endotracheal tube or other body-inserted tube may be controlled by placement of one or more holes in the proximal controller housing 4802. Differing closed suction devices may be labeled for the appropriate size body-inserted tube on which it is to be used, with the hole(s) placed appropriately for that particular device at manufacture. In some embodiments, multiple holes are placed along the length of the proximal controller housing 5229 or a reservoir of the inflation or expansion mechanism corresponding to different sizes (e.g., internal diameters) of tubes. A single cleaning device may be adapted for use of different sized tubes by covering one or more of the holes so as to control the amount of volume of air or fluid that can be stored. In addition, the hole(s) may facilitate venting to atmosphere through the pilot channel so as to accommodate leaks to the external environment by allowing the fluid (gas or liquid) inflation mechanism to recharge.

In some embodiments, a molded proximal portion 4824 of a suction catheter 4825 is configured to couple to or mate with a port of the proximal controller 4801. The suction catheter 4825 may comprise an integrated tube cleaning member, such as described in connection with FIG. 18. The suction catheter 4825 and its integrated tube cleaning member may comprise any of the structural features of the suction catheters or suction catheter systems described herein. In some embodiments, the suction catheter 4825 may comprise a mechanically-actuated cleaning member instead of an inflatable cleaning member, such as the mechanically-actuated cleaning members described in WIPO Publication No. 2014/089028 and in U.S. Publication No. 2011/0023885, the contents of each of which are hereby incorporated herein by reference. In such embodiments, the inflation valve cap 4824 may be replaced with a mechanical actuation control assembly. In one such embodiment, a mesh scaffold may be actuated by movement of two concentric tubes attached to opposite ends of the mesh scaffold with respect to each other). The term "scaffold" as used herein shall be given its ordinary meaning and shall include, without limitation, support members, collapsible members, expandable members, distensible members, solid structures, mesh structures, braided devices, porous structures, struts, polymeric structures, membranes, mechanically actuated bellows, bladders, stents, umbrella-type devices, ribs, spokes, frames, and the like, and combinations thereof. Scaffolds may be fully or partially covered or may be uncovered. Covered scaffolds may comprise skeletons that are partially or fully covered by membranes, fabrics, films, multiple layers, and/or coated. Scaffolds may function as the cleaning member and/or may be used for supporting a cleaning member. Scaffolds can be mechanically actuated, self-actuated, inflated, and/or combinations thereof.

The closed suction system 4800 further comprises a protective, flexible and collapsible sheath 4828 that encloses the catheter 4825 and protects the catheter 4825 against contamination. The sheath 4828 extends from a manifold 4830 to the proximal controller 4801. The sheath 4828 is coupled to the manifold 4830 via a first coupling member 4832 and coupled to the proximal controller 4801 via a second coupling member 4831.

In one embodiment, the manifold 4830 comprises a manifold housing or main body 4835. The manifold 4830 may also comprise a first swivel connector 4836 configured to couple to a distal port 4833 of the manifold housing 4835 and to a body-inserted tube, e.g., endotracheal tube (not shown). The components of the first swivel connector 4836 may be constructed or designed so that there is a smooth transition and no edge or step-off inside the first swivel connector 4836 that could catch on the tube cleaning member of the suction catheter 4825 as it is withdrawn into the body 4835 of the manifold 4830. The lack of an edge or step-off also may advantageously prevent collection of biofilm (e.g., debris or secretions) within the first swivel connector 4836. In one embodiment, no portion of the interior dimension of the first swivel connector 4836 is smaller than the internal diameter of the body-inserted tube. The manifold 4830 may further comprise a second swivel connector 4837 configured to couple to a side port 4834 of the manifold housing 4835 and to a ventilator (not shown). The first swivel connector 4836 and the second swivel connector 4837 may be configured to couple to the manifold housing 4835 via friction fit coupling, interference fit coupling, threaded coupling, or other coupling mechanisms.

In one embodiment, the manifold 4830 comprises a stopcock assembly 4840 comprising a control valve 4841 which may be controlled (e.g., turned or rotated) so that the closed suction system, ventilator, and body-inserted tube into the patient are all in continuity. The control valve 4841 may include directional arrows or other indicators to indicate how it may be closed to isolate the closed suction system from the ventilator circuit while maintaining the connection from the ventilator to the body-inserted tube (e.g., endotracheal tube) and the patient. The stopcock assembly 4840 may include a cap 4842 configured to interface or mate with an end of the control valve 4841 through the main housing 4835 of the manifold 4830 and one or more O-rings 4843 to facilitate sealing.

In some embodiments, the closed suction system 4800 comprises a separable module 4800. The manifold 4830 may be removably coupled to the rest of the closed suction system 4800 (e.g., the sheath 4828, the suction catheter 4825 and the proximal controller 4801) via a modular connector 4845. The modular connector 4845 may comprise a gasket 4846 and a secretion removing member 4847 comprising a diaphragm configured to wipe secretions from the catheter 4825 as it is withdrawn out of the patient. A proximal end of the modular connector 4845 may be configured to be inserted within the second coupling member 4832.

The closed suction system 4800 may optionally comprise an irrigation unit 4850 that is configured to attach or is attached to the modular connector 4845. The irrigation unit 4850 may be used to irrigate and clean the suction catheter 4825 (e.g., the cleaning member of the suction catheter 4825) once it has been withdrawn from the patient and isolated from the ventilator circuit by closing the stopcock assembly 4840. The closed suction system 4800 may optionally comprise a cap 4855 that is configured to couple to a proximal inlet port of the manifold 4830 or directly to the body-inserted tube (or a universal connector of the body-inserted tube) upon removal of the modular connector 4845 from the manifold 4830 or upon removal of the manifold 4830 from the body-inserted tube. The cap 4855 may be configured to allow for instrumentation of the patient's airway. An embodiment of the cap 4855 is further described in connection with FIG. 20.

In accordance with several embodiments, the closed suction system 4800 is connected to a body-inserted tube (e.g., endotracheal tube) and a ventilator via the manifold 4830. In some embodiments, the patient is hyper oxygenated for several minutes. The control valve 4841 of the stopcock assembly 4840 may be turned to open the ventilator and patient to the closed suction system 4800 and the catheter 4825 may be inserted into the body-inserted tube until depth marks on the catheter 4825 line up with depth marks on the body-inserted tube that is being treated. At the time of this first cleaning, a movable depth stop on the catheter 4825 may be moved and juxtaposed to the second coupling member 4832 connected to the manifold 4830, thereby allowing for both visual and mechanical guidance for depth of insertion at subsequent cleanings. In some embodiments, the proximal controller 4801 is hooked to suction tubing and the strength of suction is set according to the American Association of Respiratory Care (AARC) guidelines.

After connection of the proximal controller 4801 to the suction tubing via a suction inlet of the proximal controller 4801, the suction control valve cap 4804 may be rotated (e.g., ninety degrees) from its locked position to a position where arrows or other indicators show alignment of the control valve 4802 with a longitudinal axis of the catheter 4825. The suction control valve cap 4804 can then be depressed, thereby applying suction to the catheter 4825 and the catheter 4825 is withdrawn from the body-inserted tube back into the closed suction system 4800. Upon removal of the catheter 4825 from the body-inserted tube and into the manifold 4830, the stopcock assembly 4840 may be closed and the suction catheter 4825 is cleaned by irrigating saline or other fluid into the manifold 4830 through the irrigation unit 4850 while simultaneously applying suction to the catheter tip, thereby cleaning both the suction catheter tip and the cleaning member.

Further cleaning may be performed by reopening the stopcock assembly 4840 and inserting the suction catheter 4825 again into the body-inserted tube either by aligning depth marks on the catheter 4825 with corresponding depth marks on the body-inserted tube, or by using the visual and mechanical stop that was placed previously to guide depth of insertion. The inflation valve cap 4820 may then be manipulated (e.g., turned ninety degrees) to align the arrows or other indicators with the longitudinal axis of the catheter 4825. The inflation valve cap 4820 may then be depressed to deploy (e.g., expand, inflate) the cleaning member to a predetermined size chosen for the body-inserted tube being cleaned. In one embodiment, the suction catheter 4825 is then slowly withdrawn (e.g., over a duration of 3-5 seconds) back into the manifold 4830 and the stopcock assembly 4840 is once again closed. The catheter tip and cleaning member may then again be cleansed utilizing the irrigation unit 4850 by injecting saline while simultaneously utilizing the suction to empty the debris and residual saline. The amount of air or fluid displaced into the cleaning member may be predetermined for differing size tubes by utilization of holes placed at specific sites in the cylinder in which the air to be displaced is stored. In some embodiments, multiple holes are placed along the length of the cylinder or a reservoir of the inflation or expansion mechanism corresponding to different sizes (e.g., internal diameters) of tubes. A single device may be adapted for use of different sized tubes by covering one or more of the holes so as to control the amount of volume of air or fluid that can be stored. In addition, the hole(s) may facilitate venting to atmosphere through the pilot channel so as to prevent leaks.

Figure 20:
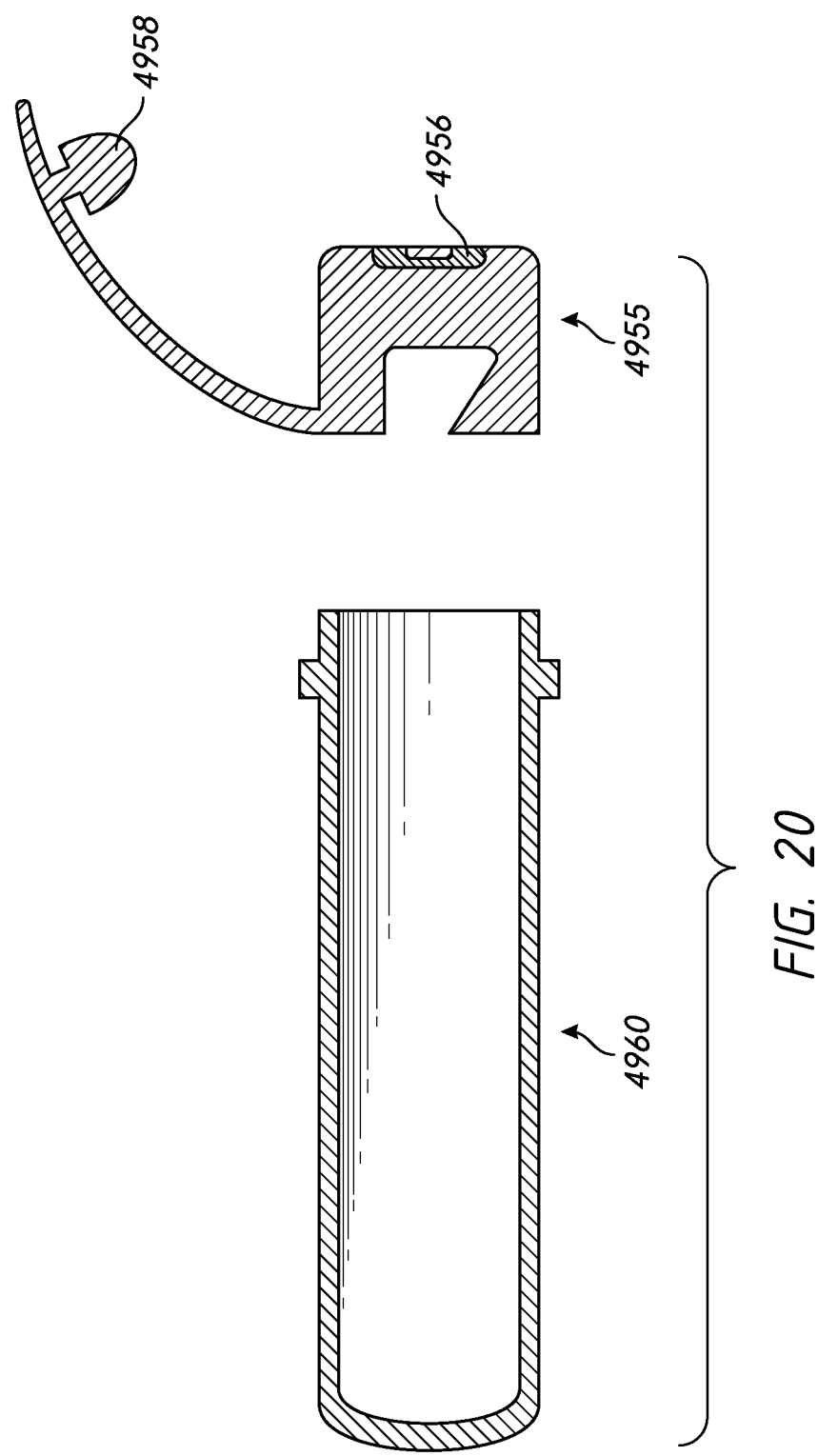
FIG. 20 illustrates embodiments of a modular access connector and a cleaning garage configured for use with a closed suction system.

FIG. 20 illustrates embodiments of an accessory cap 4955 (e.g., cap 4855) that is configured to be placed onto the manifold 4830 when the closed suction system/module 4800 (e.g., sheath 4828, catheter 4825, and controller 4801) is removed. The cap 4955 comprises a flexible diaphragm 4956 and a plug 4958. When the plug 4958 is inserted into the diaphragm 4856, the stopcock assembly 4840 in the manifold 4830 may be in the open position without loss of air from the ventilatory circuit. When the plug 4958 is removed, instruments such as suction catheters, BAL catheters, or bronchoscopes may be inserted through the flexible diaphragm 4956 and into the body-inserted tube and, if appropriate, the distal respiratory tree. FIG. 20 also illustrates an embodiment of an accessory cap or garage 4960 configured to be temporarily connected to a distal end of the removed closed suction module to keep the suction tip and cleaning member protected from the outside environment while the closed suction module is disconnected from the manifold 4830. Additionally, placing the cap 4960 over the closed suction module as it is removed from the manifold 4830 may allow additional cleaning of the catheter tip and cleaning member to be performed by use of injected saline and suction away from the patient's bedside, thereby facilitating manual agitation of the cleaning chamber to improve cleaning, and also allowing for the potential injection of antimicrobial compounds into the cleaning chamber to sterilize or decrease colony counts of microbes brought back into the cleaning chamber by the acts of suctioning or tube cleaning. Once instrumentation through the cap 4955 has been completed, caps 4955 and 4960 can be removed and discarded and the closed suction module 4800 can be reconnected to the manifold 4830.

Figure 21:
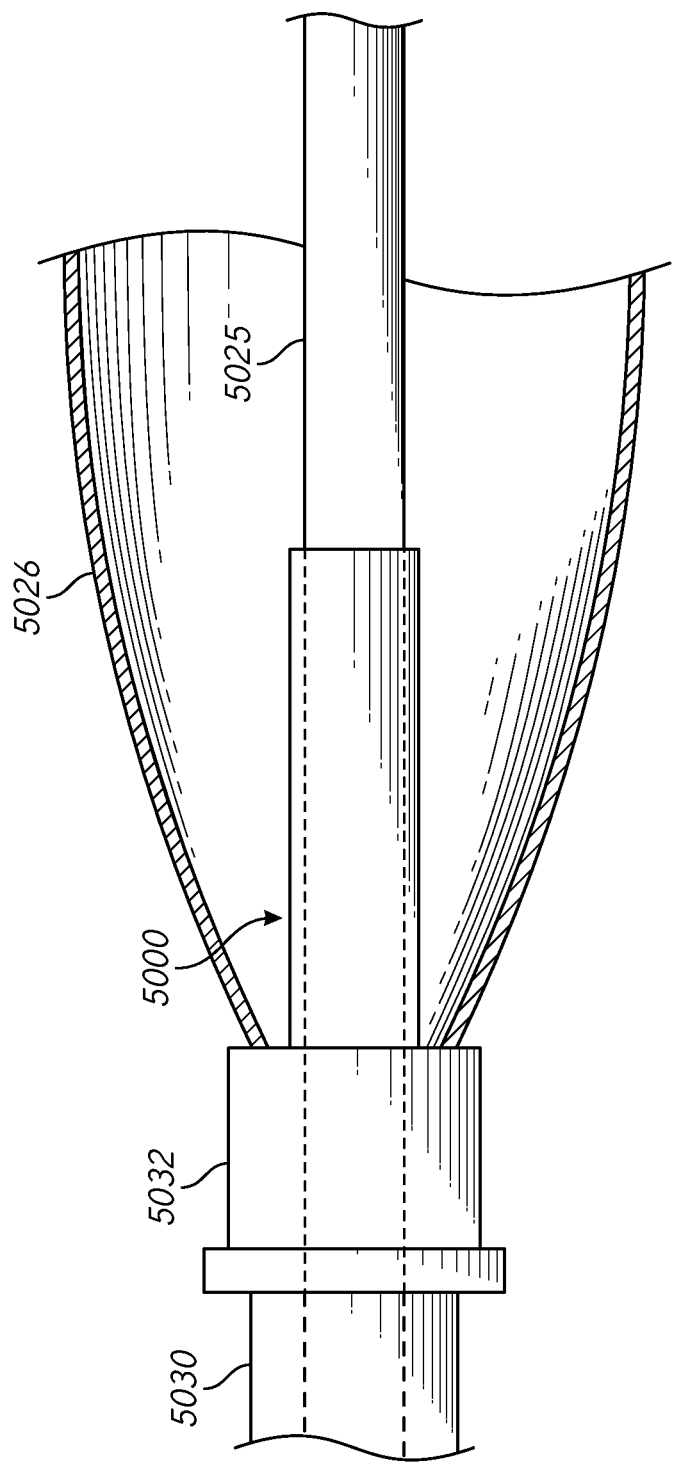
FIG. 21 illustrates an embodiment of a cap extension configured for use with a closed suction system.

FIG. 21 illustrates an embodiment of a cap extension member 5000 configured for use with a closed suction system (e.g., closed suction system/module 4800). The cap extension member 5000 may be formed integral with or removably coupled to a cap 5032 (e.g., second coupling member 4832) that confines a flexible sheath 5026 (e.g., sheath 4828) surrounding a suction catheter 5025 (e.g., catheter 4825) at the point of the sheath's connection to a ventilating manifold 5030 (e.g., manifold 4830). The cap extension member 5000 may be injection molded as part of the manifold 5030 or molded separately. The cap extension member 5000 may be formed with a receptacle for mechanically attaching to the cap 5032. The cap extension member 5000 may be extruded of a material suitable for plastic bonding (e.g., PVC) and may be bonded to the cap 5032 using solvent (e.g., cyclohexanone) or adhesive (e.g., cyanoacrylate). The cap extension member 5000 comprises a shaft having a length configured to extend into the flexible sheath 5026. The cap extension member 5000 may be composed of a lightweight and transparent material. For example, the cap extension member 5000 may be composed of nylon, PEEK, Teflon, polyamide, PVC, etc. In accordance with several embodiments, the cap extension member 5000 advantageously allows an operator to "pull" the suction catheter 5025 into the manifold 5030 and body-inserted tube by sliding the sheath 5028 proximally over the shaft of the extension member 5000 rather than requiring "pushing" of the catheter 5025 through the cap 5032.

In accordance with several embodiments, the catheter 5025 may be of such a small diameter as to limit its column strength to such a point that it is impossible to push as the catheter 5025 will simply fold over on itself. Utilizing cap extension member 5000, it is possible to pull the catheter 5025 rather than push it. As the flexible sheath 5026 is pulled on the cap extension member 5000 and collected, the flexible sheath 5026 creates a pulling force that allows the catheter 5025 to advance without folding over on itself. Further, the cap extension member 5000 allows the flexible sheath 5026 to be moved out of the way of the catheter 5025 such that it prevents the bunching up of the flexible sheath 5026 from interfering with the advancement of the catheter 5025.

In accordance with several embodiments, the cap extension member 5000 may advantageously allow suction catheters that are soft, pliable, or extremely flexible and have limited pushability to be employed, as well as suction catheters having smaller diameters (e.g., between 1 mm and 5 mm). For example, the cap extension member 5000 may facilitate introduction of soft, pliable catheters having integrated expandable cleaning members that are designed for cleaning of body-inserted tubes sized for neonates or pediatric patients. The cap extension member 5000 may also be incorporated in systems without the accessory cap 4955, 4855. For example, a tubular extension member operating in the same manner as the cap extension member 5000 described herein may be used in connection with any manifold or adapter (or port of a manifold or adapter) for the insertion of soft, pliable catheters or instruments and/or or instruments with diameters less than 5 mm in outer diameter.

Figure 22:
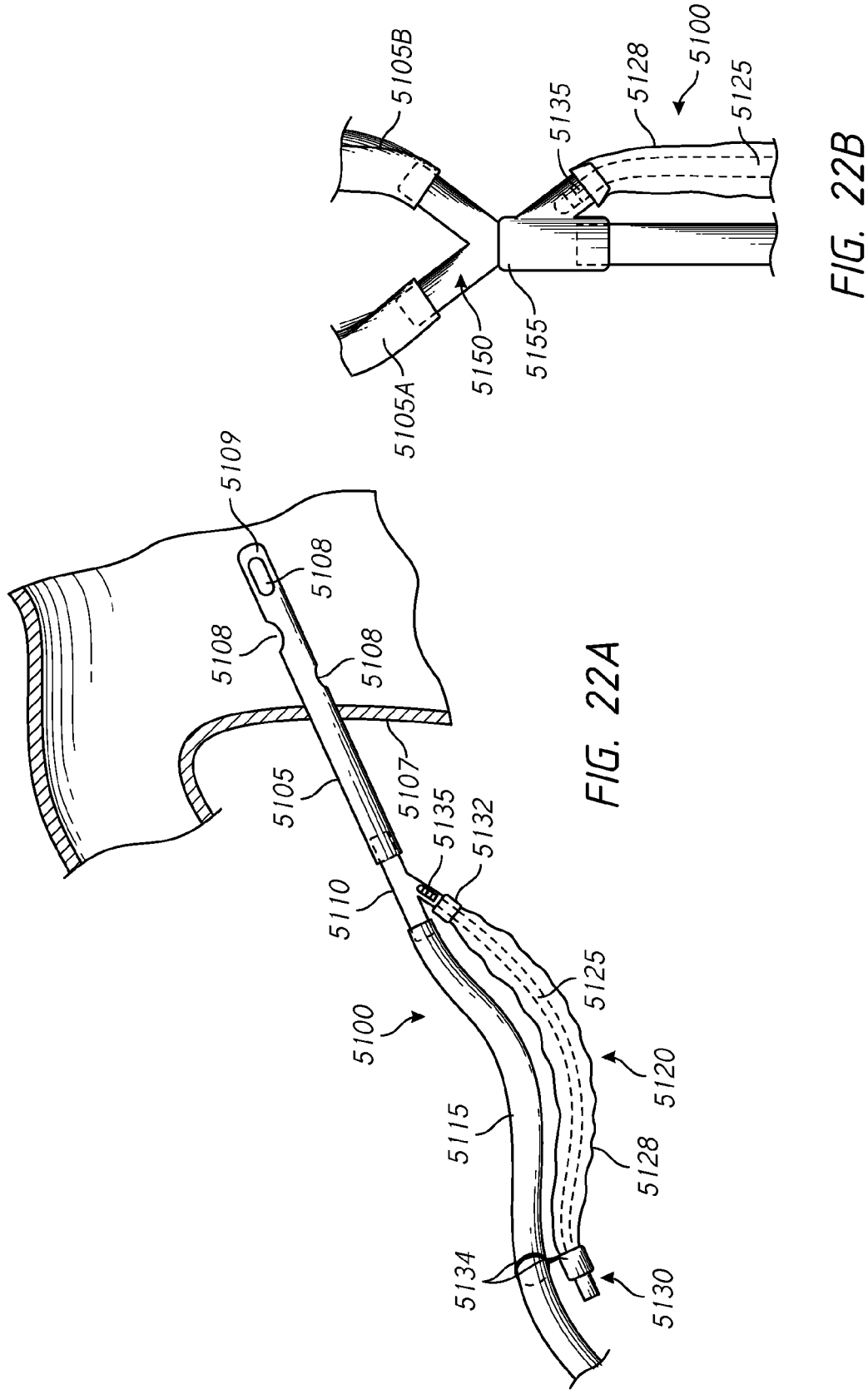
FIGS. 22A and 22B illustrate an embodiment of a closed chest tube cleaning system.

FIGS. 22A and 22B illustrate an embodiment of a closed chest tube cleaning system 5100. In some embodiments, the closed chest tube cleaning system 5100 may be reusable. FIG. 22A illustrates a chest tube 5105 inserted through a chest wall 5107. The distal end of the chest tube 5105 may be inserted into the pleural space around the lung. The chest tube 5105 may have multiple side holes 5108 but a closed distal end 5109 to prevent insertion of a cleaning catheter beyond the distal end 5109 of the chest tube 5105. The chest tube cleaning system 5100 may further comprise an adapter 5110 (e.g., Y connector) configured to connect to the chest tube 5105 (via a distal port) and to a flexible drainage tubing 5115 and to a closed cleaning catheter module 5120 (e.g., via two proximal ports). In one embodiment, the distal port of the adapter 5110 and the proximal port to which the flexible drainage tubing 5115 are connected are arranged such that the chest tube 5105 is connected to the flexible drainage tubing 5115 in a straight-line fashion.

The closed cleaning catheter module 5120 may comprise a catheter 5125, a protective sheath 5128, a proximal controller 5130, and two coupling or connection members 5132, 5134. The catheter 5125 may comprise an expandable cleaning member 5135, such as any of the cleaning members described herein (e.g., inflatable balloon with one or more integrated shaving rings, a plain generally smooth balloon without shaving rings, a mechanically-actuated cleaning member, or any of the cleaning members described herein). In one embodiment, the catheter 5125 comprises a silicone catheter coextruded over a thin braided wire to allow pushability and reduce (e.g., minimize) stretch of the catheter 5125 on withdrawal with the cleaning member 5135 in an expanded configuration, such as described in connection with FIGS. 17 and 18. In embodiments in which the cleaning member is inflatable, the catheter 5125 may comprise a pilot channel to inject air or fluid into the cleaning member 5135. The protective sheath 5128 may comprise a flexible and transparent sheath configured to enclose the catheter 5125 and prevent against contamination. The sheath 5128 may be connected to a proximal port (e.g., a side or branch port) of the adapter 5110 via the connection member 5132. In one embodiment, the connection member 5132 comprises a cap with a flexible diaphragm inside configured to scrape off secretions, blood, etc. from the catheter 5125 as it is withdrawn back into the sheath 5128. The connection member 5132 may anchor the proximal end of the sheath 5128. The catheter 5125 may comprise one or more depth markers (e.g., a series of numbered depth markers) that correspond to similar markers on the chest tube 5105.

In one embodiment, the proximal controller 5130 comprises a syringe-like reservoir of air or fluid that is used to deploy (e.g., inflate, expand) the cleaning member 5130. As previously described, the volume of air or fluid to be injected into the cleaning member 5135, may be determined by the size of the chest tube 5105 being cleared and may be preset by one or more holes in a cylinder including the reservoir, such as described above. In some embodiments, multiple holes are placed along the length of the cylinder or a reservoir of the inflation or expansion mechanism corresponding to different sizes (e.g., internal diameters) of tubes. A single cleaning device may be adapted for use of different sized tubes by covering one or more of the holes so as to control the amount of volume of air or fluid that can be stored. In addition, the hole(s) may facilitate venting to atmosphere through the pilot channel so as to prevent leaks. The coupling member 5134 may comprise a clip or clamp that is integrated into the proximal controller 5130. The coupling member 5134 may be used to keep the closed clearing catheter module 5120 connected to and in line with the flexible drainage tubing 5115 between clearing procedures.

FIG. 22B illustrates that an adapter 5150 may be used to connect the closed chest cleaning system 5100 to two chest tubes 5105A, 5105B connected in a Y fashion. In one embodiment, the adapter 5150 comprises a swivel connector 5155 at the base of the Y of the adapter that by a 180° swivel or other manipulation allows the cleaning catheter 5125 to be inserted into either of the chest tubes 5105 that are connected by the adapter 5150. Similar swivel mechanisms are described herein for other adapters and the adapter 5150 may include any of the structural or design features or functions of those swivel mechanisms.

In one embodiment, the coupling member 5134 is disengaged from the flexible drainage tubing 5115. The catheter 5125 is inserted until it stops (the end of the chest tube 5105 may be sealed so that the catheter 5125 cannot pass freely into the pleural space) or the catheter 5125 can be inserted to a depth where the numbered markings on the catheter 5125 match corresponding numbered markings on the chest tube 5105. The proximal controller 5130 may then be depressed or otherwise actuated to inflate the cleaning member 5135 and the catheter 5125 is withdrawn to its position with the cleaning member 5135 back in its nominal position in the side arm of the adapter 5115. Thrombus or other material that has been removed from the lumen of chest tube 5105 can then be further milked down the drainage system by manual "stripping" of the flexible drainage tubing 5115 back towards a source of suction and a drainage reservoir. For use with chest tubes connected in a Y fashion, the swivel connector 5155 may then be rotated 180° and the procedure may be repeated with the catheter 5125 being inserted into and cleaning the second chest tube.

Figure 23:
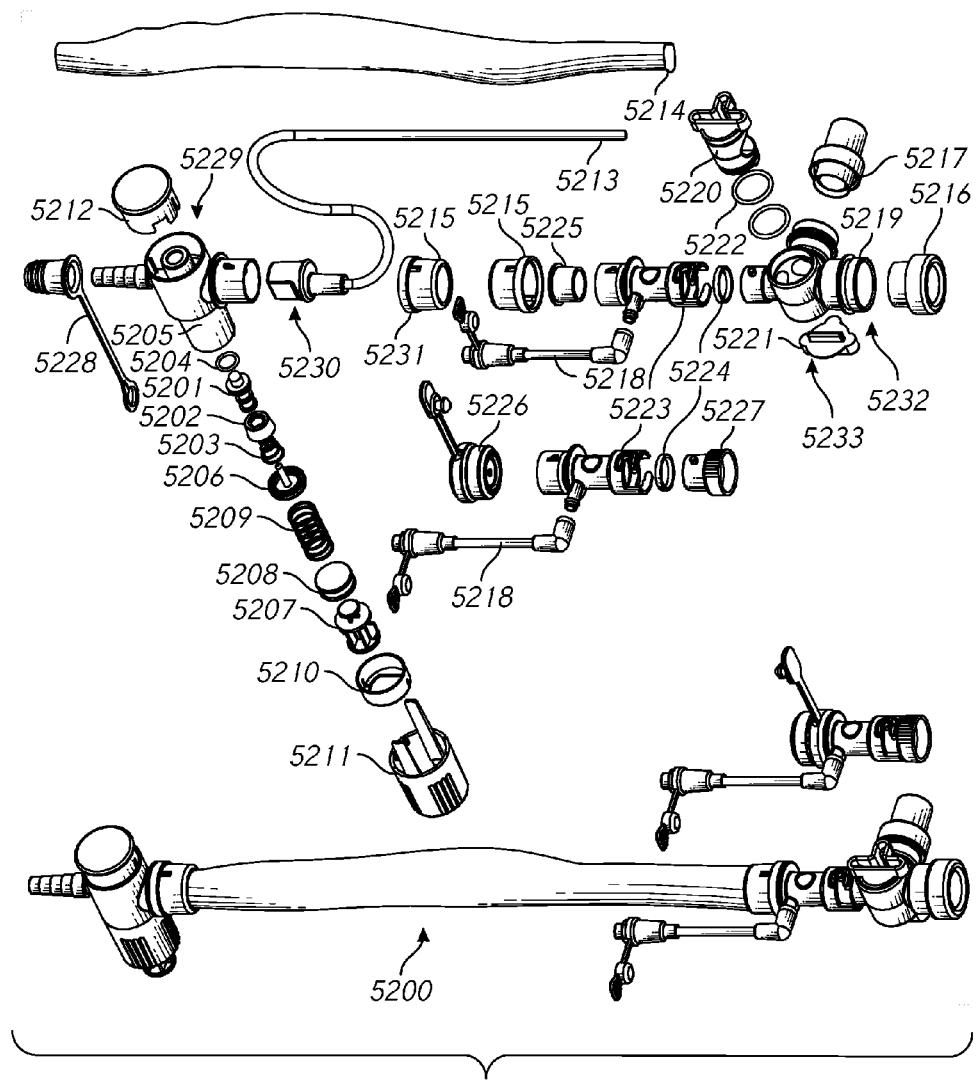
FIG. 23 illustrates an exploded assembly view of another embodiment of a closed suction system.

FIG. 23 is an exploded view and a perspective assembled view of an embodiment of a closed suction system 5200 including a suction catheter 5213 having an integrated body-inserted tube cleaner (not shown). In the illustrated embodiment, the closed suction system 5200 comprises a proximal controller 5229 having a proximal control valve housing 5205, a suction control valve cap 5212, an inflation valve cap 5207 and a rotating lock or status control member 5211 having markings or other indicia indicating that the rotating lock 5211 rotates and marks or other indicia indicating the operational status of the device (e.g., locked—no suction or cleaning member deployment, suction only, actuation of cleaning member only). In one embodiment, rotation of the lock or status control member 5211 lines up marks on the lock 5211 with marks on the housing 5205, showing closure, and locks the suction control valve cap 5212 and the inflation valve cap 5207 so that they are unable to be depressed. The proximal controller 5229 of the illustrated embodiment comprises a first O-ring 5204, a pillar housing 5201, a pillar rubber gasket 5202, a pillar spring 5203, and a suction cap 5206 that, together with the control valve housing 5205 and the suction control valve cap 5212 perform the suction functions of the closed suction system 5200. The proximal controller 5229 comprises an actuator spring 5209, a syringe-like inflation valve 5208, an inflation valve housing 5210 and the inflation valve cap 5207 configured to perform the inflation functions of the closed suction system 5200. The amount of air to be displaced into the distal cleaning member (not shown) of the suction catheter 5213 for the particular size endotracheal tube or other body-inserted tube may be controlled by placement of holes (one or more holes) in the proximal controller housing 5229 and or by adjusting the displacement of the inflation valve 5208. Differing closed suction devices may be labeled for the appropriate size body-inserted tube on which it is to be used, with the holes placed appropriately for that particular device at manufacture. In some embodiments, multiple holes are placed along the length of the proximal controller housing 5229 or a reservoir of the inflation or expansion mechanism corresponding to different sizes (e.g., internal diameters) of tubes. A single closed suction device may be adapted for use of different sized tubes by covering one or more of the holes so as to control the amount of volume of air or fluid that can be stored. In addition, the hole(s) may facilitate venting to atmosphere through the pilot channel so as to prevent leaks.

In some embodiments, a molded proximal portion 5230 of a suction catheter 5213 is configured to couple to or mate with a port of the proximal controller 5229. The suction catheter 5213 may comprise an integrated tube cleaning member, such as described in connection with FIG. 18. The suction catheter 5213 and its integrated tube cleaning member may comprise any of the structural features of the suction catheters or suction catheter systems described herein or in WIPO Publ. No. WO2014/089028, the entire content of which is hereby incorporated herein by reference. In some embodiments, the suction catheter 5213 may comprise a mechanically-actuated cleaning member instead of an inflatable cleaning member, such as the mechanically-actuated cleaning members described in more detail above or in US Publ. No. 2011/0023885, the entire content of which is hereby incorporated herein by reference. In such embodiments, the inflation valve cap 5207 may be replaced with a mechanical actuation control assembly.

In some embodiments, the closed suction system 5200 further comprises a protective, flexible and collapsible sheath 5214 that encloses the suction catheter 5213 and protects the suction catheter 5213 against contamination. The sheath 5214 may extend from a manifold 5232 to the proximal controller 5229. The sheath 5214 may be coupled to the manifold coupler 5223 via a first coupling member 5215 and coupled to the proximal controller 5229 via a second coupling member 5231.

In one embodiment, the manifold 5232 comprises a manifold housing or main body 5219. The manifold 5232 may also comprise a first swivel connector 5216 configured to couple to a distal port of the manifold housing 5219 and to a body-inserted tube, e.g., endotracheal tube (not shown). The components of the first swivel connector 5216 may be constructed or designed so that there is a smooth transition and no edge inside the first swivel connector 5216 that could catch on the cleaning member of the suction catheter 5213 as it is withdrawn into the body 5219 of the manifold 5232. The manifold 5232 may further comprise a second swivel connector 5217 configured to couple to a side port of the manifold housing 5219 and to a ventilator (not shown). The first swivel connector 5216 and the second swivel connector 5217 may be configured to couple to the manifold housing 5219 via friction fit coupling, interference fit coupling, threaded coupling, or other coupling mechanisms.

In one embodiment, the manifold 5232 comprises a stopcock assembly 5233 comprising a control valve 5220 which may be controlled (e.g., turned or rotated) so that the closed suction system, ventilator, and body-inserted tube into the patient are all in continuity. The control valve 5220 may include directional arrows or other indicators to indicate how it may be closed to isolate the closed suction system from the ventilator circuit while maintaining the connection from the ventilator to the body-inserted tube (e.g., endotracheal tube) and the patient. The stopcock assembly 5233 may include a cap 5221 configured to interface or mate with an end of the control valve 5220 through the main housing 5219 of the manifold 5232 and one or more O-rings 5222 to facilitate sealing.

The manifold 5232 may be removably coupled to the rest of the closed suction system (e.g., the sheath 5214, the suction catheter 5213 and the proximal controller 5229) via a modular connector 5223. The modular connector 5223 may comprise a gasket 5224 and a secretion removing member 5225 comprising a diaphragm configured to wipe secretions from the catheter 5213 as it is withdrawn out of the patient. A proximal end of the modular connector 5223 may be configured to be inserted within the second coupling member 5215. Modular coupling cap 5227 may be removably coupled to modular connector 5223 for storage of the closed suction system 5200 (e.g. during bronchoscopic procedures or to minimize bulk hanging off the patient).

The closed suction system 5200 may optionally comprise an irrigation unit 5218 that is configured to attach to the modular connector 5223. The irrigation unit 5218 may be used to irrigate and clean the suction catheter 5213 (e.g., the cleaning member of the suction catheter 5213) once it has been withdrawn from the patient and isolated from the ventilator circuit by closing the stopcock assembly 5233. The closed suction system 5200 may optionally comprise a cap 5226 that is configured to couple to a proximal inlet port of the manifold 5232 or directly to the body-inserted tube (or a universal connector of the body-inserted tube) upon removal of the modular connector 5223 from the manifold 5232 or upon removal of the manifold 5232 from the body-inserted tube. The cap 5226 may be configured to allow for instrumentation of the patient's airway. An embodiment of the cap 5226 is further described in connection with FIG. 20.

In accordance with several embodiments, the closed suction system 5200 is connected to a body-inserted tube (e.g., endotracheal tube) and a ventilator via the manifold 5232. In some embodiments, the patient is hyper-oxygenated for several minutes. The control valve 5220 of the stopcock assembly 5233 may be turned to open the ventilator and patient to the closed suction system 5200 and the catheter 5213 may be inserted into the body-inserted tube until depth marks on the catheter 5213 line up with depth marks on the body-inserted tube that is being cleaned or otherwise treated. At the time of this first cleaning, a movable depth stop on the catheter 5213 may be moved and juxtaposed to the second coupling member 5215 connected to the manifold 5232, thereby allowing for both visual and mechanical guidance for depth of insertion at subsequent cleanings. In some embodiments, the proximal controller 5229 is hooked to suction tubing and the strength of suction is set according to the American Association of Respiratory Care (AARC) guidelines.

After connection of the proximal controller 5229 to the suction tubing via a suction inlet of the proximal controller 5229, the rotating lock or other control member 5211 may be rotated (e.g., sixty degrees) from its locked position to a position where arrows or other indicators show alignment of the housing 5205 with a marking on the rotating lock 5211 indicative of a suction operational state. The suction control valve cap 5212 can then be depressed, thereby applying suction to the catheter 5213 and the catheter 5213 is withdrawn from the body-inserted tube back into the closed suction system 5200. Upon removal of the catheter 5213 from the body-inserted tube and into the manifold 5232, the stopcock assembly 5233 may be closed and the suction catheter 5213 is cleaned by irrigating saline or other fluid into the manifold 5232 through the irrigation unit 5218 while simultaneously applying suction to the catheter tip, thereby cleaning both the suction catheter tip and the cleaning member.

Further cleaning may be performed by reopening the stopcock assembly 5233 and inserting the suction catheter 5213 again into the body-inserted tube either by aligning depth marks on the catheter 5213 with corresponding depth marks on the body-inserted tube, or by using the visual and mechanical stop that was placed previously to guide depth of insertion. The rotating lock or operational control member 5211 may then be manipulated (e.g., turned sixty degrees) to align the arrows or other indicators on the housing 5205 with marking on the rotating lock 5211 indicative of a cleaning member operational state. The inflation valve cap 5207 may then be depressed to deploy (e.g., expand, inflate) the cleaning member to a predetermined size chosen for the body-inserted tube being cleaned. In one embodiment, the suction catheter 5213 is then slowly withdrawn (e.g., over a period of 3-5 seconds) back into the manifold 5232 and the stopcock assembly 5233 is once again closed. The catheter tip and cleaning member may then again be cleansed utilizing the irrigation unit 5218 by injecting saline while simultaneously utilizing the suction to empty the debris and residual saline. The amount of air or fluid displaced into the cleaning member may be predetermined for differing size tubes by utilization of one or more holes placed at specific sites in the cylinder in which the air to be displaced is stored. In some embodiments, multiple holes are placed along the length of the cylinder or reservoir of the inflation or expansion mechanism corresponding to different sizes (e.g., internal diameters) of tubes. A single suction device may be adapted for use of different sized tubes by covering one or more of the holes so as to control the amount of volume of air or fluid that can be stored. In addition, the hole(s) may facilitate venting to atmosphere through the pilot channel so as to prevent leaks. The closed suction system 5200 of FIG. 23 may incorporate any of the features or structures described with respect to the cleaning systems (e.g., closed or partially-closed suction systems) described in connection with FIGS. 1-19 and may be adapted to be used in connection with the accessory adapters, caps or manifolds described herein.

Figure 23A:
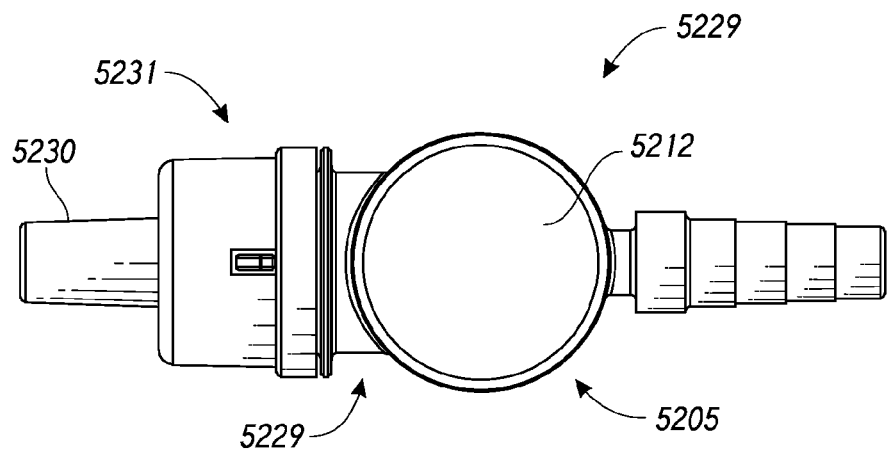

FIG. 23A is an isometric top assembled view of an embodiment of the proximal controller 5229 of the closed suction system 5200. In the illustrated embodiment, the proximal controller 5229 comprises a suction control valve cap 5212, a molded proximal portion 5230 (e.g., of the suction catheter 5213), a second coupling member 5231 and a control valve housing 5205. When unlocked by rotating lock 5211 or another status control member (not shown) and in the suction only position, depressing the suction control valve cap 5212 allows the user to perform a suctioning procedure.

Figure 23B:
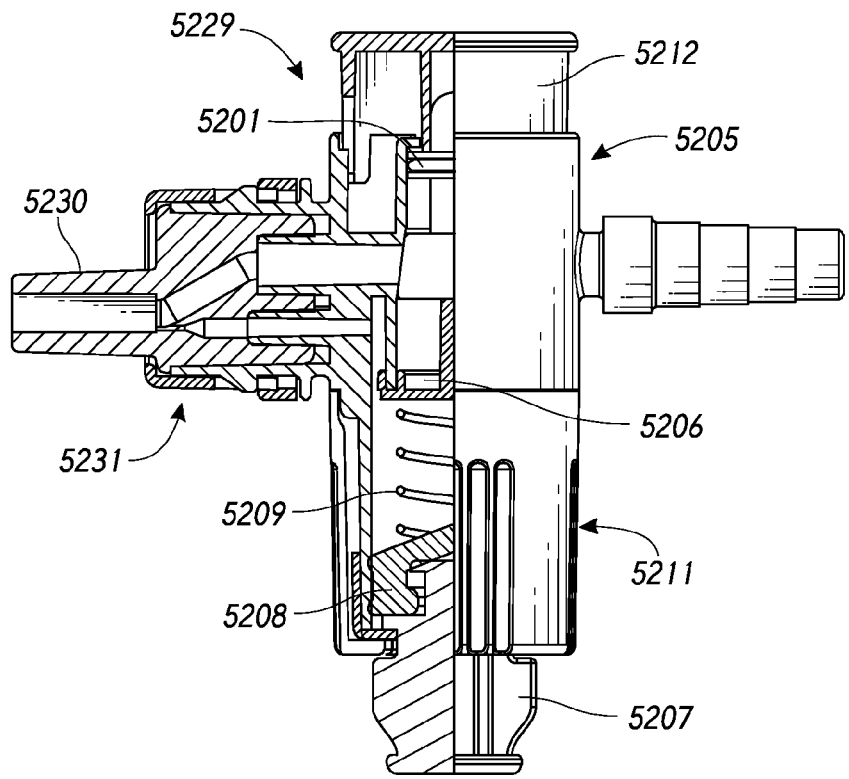

FIG. 23B is an isometric sectioned side assembly view of an embodiment of the proximal controller 5229. In the illustrated embodiment, the proximal controller 5229 comprises the suction control valve cap 5212, the inflation valve cap 5207, the molded proximal portion 5230, the second coupling member 5231, the control valve housing 5205, the actuator spring 5209, the syringe-like inflation valve 5208, the suction cap 5206 and the rotating lock 5211 having markings (not shown) indicating that the rotating lock 5211 rotates and marks indicating the status of the device (e.g., locked, suction only, activation of cleaning member only). In one embodiment, rotation of the lock 5211 lines up marks on the lock 5211 with marks on the housing 5205, showing closure, and locks the suction control valve cap 5212 and inflation valve cap 5207 so that they are unable to be depressed. When aligned in the suction or actuation only positions, suction or actuation, respectively, are permitted.

Figure 23C:
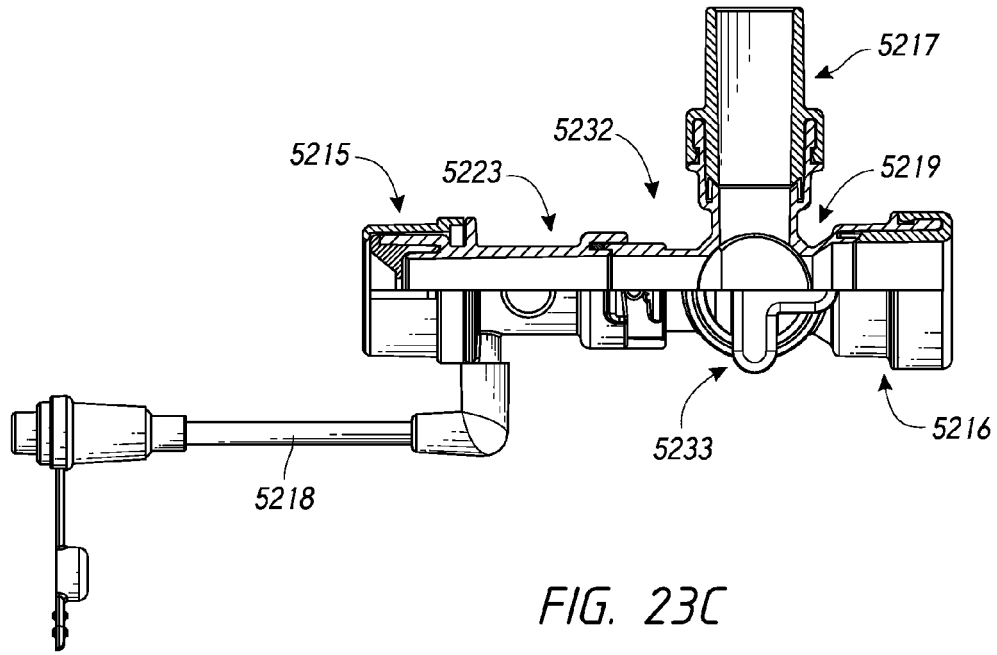

In FIG. 23C an isometric side sectioned view of the manifold 5232 is shown to provide more detail. The manifold 5232 comprises the main housing 5219, the irrigation unit 5218, the first coupling member 5215, the modular connector 5223, the first swivel connector 5216, the second swivel connector 5217 and the stopcock assembly 5233. The stopcock assembly 5233 may be alternately opened and closed to permit and restrict access of the suction catheter 5213 to the endotracheal tube (not shown).

Figure 23D:
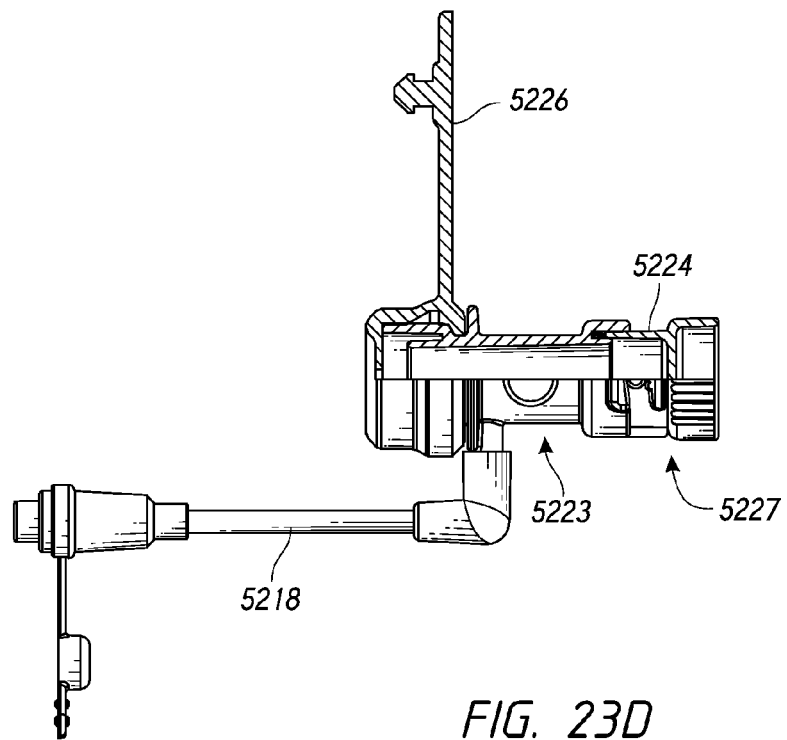

In FIG. 23D an isometric side sectioned view of the removably coupled modular connector 5223, the cap 5226, the irrigation unit 5218, the gasket 5224 and the modular coupling cap 5227 are shown in more detail. The assembly may be used to enable access to the endotracheal tube when coupled to the manifold 5232. The cap 5226 may be removably coupled to the closed suction system 5200 in the place of the manifold 5232 allowing sterile storage outside of the ventilatory circuit.

In FIG. 23E an isometric side view of the removably coupled manifold modular connector 5223, the cap 5226, the irrigation unit 5218, and the modular coupling cap 5227 are shown in more detail. The assembly may be used to enable access to the endotracheal tube when coupled to the manifold 5232. The cap 5226 may be removably coupled to the closed suction system 5200 in the place of the manifold 5232, thereby allowing sterile storage outside of the ventilatory circuit.

In FIG. 23F an isometric side view of the closed suction system 5200 is shown without the sheath 5214 for illustration purposes. The system 5200 comprises a sheath 5214 (not shown), a proximal controller 5229 comprising a proximal control valve housing 5205 and a suction control valve cap 5212, an inflation valve cap 5207 and a rotating lock 5211 having markings indicating that the rotating lock 5211 rotates and marks indicating the status of the device (e.g., locked, suction only, activation of cleaning member only), a second coupling member 5231, a molded proximal portion 5230 of a suction catheter 5213, a first coupling member 5215, a manifold 5232 comprising a manifold housing or main body 5219, a first swivel connector 5216 configured to couple to a distal port of the manifold housing 5219 and to a body-inserted tube, e.g., endotracheal tube (not shown), a second swivel connector 5217 configured to couple to a side port of the manifold housing 5219 and to a ventilator (not shown) and a control valve 5220.

FIG. 23F further illustrates an embodiment of visual indicia 5280 indicative of three operational states in which the proximal controller 5229 is adapted to function. The visual indicia 5280 may comprise alphanumeric characters, icons or symbols corresponding to the operational state (e.g., a locked icon, a suction icon and a cleaning member icon), colors, protrusions, and/or other indicia. In some embodiments, the current operational state is determined/effected by aligning a mark or indicia on a main housing 5205 of the proximal controller 5229 with one of the visual indicia 5280, as described further above. The spacing may vary as desired and/or required. For example, the spacing between the indicia 5280 may be about 10 degrees, about 15 degrees, about 20 degrees, about 25 degrees, about 30 degrees, about 35, degrees, about 40 degrees, about 50 degrees, about 55 degrees, about 60 degrees about 65 degrees, about 70 degrees, about 80 degrees, about 90 degrees or more than 90 degrees. For safety reasons, neither suction nor cleaning member deployment or expansion may be possible when the corresponding marks or indicia are not aligned (e.g., during transitions between operational states), in accordance with some embodiments.

Although the cleaning devices, methods, and systems described herein have been described in connection with the cleaning of endotracheal tubes or other body-inserted tubes or with the suctioning of distal airways of a patient, the embodiments and features described herein can be used for other medical applications, such as, for example, urologic applications; endoscopy, laparoscopic applications, orthopedic and spine applications, and for tubes within the body such as dialysis grafts. The methods disclosed herein include certain actions taken by a practitioner; however, they can also include any third-party instruction of those actions, either expressly or by implication. For example, actions such as "inserting a suction catheter" include "instructing the insertion of a suction catheter."

Conditional language, for example, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

Although several embodiments and examples are disclosed herein, the present application extends beyond the specifically disclosed embodiments to other alternative embodiments and/or uses of the inventions and modifications and equivalents thereof. It is also contemplated that various combinations or subcombinations of the specific features and aspects of the embodiments may be made and still fall within the scope of the inventions. Accordingly, it should be understood that various features and aspects of the disclosed embodiments can be combined with or substituted for one another in order to form varying modes of the disclosed inventions. Thus, it is intended that the scope of the embodiments herein disclosed should not be limited by the particular disclosed embodiments described above.

Some embodiments have been described in connection with the accompanying drawings. However, it should be understood that the figures are not drawn to scale. Distances, angles, etc. are merely illustrative and do not necessarily bear an exact relationship to actual dimensions and layout of the devices illustrated. Components can be added, removed, and/or rearranged. Additionally, the skilled artisan will recognize that any of the above-described methods can be carried out using any appropriate apparatus. Further, the disclosure herein of any particular feature, aspect, method, property, characteristic, quality, attribute, element, or the like in connection with various embodiments can be used in all other embodiments set forth herein. Additionally, process steps may be added, removed, or reordered. The ranges disclosed herein encompass any and all overlap, subranges, and combinations thereof, as well as individual numerical values within that range. For example, description of a range such as from about 4 mm to about 7 mm should be considered to have specifically disclosed subranges such as from 4 to 6 mm, from 5 to 7 mm, etc., as well as individual numbers within that range, for example, 4, 5.5, 6, 6.5, 7 and any whole and partial increments therebetween. Language such as "up to," "at least," "greater than," "less than," "between," and the like includes the number recited. Numbers preceded by a term such as "about" or "approximately" include the recited numbers. For example, the terms "approximately", "about", and "substantially" as used herein represent an amount close to the stated amount that still performs a desired function or achieves a desired result.

For purposes of this disclosure, certain aspects, advantages, and novel features of the inventions are described herein. It is to be understood that not necessarily all such advantages may be achieved in accordance with any particular embodiment of the invention. Thus, for example, those skilled in the art will recognize that the inventions may be embodied or carried out in a manner that achieves one advantage or group of advantages as taught herein without necessarily achieving other advantages as may be taught or suggested herein.

What is claimed is:

1. A cleaning system adapted to clean a body-inserted tube, the system comprising:
    a suction catheter comprising:
    a cleaning portion located at or near a distal end of the suction catheter, the cleaning portion comprising an expandable cleaning member;
    a proximal controller located at a proximal end of the suction catheter,
    wherein the proximal controller comprises a first activation member adapted to control expansion of the cleaning member and a second activation member adapted to allow a suction force to be applied to the suction catheter by a suction source,
    wherein the proximal controller is adapted to enable operation in the following three operational states:
        i) a first operational state in which the first activation member is allowed to be activated by an operator and in which the second activation member is prevented from being activated by the operator,
        ii) a second operational state in which the second activation member is allowed to be activated by the operator and in which the first activation member is prevented from being activated by the operator, or
        iii) a third operational state in which neither the first activation member nor the second activation member is allowed to be activated by the operator;
    wherein, upon expansion of the cleaning member, at least a portion of the cleaning member is adapted to contact an interior surface of the body-inserted tube such that when the suction catheter is withdrawn from the body-inserted tube, biofilm or other debris collected on the interior surface is removed by the cleaning member; and
    a distal suction port disposed distal of the cleaning member along a length of the suction catheter, the suction port being in fluid communication with a lumen extending from the proximal controller to the distal suction port,
    wherein the distal suction port is configured to facilitate suctioning distal to the cleaning member.

2. The system of claim 1, wherein the proximal controller is adapted to rotate between three rotational positions, each rotational position corresponding to one of the three operational states.

3. The system of claim 2, wherein the proximal controller includes visual indicia corresponding to each rotational position and corresponding operational state.

4. The system of claim 2, wherein rotation between each rotation position is adapted to be confirmed by an audible confirmation, a visual confirmation and a tactile confirmation.

5. The system of claim 1, wherein the proximal controller further comprises a locking mechanism configured to prevent inadvertent activation of the first activation member and/or the second activation member.

6. The system of claim 1, wherein the cleaning member comprises an inflatable balloon having one or more integrated rings or wipers.

7. The system of claim 6, wherein a leading edge of the one or more rings or wipers comprises a squared or substantially squared edge.

8. The system of claim 1, wherein the cleaning member and/or a portion of the length of the suction catheter comprises an integral lubricious coating.

9. The system of claim 1, wherein the cleaning member and/or a portion of the length of the suction catheter comprises an antimicrobial coating.

10. The system of claim 1, wherein the suction catheter and the cleaning member are formed of silicone.

11. The system of claim 1, further comprising a manifold adapted to removably couple to the body-inserted tube and a flexible enclosure adapted to extend from the proximal controller to a coupling member at the distal end of the suction catheter that couples to the manifold, thereby preventing exposure of the suction catheter to an external environment.

12. The system of claim 1, wherein the suction catheter comprises a braided wire coextruded with at least the portion of the suction catheter.

13. The system of claim 11, further comprising a polymeric tubular extension comprising a shaft having a length extending into the flexible enclosure from the coupling member at the distal end of the suction catheter, wherein the polymeric tubular extension is configured to receive a flexible catheter and facilitate pulling of the flexible catheter into the the manifold and the body-inserted tube by the operator.

14. A cleaning device adapted to clean a body-inserted tube, the system comprising:
    a suction catheter comprising a proximal end and a distal end;
    a deployable cleaning member located at or near the distal end of the suction catheter;
    a proximal controller located at the proximal end of the suction catheter,
    wherein the proximal controller comprises a first activation member adapted to control deployment of the cleaning member and a second activation member adapted to allow a suction force to be applied to the suction catheter by a suction source, wherein the proximal controller is adapted to enable operation in the following three operational states:
   i) a first operational state in which the first activation member is allowed to be activated by an operator and in which the second activation member is prevented from being activated by the operator,
   ii) a second operational state in which the second activation member is allowed to be activated by the operator and in which the first activation member is prevented from being activated by the operator, or
   iii) a third operational state in which neither the first activation member nor the second activation member is allowed to be activated by the operator;

wherein, upon deployment of the cleaning member, at least a portion of the cleaning member is adapted to contact an interior surface of the body-inserted tube such that when the cleaning device is withdrawn from the body-inserted tube, biofilm or other debris collected on the interior surface is removed by the cleaning member; and a distal suction port disposed distal of the cleaning member along a length of the suction catheter, the suction port being in fluid communication with a lumen extending from the proximal controller to the distal suction port, wherein the distal suction port is configured to facilitate suctioning distal to the cleaning member.

15. The device of claim 14, wherein the deployable cleaning member comprises an inflatable balloon.

16. The device of claim 14, wherein the proximal controller further comprises a locking mechanism configured to prevent inadvertent activation of the first activation member and/or the second activation member.

17. The device of claim 14, wherein the suction catheter comprises a braided wire coextruded with at least the portion of the suction catheter.

* * * * *

UNITED STATES PATENT AND TRADEMARK OFFICE
CERTIFICATE OF CORRECTION

PATENT NO. : 10,016,575 B2  
APPLICATION NO. : 14/727665  
DATED : July 10, 2018  
INVENTOR(S) : Brad Eugene Vazales et al.

Page 1 of 1

It is certified that error appears in the above-identified patent and that said Letters Patent is hereby corrected as shown below:

In the Specification

At Column 14, Line 65, please change "bronchioalveolar" to, --bronchoalveolar--.

At Column 20, Line 47, please change "bronchioalveolar" to, --bronchoalveolar--.

At Column 33, Line 62, please change "bronchioalveolar" to, --bronchoalveolar--.

At Column 34, Line 27, please change "bronchioalveolar" to, --bronchoalveolar--.

At Column 34, Line 50, please change "bronchioalveolar" to, --bronchoalveolar--.

At Column 36, Line 29, please change "bronchioalveolar" to, --bronchoalveolar--.

In the Claims

At Column 58, Line 56, In Claim 13, please change "the the" to, --the--.

Signed and Sealed this  
Twenty-eighth Day of May, 2019

Andrei Iancu  
*Director of the United States Patent and Trademark Office*